(12) United States Patent
Kawai et al.

(10) Patent No.: US 7,981,028 B2
(45) Date of Patent: Jul. 19, 2011

(54) ELECTRICALLY-OPERATED CURVING CONTROL DEVICE

(75) Inventors: Toshimasa Kawai, Yokohama (JP); Eiichi Kobayashi, Tama (JP); Takemitsu Honda, Hino (JP); Seiichiro Kimoto, Hachioji (JP)

(73) Assignee: Olympus Corporation, Tokyo (JP)

( * ) Notice: Subject to any disclaimer, the term of this patent is extended or adjusted under 35 U.S.C. 154(b) by 1185 days.

(21) Appl. No.: 11/708,518

(22) Filed: Feb. 20, 2007

(65) Prior Publication Data

US 2007/0161861 A1     Jul. 12, 2007

Related U.S. Application Data

(63) Continuation of application No. PCT/JP2005/015069, filed on Aug. 18, 2005.

(30) Foreign Application Priority Data

Aug. 19, 2004   (JP) ................................. 2004-239906

(51) Int. Cl.
   *A61B 1/005*   (2006.01)
(52) U.S. Cl. .................. 600/145; 600/146; 600/152
(58) Field of Classification Search .................. 600/118, 600/117, 145, 146, 152
   See application file for complete search history.

(56) References Cited

U.S. PATENT DOCUMENTS

| | | | |
|---|---|---|---|
| 4,941,454 A | 7/1990 | Wood et al. | |
| 4,982,725 A * | 1/1991 | Hibino et al. | 600/117 |
| 5,060,632 A | 10/1991 | Hibino et al. | |
| 5,159,446 A * | 10/1992 | Hibino et al. | 348/65 |
| 5,243,967 A | 9/1993 | Hibino | |
| 5,400,769 A | 3/1995 | Tanii et al. | |
| 5,609,563 A * | 3/1997 | Suzuki et al. | 600/118 |
| 5,658,238 A * | 8/1997 | Suzuki et al. | 600/150 |
| 5,976,074 A * | 11/1999 | Moriyama | 600/144 |
| 6,371,907 B1 | 4/2002 | Hasegawa et al. | |
| 7,060,027 B2 * | 6/2006 | Maeda et al. | 600/150 |
| 7,331,924 B2 * | 2/2008 | Arai et al. | 600/145 |
| 2002/0165430 A1 | 11/2002 | Matsui | |
| 2002/0165432 A1 * | 11/2002 | Matsui | 600/145 |
| 2003/0195389 A1 * | 10/2003 | Motoki et al. | 600/146 |
| 2004/0034279 A1 * | 2/2004 | Arai et al. | 600/152 |
| 2004/0054258 A1 * | 3/2004 | Maeda et al. | 600/152 |
| 2004/0073083 A1 | 4/2004 | Ikeda et al. | |
| 2004/0193014 A1 * | 9/2004 | Miyagi et al. | 600/146 |
| 2004/0193015 A1 * | 9/2004 | Ikeda et al. | 600/146 |
| 2006/0069310 A1 * | 3/2006 | Couvillon, Jr. | 600/148 |
| 2007/0112255 A1 * | 5/2007 | Ikeda et al. | 600/146 |

FOREIGN PATENT DOCUMENTS

JP        04-079931        3/1992

(Continued)

OTHER PUBLICATIONS

Extended Supplementary European Search Report dated Feb. 15, 2011.

*Primary Examiner* — John P Leubecker
(74) *Attorney, Agent, or Firm* — Scully, Scott, Murphy & Presser, P.C.

(57) ABSTRACT

A curving control device to which an electrically-controlled endoscope is connected has a main CPU for primarily performing curving driving control, and a monitoring CPU for monitoring whether the operating state relating to curving actions is normal or abnormal. IN the event of detecting an abnormality from the monitoring CPU, the curving control device also performs processing for handling the occurrence of the abnormality, such as outputting an emergency stop through an interlock via the main CPU, turning the main power and the like of a servo driver OFF.

11 Claims, 29 Drawing Sheets

FOREIGN PATENT DOCUMENTS

| | | |
|---|---|---|
| JP | 04-297221 | 10/1992 |
| JP | 05-038328 | 2/1993 |
| JP | 5-228102 | 9/1993 |
| JP | 6-169883 | 6/1994 |
| JP | 06-217925 | 8/1994 |
| JP | 06-304126 | 11/1994 |
| JP | 2000-316803 | 11/2000 |
| JP | 2003-245246 | 9/2003 |

* cited by examiner

FIG.3A FIG.3B
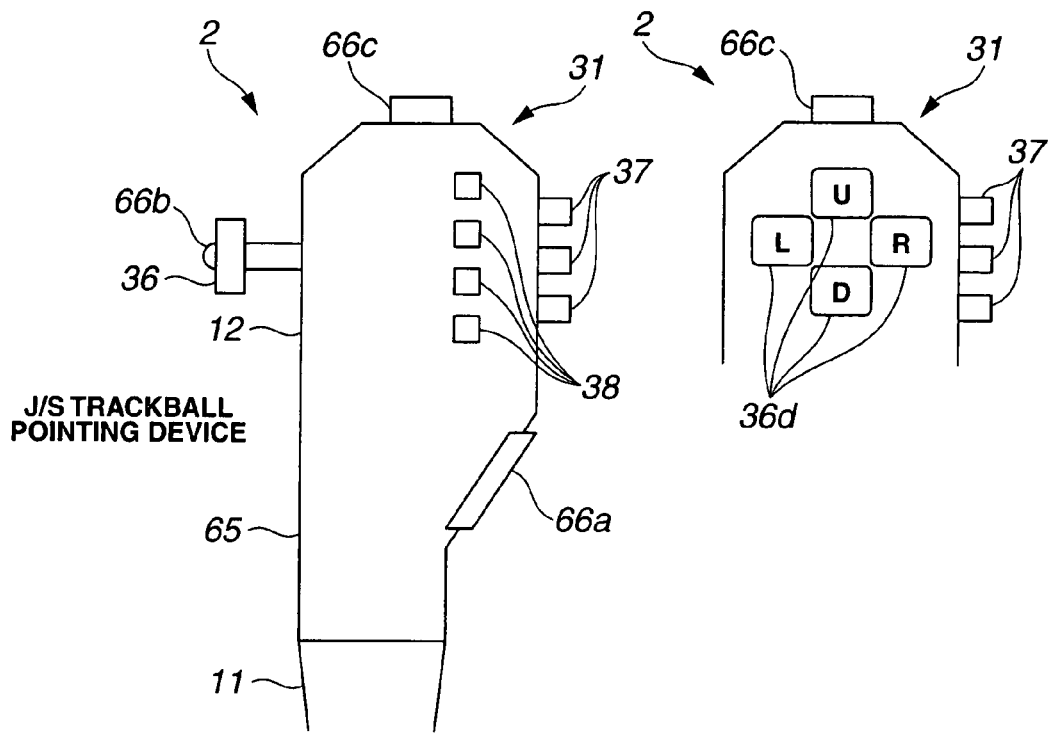
FIG.4
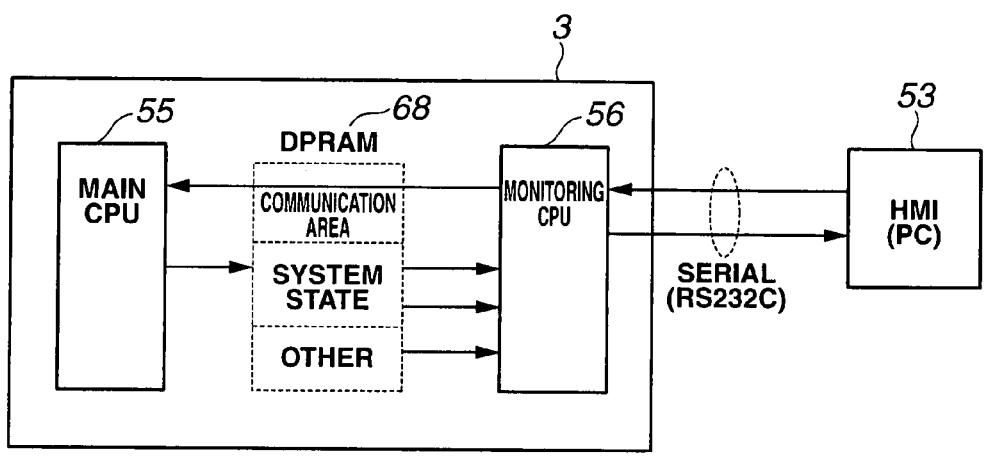

FIG.7

| FUNCTION ITEM | MODE | CONTENTS |
|---|---|---|
| CURVING | POSITION INSTRUCTION | RUN CURVING MOTOR BASED ON POSITION INSTRUCTION VALUE FROM OPERATION INPUT UNIT. |
| | SPEED INSTRUCTION | RUN CURVING MOTOR BASED ON SPEED INSTRUCTION VALUE FROM OPERATION INPUT UNIT. |
| | AUTOMATIC RECOVERY OF CURVED PORTION TO NEUTRAL POSITION | RETURN CURVED PORTION FROM CURVED STATE TO A STRAIGHT STATE. START AUTOMATIC RECOVERY WHEN NEUTRAL RECOVERY SWITCH IS TURNED ON. NO INSTRUCTIONS ACCEPTED FROM OPERATION INPUT UNIT WHILE PERFORMING AUTOMATIC RECOVERY. |
| | CURVED STATE (ANGLE) MONITOR | OUTPUT CURVED STATE (POTENTIOMETER POSITION, SLACK SENSOR INFORMATION) FROM MONITORING CPU SIDE SERIAL PORT (RS232C). COMMUNICATION SPEED: VARIABLE WITH SYSTEM PARAMETERS. INITIAL VALUE: 9600 bps COMMUNICATION CYCLE: VARIABLE WITH SYSTEM PARAMETERS. INITIAL VALUE: 100 msec. |
| | FREE CURVING | MECHANICAL CLUTCH OR ELECTROMAGNETIC CLUTCH IS PROVIDED BETWEEN DRIVING UNIT (MOTOR) AND OUTPUT UNIT (PULLING WIRE), SO AS TO REALIZE A FREE CURVING STATE IN THE CASE OF A MECHANICAL CLUTCH, A CLUTCH ENGAGEMENT STATE SIGNAL IS READ IN WITH A CONTROLLER. AS FOR AN OPERATING TACTIC, (1) FREE CURVING OR (2) EMERGENCY STOP CAN BE CONNECTED |
| AWS (AIR FEED/ WATER FEED/ SUCTION) | AIR FEED / WATER FEED OPERATIONS FROM OPERATION INPUT UNIT | PRESS SWITCH AT OPERATION INPUT UNIT FOR BOTH AIR FEED / WATER FEED, TO CONTROL AIR FEED AND WATER FEED AMOUNT. PREPARE MULTIPLE AIR FEED SEQUENCES, AND ARRANGE SO AS TO BE EASILY SWITCHED BETWEEN. SEQUENCE (1): AIR FEED AMOUNT VARIABLE, SEQUENCE (2): AIR FEED AMOUNT FIXED SEQUENCE (1): AIR FEED Do 4-bit: CONTROL IN 16 STAGES ACCORDING TO THE AMOUNT OF PRESSING SWITCH. Do 1-bit: ON WHEN SWITCH PRESSED, OFF WHEN RELEASED. SEQUENCE (2): AIR FEED Do 4-bit: ALL BITS ON WHEN SWITCH PRESSED HALFWAY. Do 1-bit: ON WHEN SWITCH PRESSED, OFF WHEN RELEASED. WATER FEED: Do 1-bit: ON WHEN SWITCH PRESSED ALL THE WAY. |
| | SUCTION OPERATIONS FROM OPERATION INPUT UNIT | ADJUST AMOUNT OF SUCTION BY PRESSING SUCTION SWITCH FROM OPERATION INPUT UNIT (5-bit ALLOCATION OF WATER FEED) SUCTION: Do 4-bit: CONTROL IN 16 STAGES ACCORDING TO THE AMOUNT OF PRESSING SWITCH. Do 1-bit: ON WHEN SWITCH PRESSED, OFF WHEN RELEASED. |
| SERIAL COMMUNICATION OPERATION UNIT | CONNECTION | CONNECTION BETWEEN CONTROLLER AND OPERATION INPUT UNIT BY SERIAL COMMUNICATION (RS485). |
| | COMMUNICATION SPEED | CHANGEABLE WITH SYSTEM PARAMETERS. COMMUNICATION SPEED: 19200 OR 38400 bps. |
| | COMMUNICATION CYCLE | CHANGEABLE WITH SYSTEM PARAMETERS. |
| | VARIATIONS WHICH CAN BE HANDLED | DETERMINATION OF OPERATION INPUT UNIT (COMMAND TYPE, CAPABLE RANGE, ETC) IS AUTOMATICALLY DETECTED. EACH OPERATION UNIT HAS A UNIQUE ID. THE UNIQUE OPERATION UNIT ID IS TRANSMITTED FROM THE OPERATION INPUT UNIT IMMEDIATELY AFTER ACTIVATING THE SYSTEM. THE SETTING PARAMETER TABLE IS SWITCHED ACCORDING TO THE UNIQUE OPERATION UNIT ID. AS MANY SETTING PARAMETER TABLES AS SUPPORTED OPERATION INPUT UNITS ARE PREPARED. POWER MUST BE TURNED OFF/ON TO REPLACE OPERATION UNITS. |
| OTHER OPERATION METHODS/FUNCTIONS | SYSTEM STARTUP/SHUTDOWN SEQUENCES | TURNING MAIN SWITCH ON STARTS UP SYSTEM. TURNING MAIN SWITCH OFF SHUTS DOWN SYSTEM. SYSTEM NEEDS TO BE ABLE TO BE QUIT REGARDLESS OF STATUS OF SYSTEM (DURING STARTUP, RUNNING NORMAL, WHEN MALFUNCTIONING, ETC.). IMMEDIATELY AFTER STARTUP, SYSTEM IS IN A CUT-OFF STOP STATE. IN ORDER TO START WORK, THE RELEASE SWITCH IS PRESSED TO CHANGED FROM THE CUT-OFF STOP STATE TO THE NORMAL STATE. |
| | SYSTEM STATE DISPLAY (UI PANEL) | LED 1 (GREEN): LIT WHEN SYSTEM IS OPERATING NORMALLY. LED 2 (RED): LIT WHEN IN ABNORMAL STATE. ALARM GENERATED AT THE SAME TIME. 3-DIGIT INDICATOR: DISPLAY SYSTEM ERROR INFORMATION. DISPLAY "000" WHEN SYSTEM IS RUNNING NORMALLY. DISPLAY ERROR CODE IN CASE OF SYSTEM MALFUNCTION. |
| | SCOPE SWITCH | ACTIVATE SCOPE FUNCTION (E.G. IMAGE RELEASE). SCOPE SWITCH SIGNAL BETWEEN OPERATION INPUT UNIT AND CV (ENDOSCOPE SYSTEM) IS ELECTRICALLY DIRECTLY CONNECTED MCU MAIN BLOCK READS ID PROVIDED TO SCOPE VIA SERIAL COMMUNICATION (RS485) AND SETS A PARAMETER TABLE CORRESPONDING TO THE ID IN THE SYSTEM. |
| | EMERGENCY STOP BUTTON | PRESSING THIS BUTTON ENABLES THE SYSTEM TO BE PLACED IN AN EMERGENCY STOP STATE. IN THE EMERGENCY STOP STATE, THE SERVO AMP AND AWS HARDWARE ARE OFF. SYSTEM RECOVERY IS PERFORMED BY RELEASING THIS BUTTON, AND THEN TURNING THE POWER ON AGAIN. |
| | RELEASE BUTTON | IN THE CASE OF A CUT-OFF STOP, PRESSING THE RELEASE BUTTON RESTORES THE SYSTEM. IN THE CASE OF DISPLAYING A WARNING, PRESSING THE RELEASE BUTTON RELEASES THE WARNING DISPLAY. IN THE CASE OF AN EMERGENCY STOP, PRESSING THE RELEASE BUTTON DOES NOT RESTORE THE SYSTEM. |
| | MANUAL MODE | VARIOUS OPERATIONS CAN BE PERFORMED FROM OTHER THAN OPERATING MEANS CONNECTED TO THE SCOPE. AUTOMATIC/MANUAL SWITCHOVER AVAILABLE. |

FIG.8

| FUNCTION ITEM | MODE | CONTENTS |
|---|---|---|
| SYSTEM FUNCTIONS | SETTING/CHANGING SYSTEM PARAMETERS | CONNECT PC TO CONTROLLER, AND SET/CHANGE PARAMETERS BY SERIAL COMMUNICATION (RS232C). TO BE USED FOR ADJUSTMENT PRIOR TO SHIPPING, AND FOR MAINTENANCE. CONNECT TO SERIAL PORT OF MONITORING BLOCK. |
| | DATA LOGGING | RECORD OF SYSTEM STARTUP (svaLog) ERROR RECORD (errLog) REAL-TIME RECORD OF OPERATIONAL STATE (dtLog) RECORD IN SRAM, SO THAT DATA CAN BE OUTPUTTED EXTERNALLY AS NECESSARY. |
| | SYSTEM MONITORING | MUTUAL MONITORING AMONG BLOCKS: A 2-CPU CONFIGURATION IS USED TO MONITOR THE STATE OF THE MAIN BLOCK (FOR REALIZING BASIC FUNCTIONS) WITH A MONITORING BLOCK. EXTERNAL SENSOR MONITORING: EXTERNAL SENSORS: ENCODER, POTENTIOMETER, SLACK SENSOR, AWS PRESSURE DETECTOR, DETECTING MEANS INTERNAL SYSTEM MONITORING: RAM: READ/WRITE CHECK UPON SYSTEM STARTUP WATCHDOG TIMER (WDT): SMALLEST VALUE FOR TIMER IS SERVO CYCLE COMMUNICATION MONITORING: SERIAL COMMUNICATION STATE MONITORING • WITH REGARD TO OPERATION INPUT UNIT: · METHOD OF RESPONDING TO CYCLICAL REQUESTS FROM CONTROLLER IS EMPLOYED (MALFUNCTION IF NO RESPONSE). · CHECKSUM ADDED TO DATA. • WITH REGARD TO PERIPHERAL DEVICES (CURVING DISPLAY DEVICE, MAINTENANCE HMI): MCU (SERVER) RESPONDS TO REQUESTS FROM PERIPHERAL DEVICES (CLIENTS). · CHECKSUM ADDED TO DATA. |
| | INTERLOCK | SERVO DOES NOT START UP UNLESS INTERLOCKING CONDITIONS ARE SATISFIED. |
| | RAS | CPU POWER SOURCE VOLTAGE MONITORING |
| | CALIBRATION | THIS FUNCTION IS AUTOMATICALLY ACTIVATED UPON SYSTEM INITIALIZATION. THIS FUNCTION IS TO BE CAPABLE OF BEING MANUALLY ACTIVATED IN THE MANUAL MODE (PROCESSING 1 AND 2 CAN BE SET ARBITRARILY). PROCESSING 1: WITH A POSITION COMMAND TYPE OPERATION UNIT, THERE IS THE NEED FOR THE J/S POSITION AND SCOPE POTENTIOMETER POSITION TO BE OPERATED IN A 1-TO-1 RELATION. ACCORDINGLY, PROCESSING 1: J/S IS MANUALLY MOVED, SO AS TO MATCH THE CURRENT POSITION OF THE SCOPE POTENTIOMETER. PROCESSING ENDS UPON MATCHING. PROCESSING 2: MOTOR IS OPERATED UNTIL SCOPE POTENTIOMETER POSITION MATCHES CURRENT POSITION OF J/S, AND UPON MATCHING, ACTIONS ARE STOPPED, AND THE PROCESSING ENDS. |
| | SOFTWARE DOWNLOADS | DOWNLOADING CAN BE PERFORMED ONLY IN CASES OF THE SOFTWARE (+ PARAMETERS) BEING STORED IN SRAM CARD (PCMCIA), COPIED TO FLASH MEMORY OF CONTROL DEVICE, AND CONTROL DEVICE SET IN DOWNLOAD ENABLED STATE. (IN DOWNLOAD DISABLED STATE, SRAM CARD IS USED FOR COLLECTING LOGS OF THE SYSTEM). |

FIG.9

| ABNORMALITY PROCESSING (TASKS) | ERROR LEVEL | ABNORMALITY PROCESSING (TASKS) | ERROR LEVEL |
|---|---|---|---|
| 1. SOFTWARE | | 2. HARDWARE (INTERLOCKING) | |
| (1) SYSTEM CONTROL (Sysmgr) | | (1) DRIVE SYSTEM MALFUNCTION | |
| NMI MAIN MONITORING | EMERGENCY STOP | MOTOR AMP ABNORMALITY | EMERGENCY STOP |
| OS CALL ERROR | EMERGENCY STOP | CURRENT EXCESS | SAME AS ABOVE |
| INITIALIZATION ERROR | EMERGENCY STOP | VOLTAGE EXCESS | SAME AS ABOVE |
| NET ERROR | EMERGENCY STOP | MOTOR TEMPERATURE ABNORMALITY | SAME AS ABOVE |
| ERROR MESSAGES FROM TASKS | EMERGENCY STOP | (2) AWS | |
| EXEMPTION ABNORMALITY (OS) | EMERGENCY STOP | AIR FEED ABNORMALITY | EMERGENCY STOP |
| NO SRAM CARD | EMERGENCY STOP | WATER FEED ABNORMALITY | SAME AS ABOVE |
| SRAM CARD WRITE-PROTECTED | EMERGENCY STOP | SUCTION ABNORMALITY | SAME AS ABOVE |
| SRAM BATTERY EMPTY | EMERGENCY STOP | (3) SENSOR SYSTEM ABNORMALITY | |
| SRAM BATTERY ALMOST EMPTY | EMERGENCY STOP | ENCODER ABNORMALITY | EMERGENCY STOP |
| MUTUAL MONITORING ERROR (MAIN MONITORING CP) | EMERGENCY STOP | LINE BREAKAGE | SAME AS ABOVE |
| | | SHORT-CIRCUIT | SAME AS ABOVE |
| (2) OPERATION INPUT UNIT (Inpmgr) | | PHASE DETECTION ERROR | SAME AS ABOVE |
| COMMUNICATION ERROR | CUT-OFF STOP | POTENTIOMETER ABNORMALITY | SAME AS ABOVE |
| PARITY ERROR | CUT-OFF STOP | LINE BREAKAGE | SAME AS ABOVE |
| CHECKSUM ERROR | CUT-OFF STOP | SHORT-CIRCUIT | SAME AS ABOVE |
| RECEPTION TIMEOUT | CUT-OFF STOP | TENSION SENSOR ABNORMALITY | SAME AS ABOVE |
| INITIALIZATION ERROR | CUT-OFF STOP | LINE BREAKAGE | SAME AS ABOVE |
| J/S HARDWARE ABNORMALITY | EMERGENCY STOP | SHORT-CIRCUIT | SAME AS ABOVE |
| (3) MCL CONTROL (MclMgr) | | (4) CPU | |
| ACCELERATION DETECTION | WARNING | WDT MAIN | EMERGENCY STOP |
| SPEED DETECTION | WARNING | WDT MONITORING | SAME AS ABOVE |
| INPUT INSTRUCTION LIMIT | CUT-OFF STOP | SERVO-READY ABNORMALITY | SAME AS ABOVE |
| SCOPE INSTRUCTION LIMIT | CUT-OFF STOP | RAS (5 V) | SAME AS ABOVE |
| (4) Timctl | | RAS (3.3 V) | SAME AS ABOVE |
| DEVIATION ABNORMALITY | WARNING | (5) OTHERS | |
| DIRECTION ABNORMALITY (POSITIVE/NEGATIVE) | EMERGENCY STOP | EMERGENCY STOP | SAME AS ABOVE |
| TEMPORARY EXCESSIVE DEVIATION ABNORMALITY | EMERGENCY STOP | SYSTEM READY | SAME AS ABOVE |
| SERVO DELAY ABNORMALITY | EMERGENCY STOP | | |
| MUTUAL MONITORING ERROR (MAIN MONITORING CPU) | EMERGENCY STOP | | |
| HARDWARE INTERLOCKING | EMERGENCY STOP | | |

FIG.14A

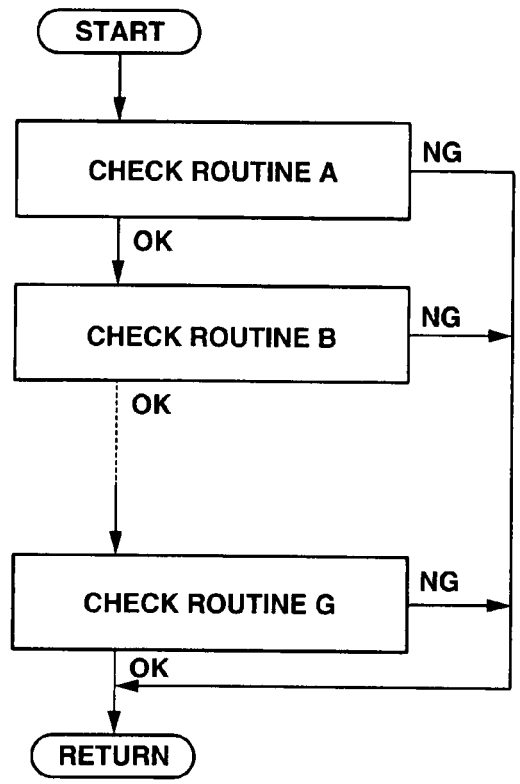

FIG.14B

| CHECK ROUTINE | CHECKING PROCESSING |
|---|---|
| A | CHECK IF NOT OPERATING AT INOPERABLE TIME |
| B | CHECK IF SAME SENSOR VALUE MATCHES BETWEEN MAIN AND MONITORING |
| C | CHECK RELATION BETWEEN ENCODER VALUE AND POTENTIOMETER VALUE |
| D | CHECK WHETHER J/S SERIAL DATA AND POST-CONVERSION DATA MATCH |
| E | CHECK RELATION BETWEEN INPUT SOURCE AND MOTOR COMMAND VALUE (MCLMGR) |
| F | CHECK RELATION OF MOTOR INSTRUCTION VALUES BETWEEN MCLMGR AND TIMCTL |
| G | CHECK RELATION BETWEEN MOTOR INSTRUCTION VALUE AND ENCODER VALUE |

FIG.16A

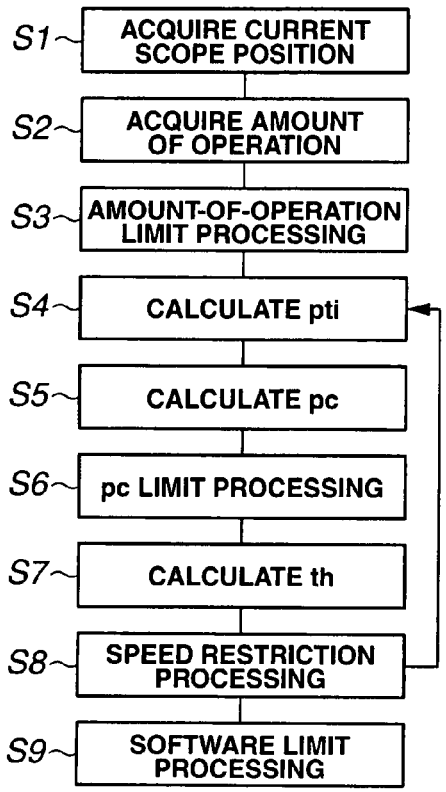

- S1: ACQUIRE CURRENT SCOPE POSITION
- S2: ACQUIRE AMOUNT OF OPERATION
- S3: AMOUNT-OF-OPERATION LIMIT PROCESSING
- S4: CALCULATE pti
- S5: CALCULATE pc
- S6: pc LIMIT PROCESSING
- S7: CALCULATE th
- S8: SPEED RESTRICTION PROCESSING
- S9: SOFTWARE LIMIT PROCESSING

FIG.16C

| NAME OF VARIABLE | NAME |
|---|---|
| p | CURRENT POSITION OF SCOPE UNIT POSITION |
| pre_p | PREVIOUS POSITION OF SCOPE UNIT POSITION |
| m | AMOUNT OF OPERATION |
| pti | VALUE OBTAINED BY MULTIPLYING AMOUNT OF OPERATION BY SENSITIVITY |
| pre_pti | PREVIOUS VALUE OBTAINED BY MULTIPLYING AMOUNT OF OPERATION BY SENSITIVITY |
| pc | COMMAND VALUE OF SCOPE UNIT POSITION |
| pre_pc | PREVIOUS COMMAND VALUE OF SCOPE UNIT POSITION |
| th | COMMAND VALUE OF MOTOR |
| pre_th | PREVIOUS COMMAND VALUE OF MOTOR |
| K | SENSITIVITY |
| Kp | AMOUNT OF OPERATION→POTENTIOMETER VOLTAGE CONVERSION COEFFICIENT |
| Kth | POTENTIOMETER VOLTAGE→MOTOR INSTRUCTION VALUE CONVERSION COEFFICIENT |

FIG.16B

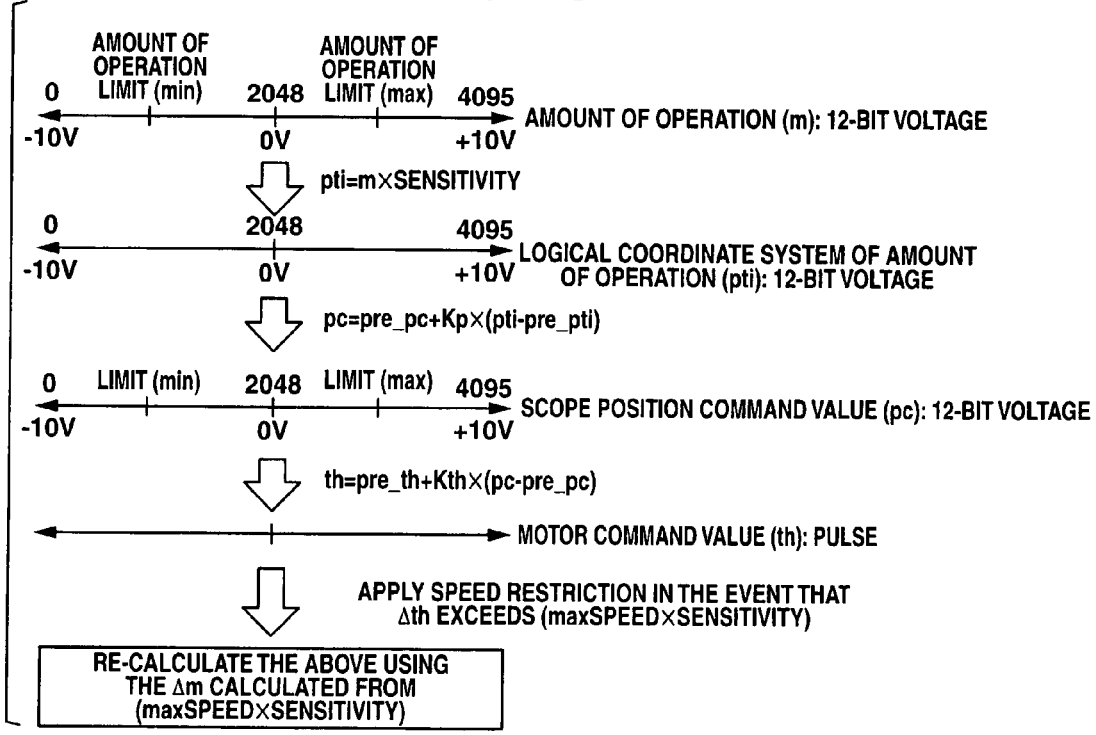

ELECTRICALLY-OPERATED CURVING CONTROL DEVICE

CROSS REFERENCE TO RELATED APPLICATION

This application is a continuation application of PCT/JP2005/015069 filed on Aug. 18, 2005 and claims benefit of Japanese Application No. 2004-239906 filed in Japan on Aug. 19, 2004, the entire contents of which are incorporated herein by this reference.

BACKGROUND OF THE INVENTION

1. Field of the Invention

The present invention relates to an electrically-operated curving control device which electrically drives curving of a curving portion provided to an insertion portion of an endoscope.

2. Description of the Related Art

In recent years, endoscopes are widely used which can observe body organs in a body cavity by inserting a slender insertion portion into the body cavity, and also performing various types of treatment using treatment equipment inserted through a treatment equipment channel as necessary.

Such an endoscope generally has a curving portion which curves in the vertical/horizontal directions provided at the tip side thereof, and the curving portion can be curved in a desired direction by pulling/relaxing operations of curving wires connected to the curving portion.

The aforementioned curving wires have generally been operated manually, but as of recent, an electrically-operated curving endoscope device whereby pulling operations are performed using electrical curving driving means such as electric motors or the like is disclosed in, for example, Japanese Unexamined Patent Application Publication No. 2003-245246. This first conventional example is a configuration for facilitating calibration work.

Also, a second conventional example in Unexamined Patent Application Publication No. 6-217925 discloses an electrically-operated curving endoscope device wherein motor torque is appropriately set.

An object of the present invention is to provide an electrically-operated curving control device capable of monitoring the state relating to curving actions.

Also, it is an object of the present invention to provide an electrically-operated curving control device capable of speedily handling abnormality in the case of an abnormal state occurring relating to curving actions.

SUMMARY OF THE INVENTION

The present invention is an electrically-operated curving control device which comprises curving driving control means for performing electrical curving driving control of a curving portion of an endoscope, and monitoring means for monitoring the state of electrically performing curving driving control of the curving portion.

BRIEF DESCRIPTION OF THE DRAWINGS

FIGS. 3A and 3B are diagrams illustrating a configuration example of an operation input unit.

FIG. 4 is a block diagram illustrating the flow of data in a case of communication being performed between the curving control device and an HMI (PC).

FIG. 7 is a table illustrating the various types of functions of the curving control device and the contents thereof.

FIG. 8 is a table illustrating contents such as parameter changing, system monitoring, and so forth, performed by the curving control device.

FIG. 9 is a table illustrating items for abnormality processing by the curving control device.

FIGS. 14A and 14B are diagrams illustrating multiple check routines for performing error monitoring, and the check contents thereof.

FIGS. 16A, 16B and 16C are diagrams illustrating processing and the like up to generating pulse command values in a case of operating a joystick.

FIG. 26 is an explanatory diagram illustrating processing operations in the event that an emergency stop error has occurred which cannot be recovered from.

FIG. 27 is an explanatory diagram illustrating processing operations in the event that a cut-off stop error has occurred which can be recovered from.

DETAILED DESCRIPTION OF THE PREFERRED EMBODIMENT(S)

The embodiments according to the present invention will be described below with reference to the diagrams.

First Embodiment

Figure 1:
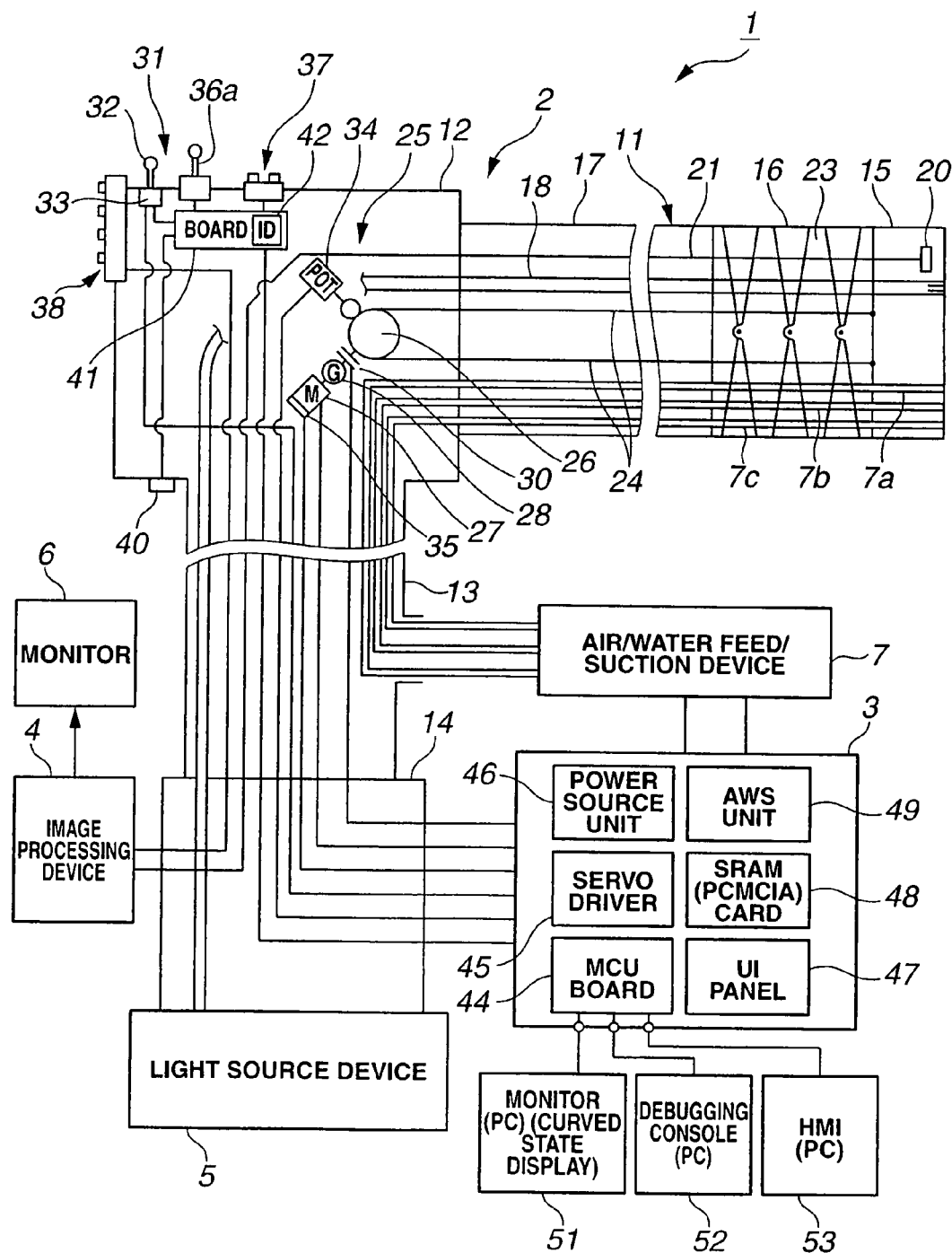
FIG. 1 is a diagram illustrating the overall configuration of an electrically-operated curving endoscope system having a curving control device according to a first embodiment of the present invention.
Figure 2:
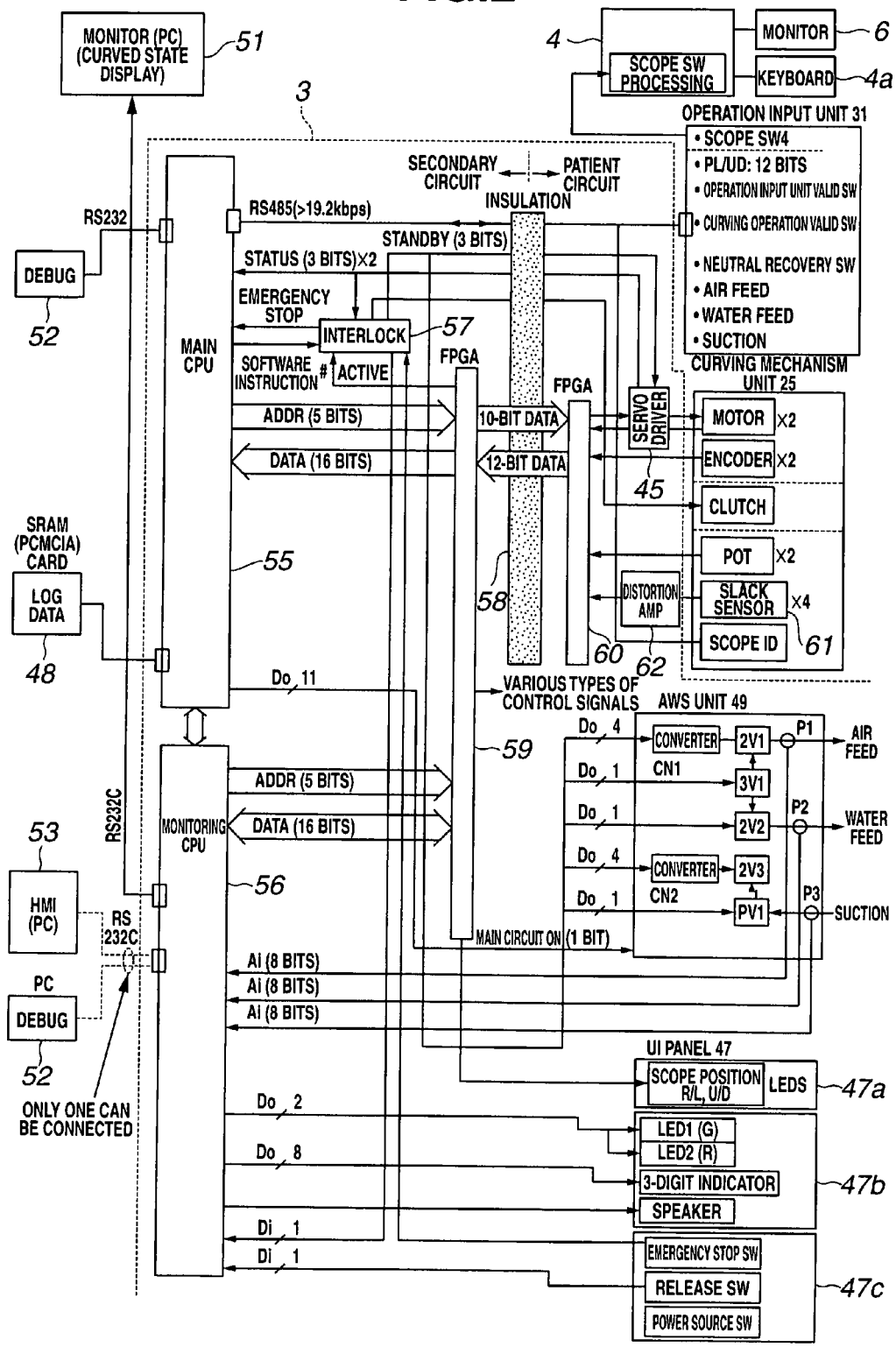
FIG. 2 is a diagram illustrating the hardware configuration of the curving control device according to the first embodiment of the present invention.
Figure 5A:
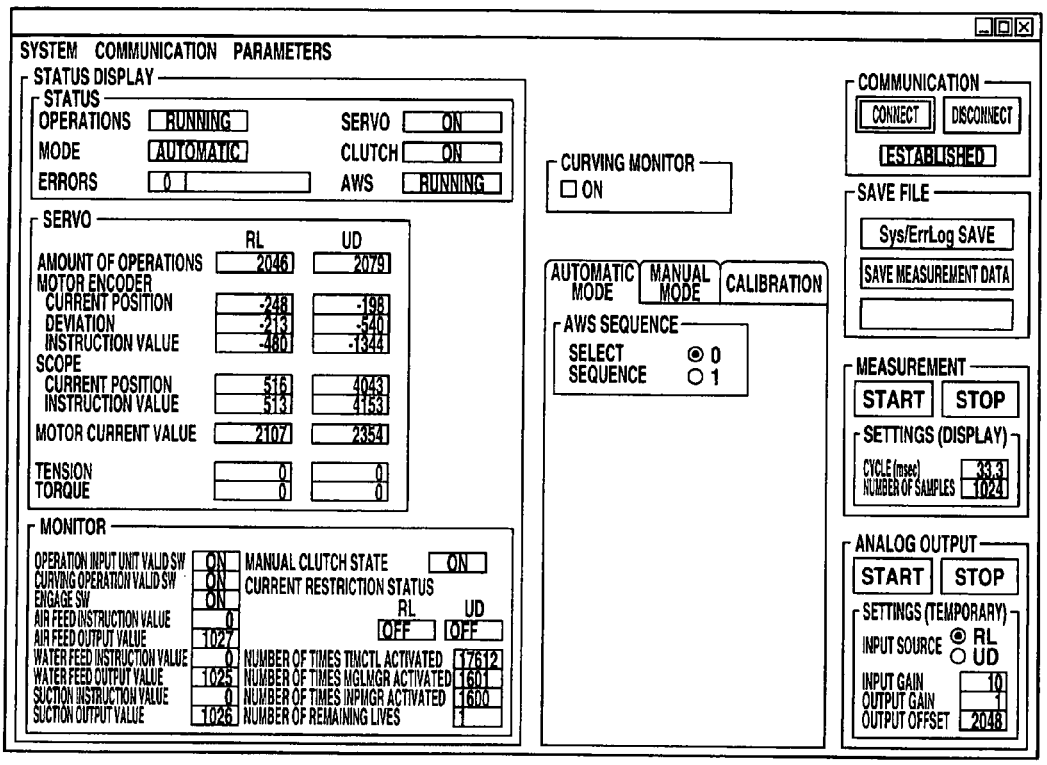
FIGS. 5A and 5B are diagrams illustrating an example of a display screen of the HMI (PC).
Figure 5B:
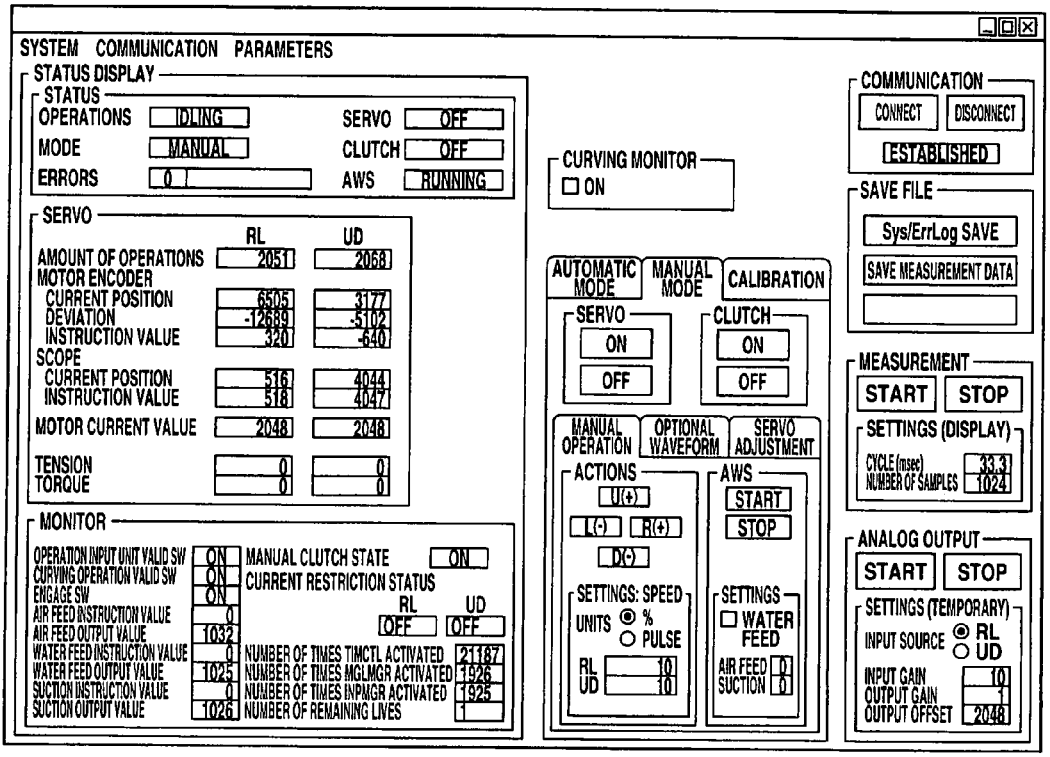
Figure 6:
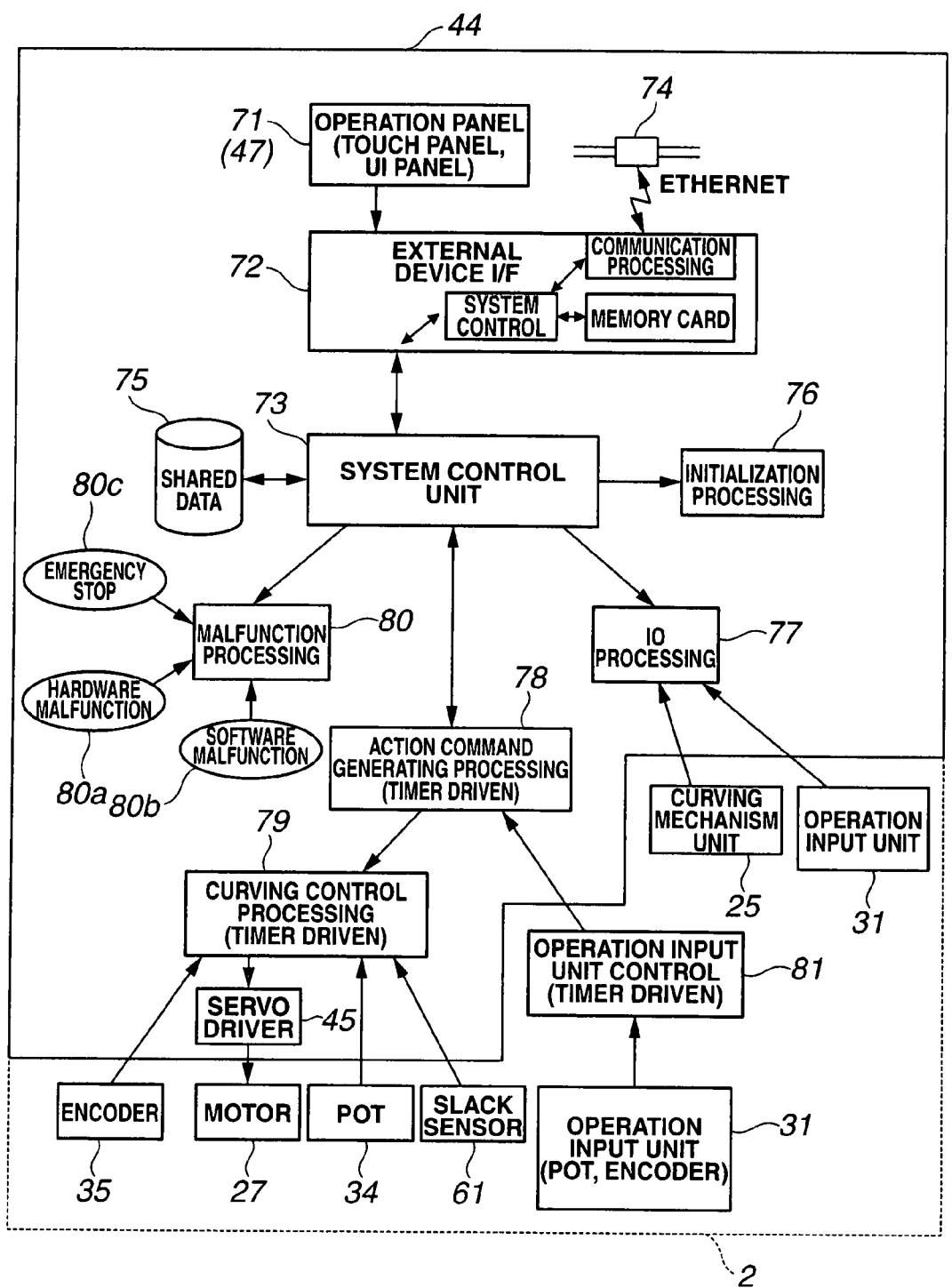
FIG. 6 is an explanatory diagram illustrating control processing functions relating to curving control by an MCU board of the curving control device.

FIG. 1 through FIG. 35 relate to a first embodiment of the present invention, wherein FIG. 1 illustrates the overall configuration of an electrically-operated curving endoscope system having a curving control device (hereafter simplified "electrically-operated curving control device" as "curving control device") according to a first embodiment of the present invention; FIG. 2 illustrates the hardware configuration of the curving control device according to the first embodiment of the present invention; FIGS. 3A and 3B illustrate a configuration example of an operation input unit; FIG. 4 illustrates the flow of data in a case of communication being performed between the curving control device and an HMI (PC); FIGS. 5A and 5B illustrate an example of a display screen of the HMI (PC); FIG. 6 illustrates control processing functions relating to curving control by an MCU board of the curving control device.

Figure 10:
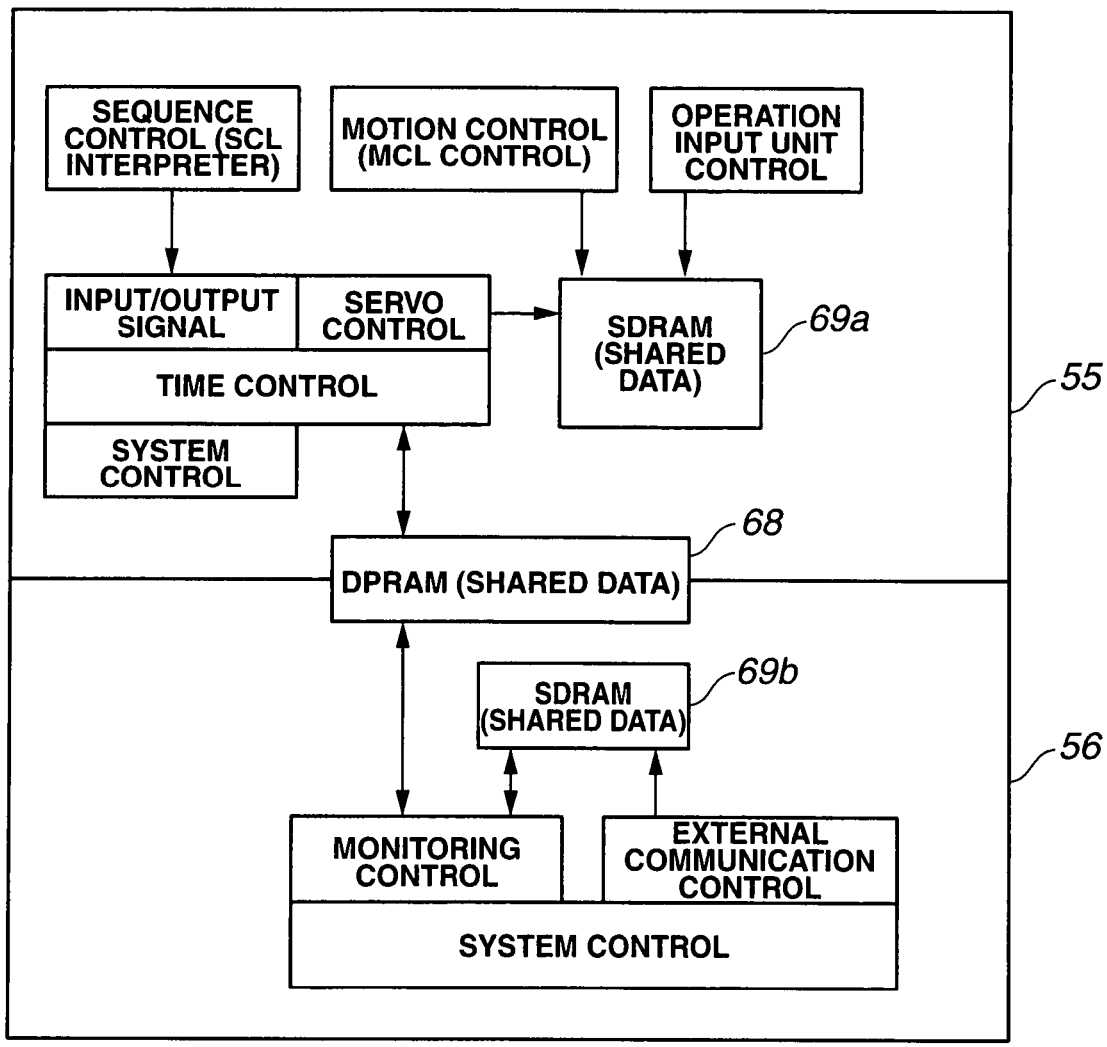
FIG. 10 is an explanatory diagram illustrating the processing functions of a system control unit shown in FIG. 6, with regard to the relation between a main CPU side and monitoring CPU side.
Figure 11A:
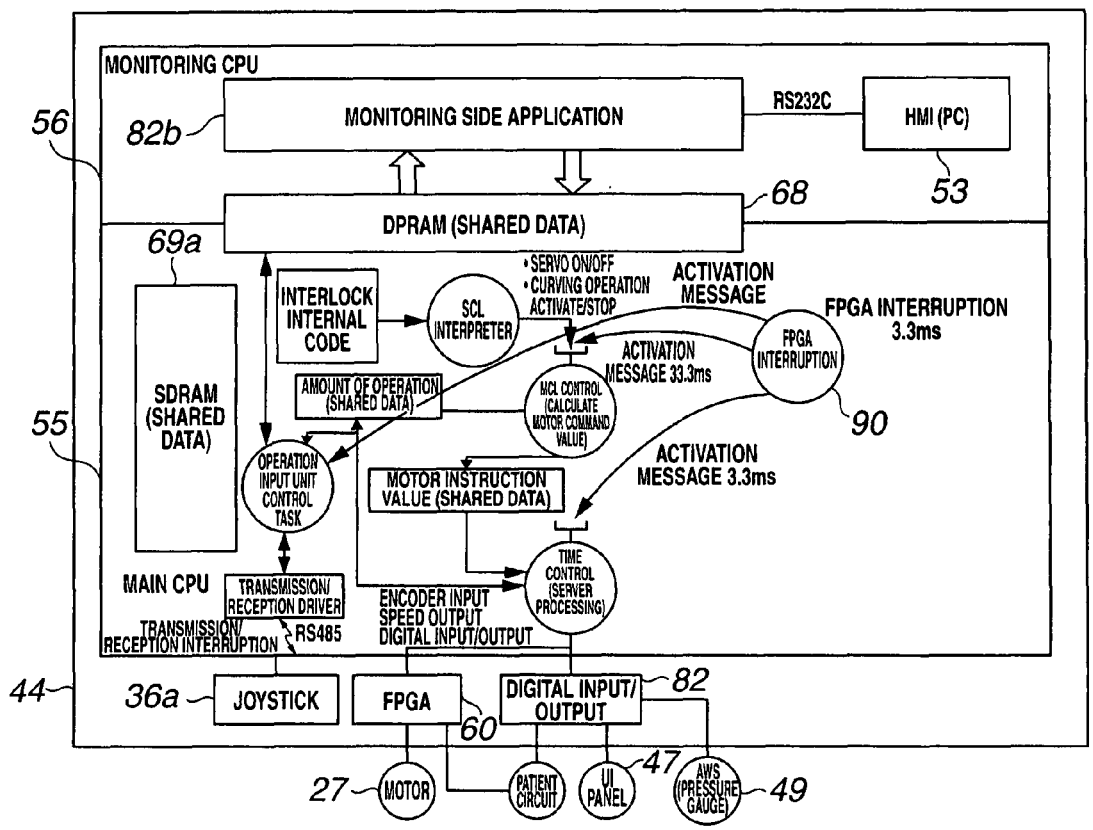
FIGS. 11A and 11B are explanatory diagrams specifically illustrating the processing functions shown in FIG. 10, divided into the main CPU side and the monitoring CPU side.
Figure 11B:
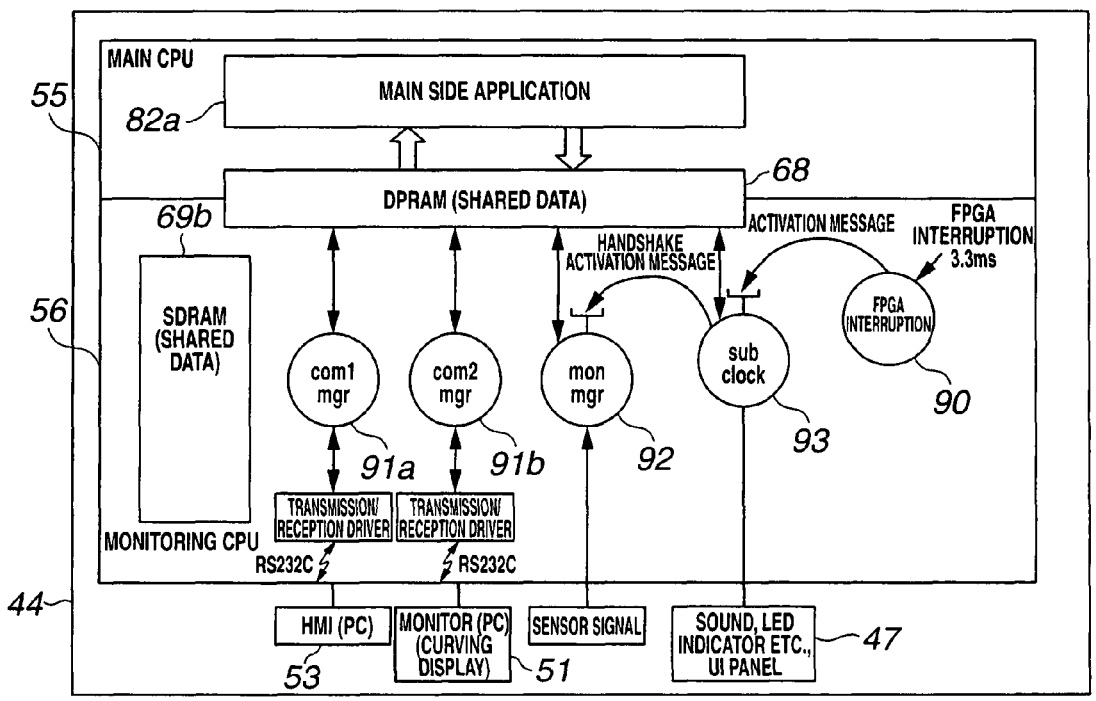
Figure 12A:
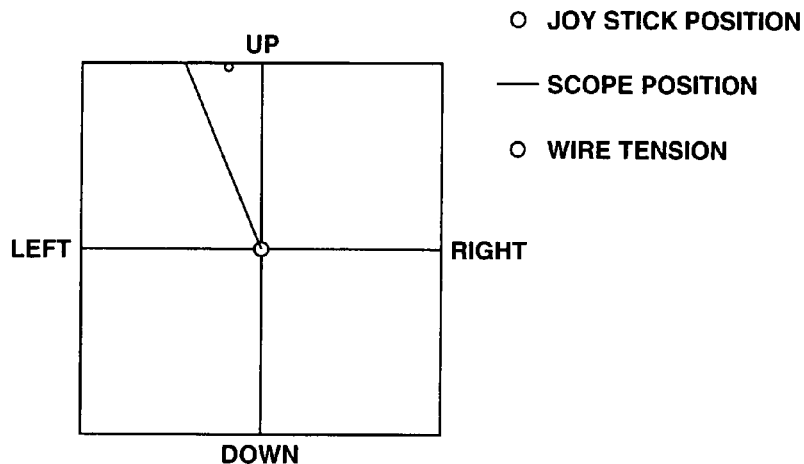
FIGS. 12A and 12B are diagrams illustrating a display example of a curved state on a monitor (PC) and an example of a display screen in a calibration mode on an HMI (PC).
Figure 12B:
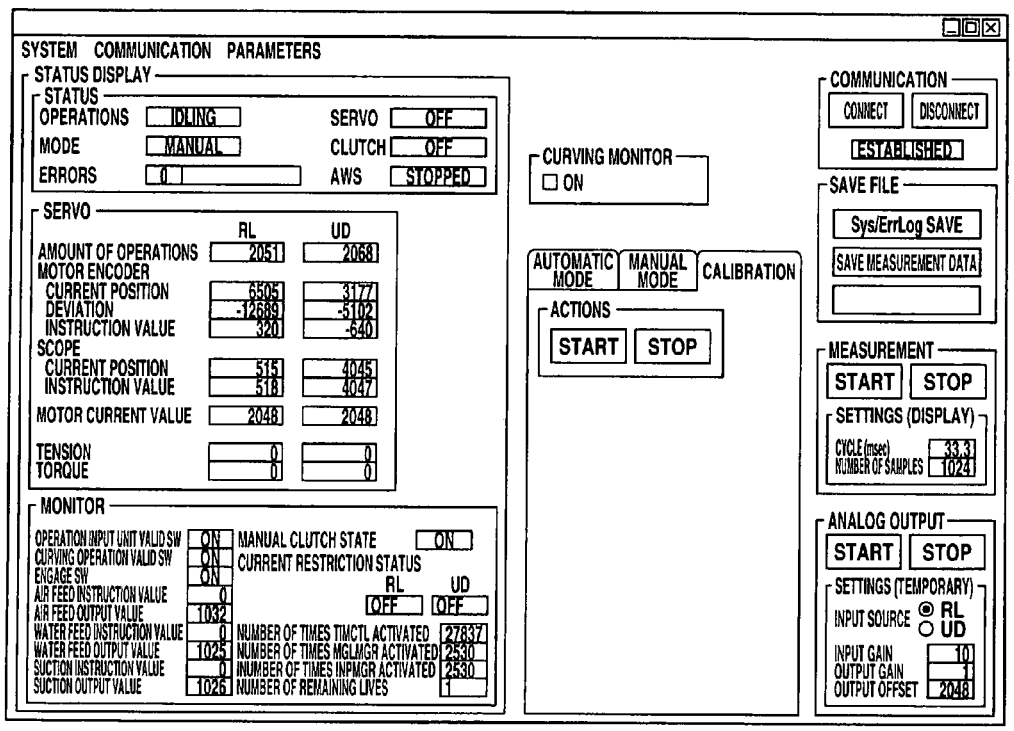

FIG. 7 illustrates the various types of functions of the curving control device and the contents thereof; FIG. 8 illustrates contents such as parameter changing, system monitoring, and so forth, performed by the curving control device; FIG. 9 illustrates items for abnormality processing with the curving control device; FIG. 10 is an explanatory diagram illustrating the processing functions of a system control unit shown in FIG. 6, with regard to the relation between a main CPU side and monitoring CPU side; FIGS. 11A and 11B specifically illustrate the processing functions shown in FIG. 10, divided into the main CPU side and the monitoring CPU side; FIGS. 12A and 12B illustrate a display example of a curved state on a monitor (PC) and an example of a display screen in a calibration mode on an HMI (PC).

Figure 13:
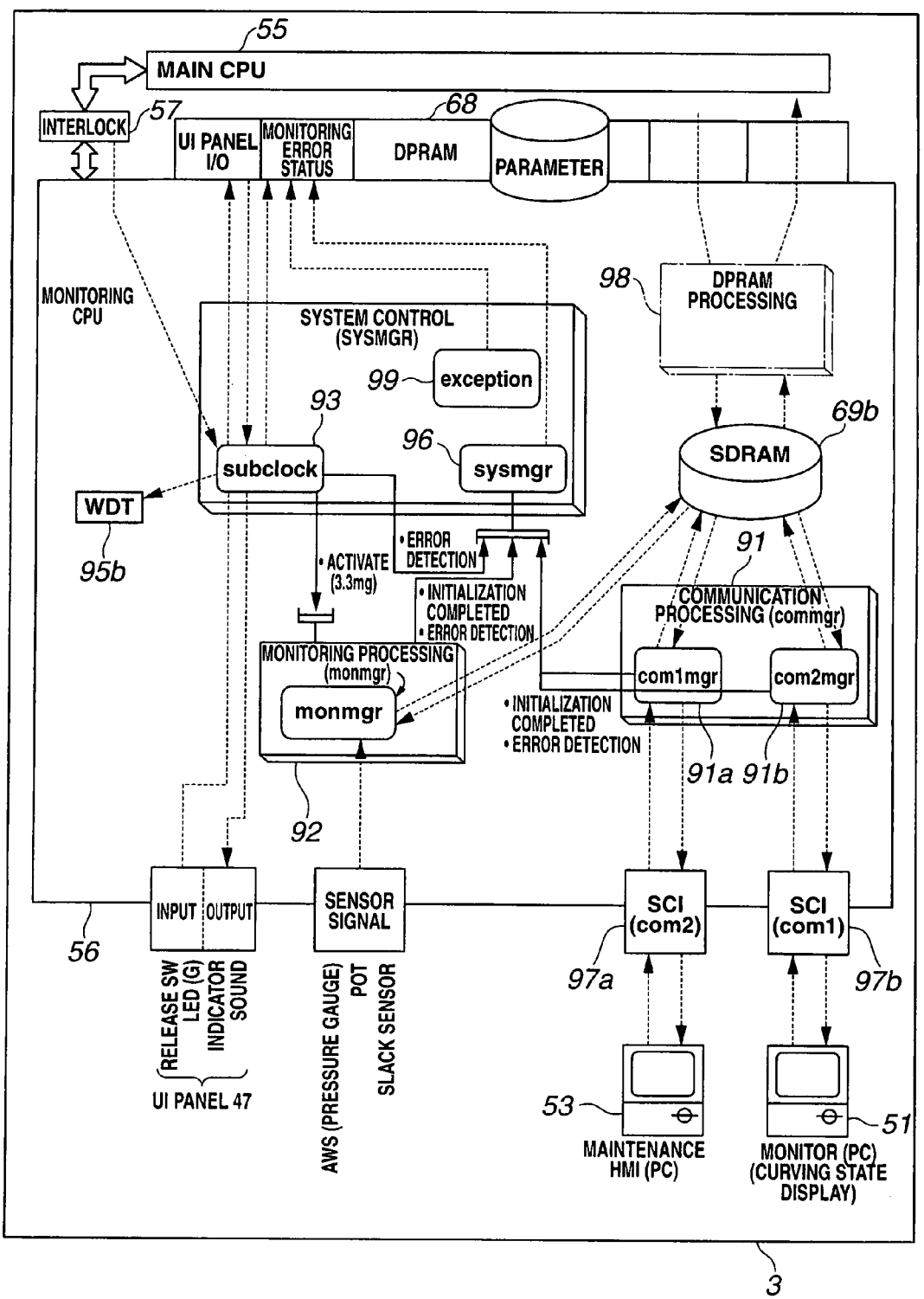
FIG. 13 is an explanatory diagram illustrating processing functions in FIG. 11B more specifically.
Figure 15:
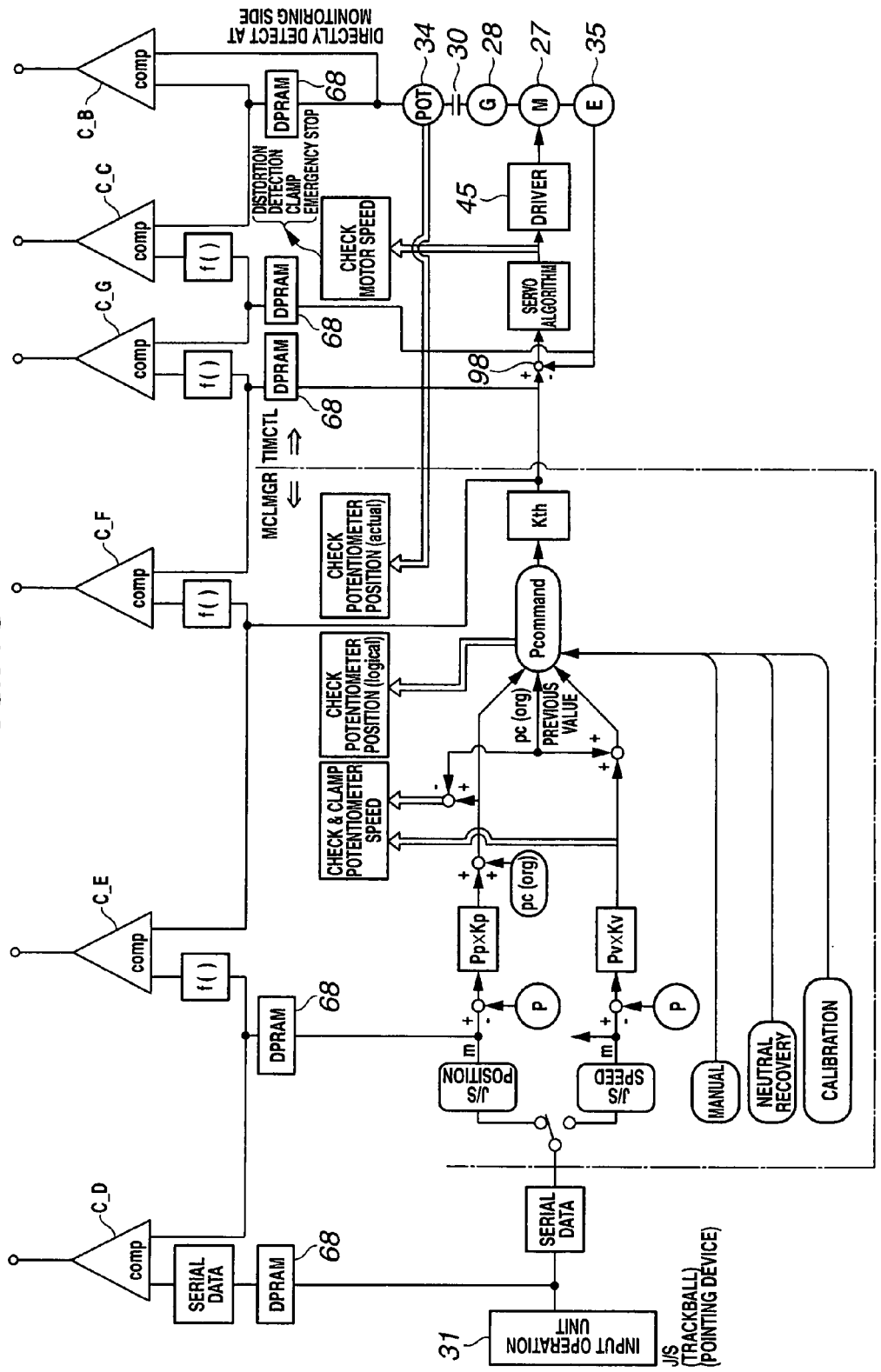
FIG. 15 is a diagram illustrating the configuration in a case of performing the error monitoring in FIG. 14A by way of hardware.
Figure 17A:
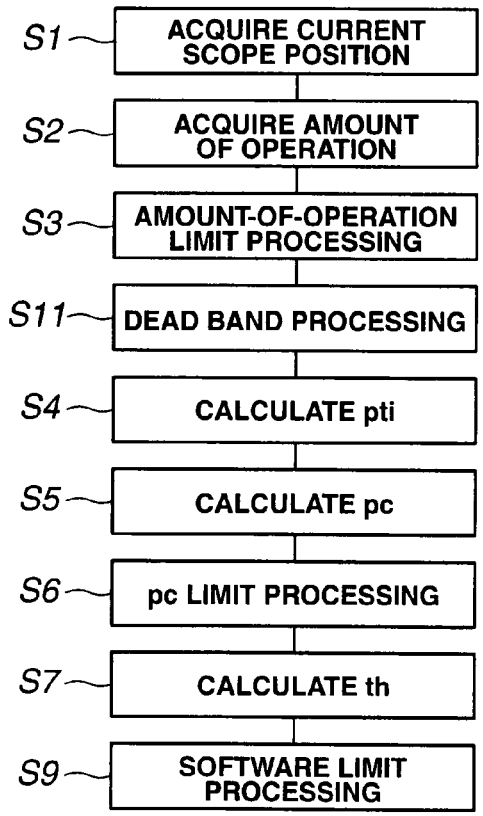
FIGS. 17A and 17B are diagrams illustrating processing and the like up to generating pulse command values in a case of operating a pointing device.
Figure 17B:
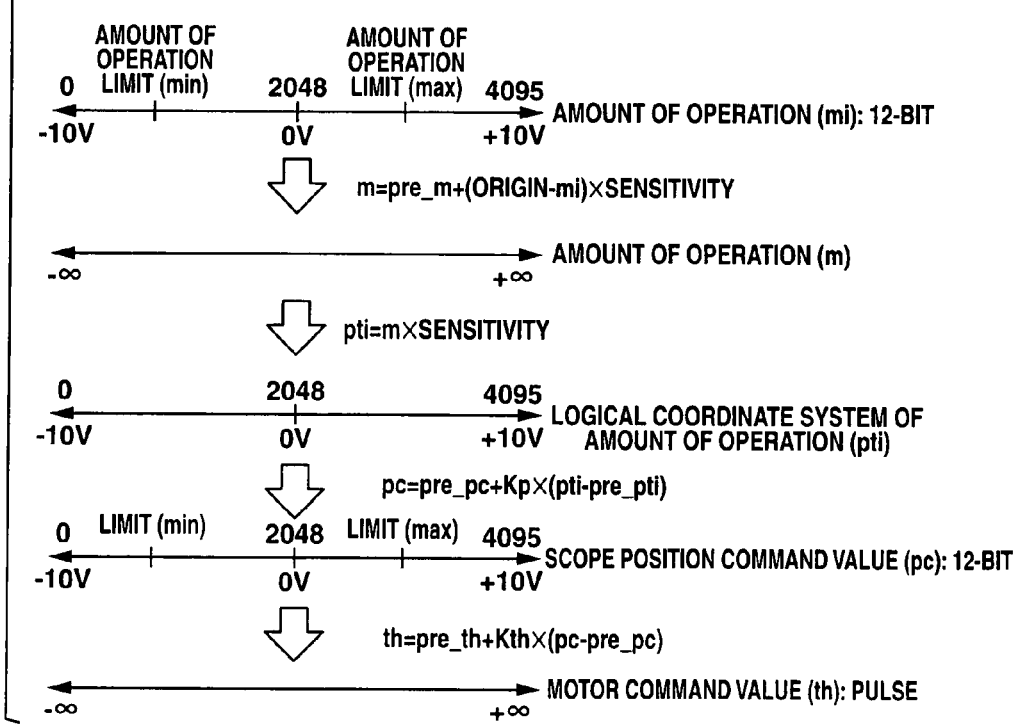
Figure 18A:
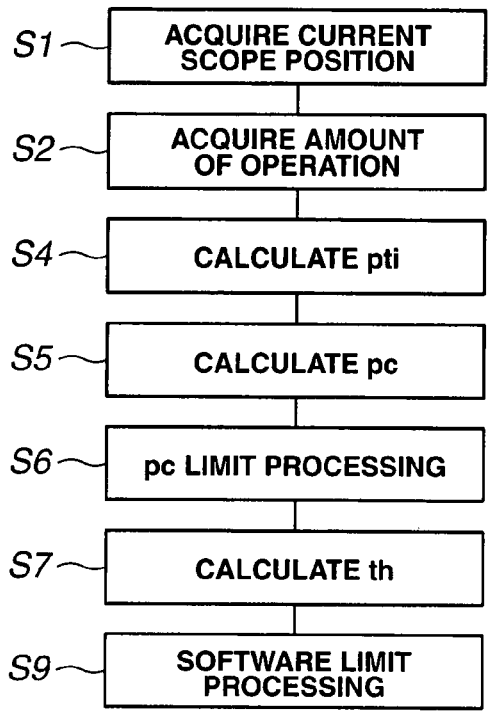
FIGS. 18A and 18B are diagrams illustrating processing and the like up to generating pulse command values in a case of operating a trackball.
Figure 18B:
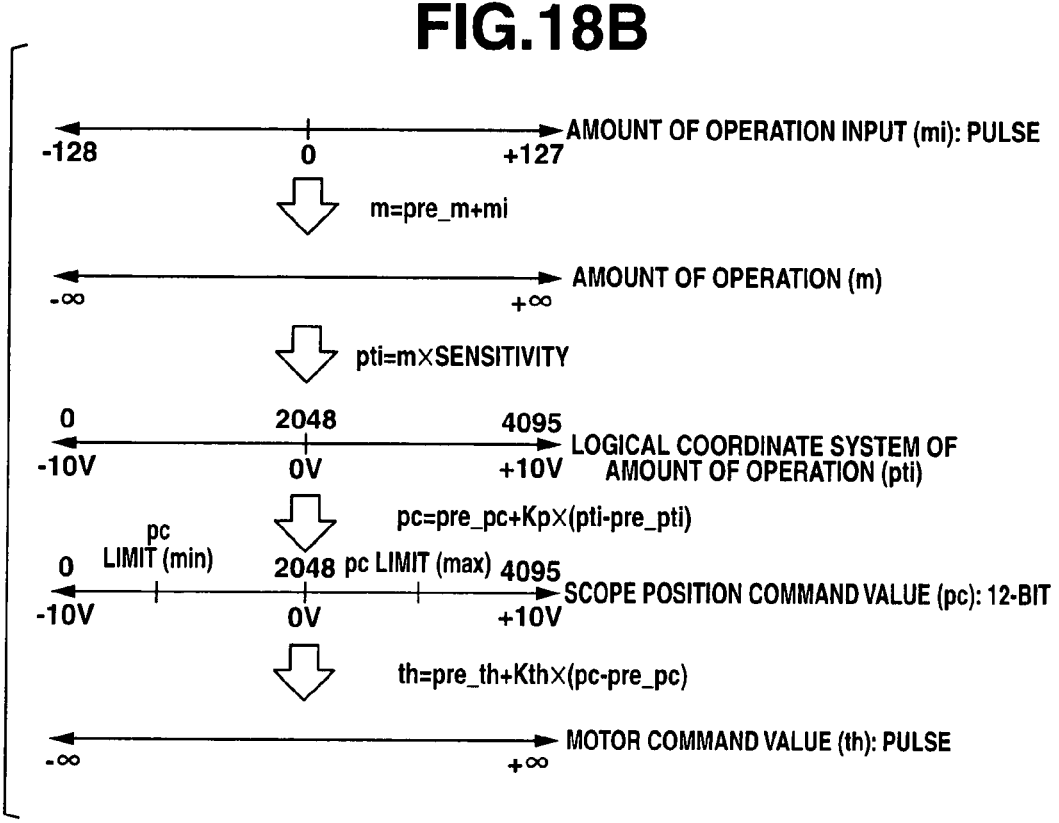

FIG. 13 illustrates processing functions in FIG. 11B more specifically; FIGS. 14A and 14B illustrate multiple check routines for performing error monitoring, and the check contents thereof; FIG. 15 illustrates the configuration in a case of performing the error monitoring in FIG. 14A by way of hardware; FIGS. 16A, 16B and 16C illustrate processing and the like up to generating pulse command values in a case of operating a joystick; FIGS. 17A and 17B illustrate processing and the like up to generating pulse command values in a case of operating a pointing device; FIGS. 18A and 18B illustrate processing and the like up to generating pulse command values in a case of operating a trackball.

Figure 19:
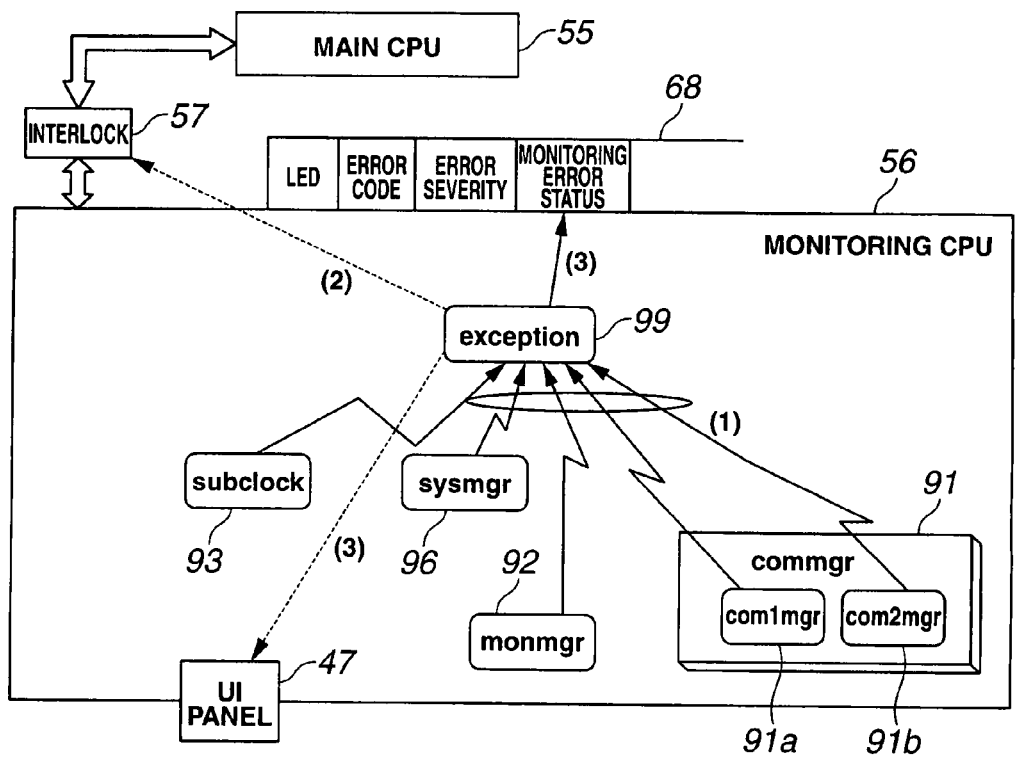
FIG. 19 is an explanatory diagram illustrating processing operations at the time of an exemption occurring.
Figure 20:
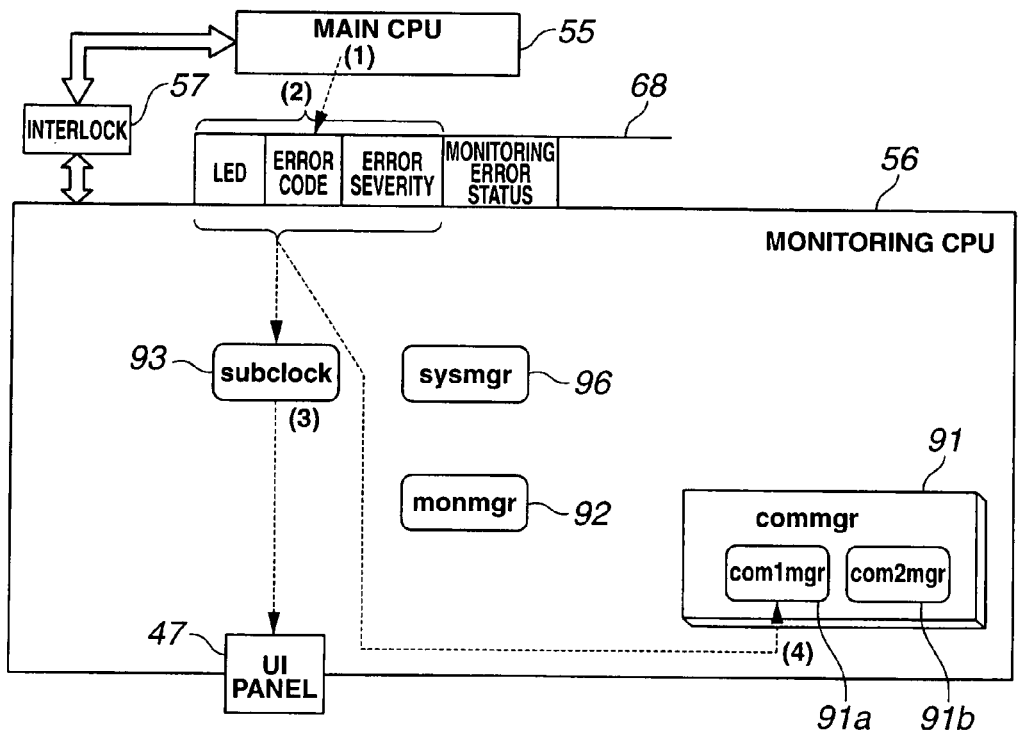
FIG. 20 is an explanatory diagram illustrating processing operations regarding an error occurring at the main CPU side.
Figure 21:
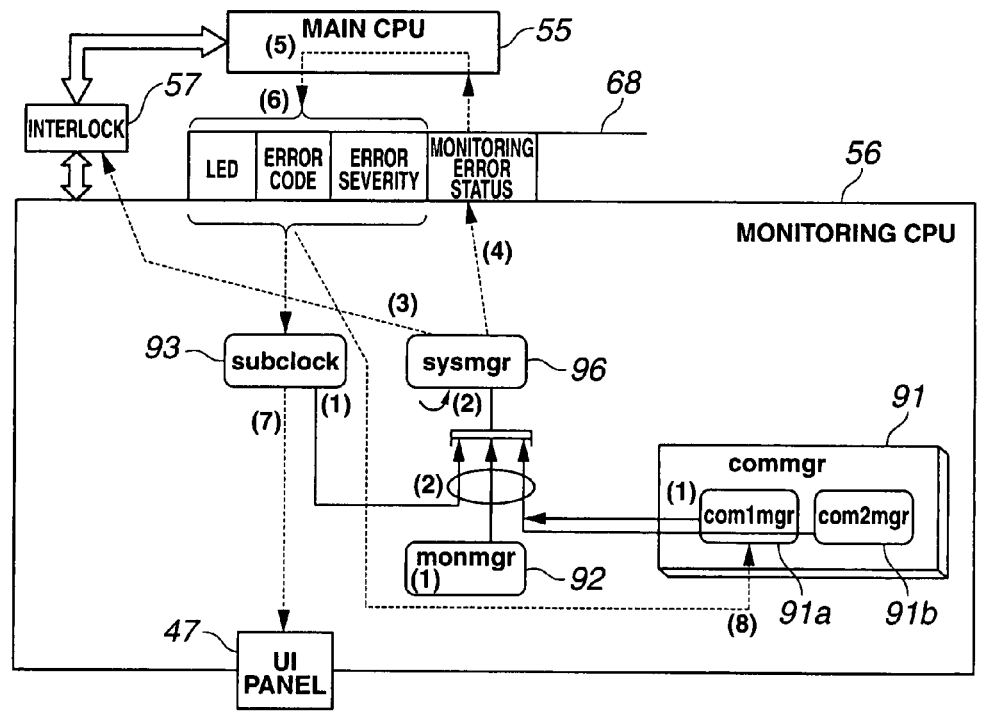
FIG. 21 is an explanatory diagram illustrating processing operations regarding a software error occurring at the monitoring CPU side.
Figure 22:
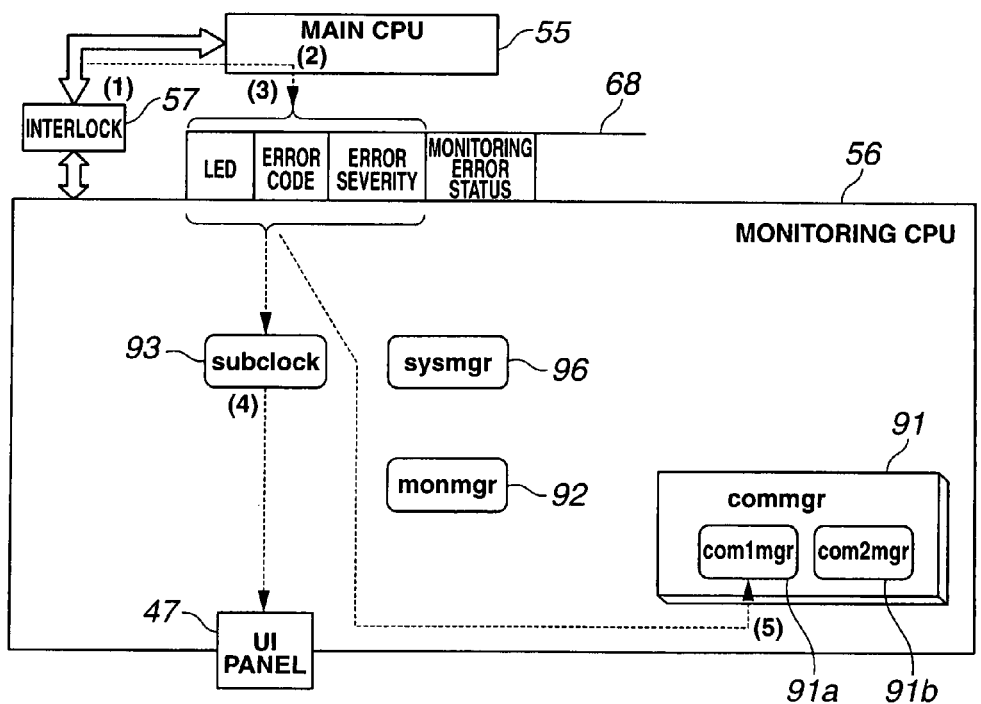
FIG. 22 is an explanatory diagram illustrating processing operations in a case of error detection due to interlocking.
Figure 23:
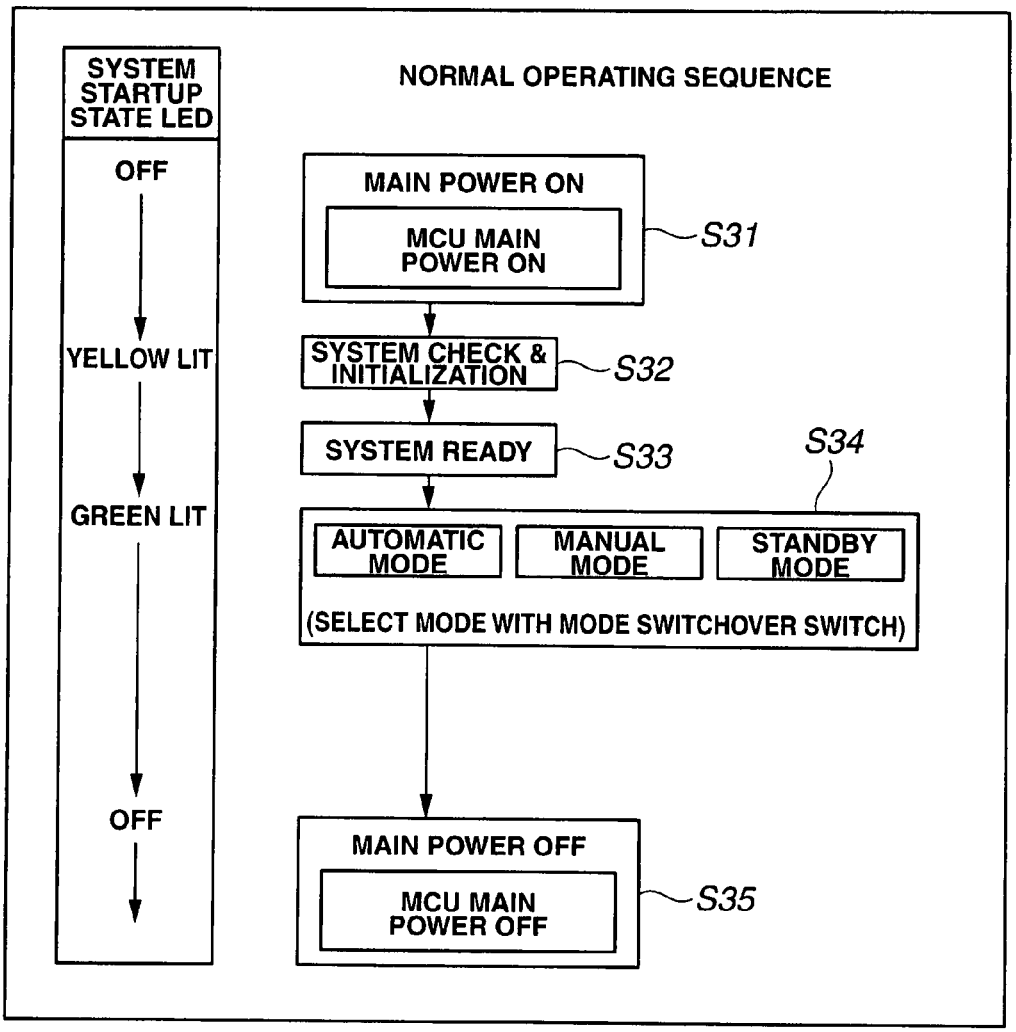
FIG. 23 is a flowchart illustrating a normal operating sequence from startup of the control device to shutdown thereof.
Figure 24:
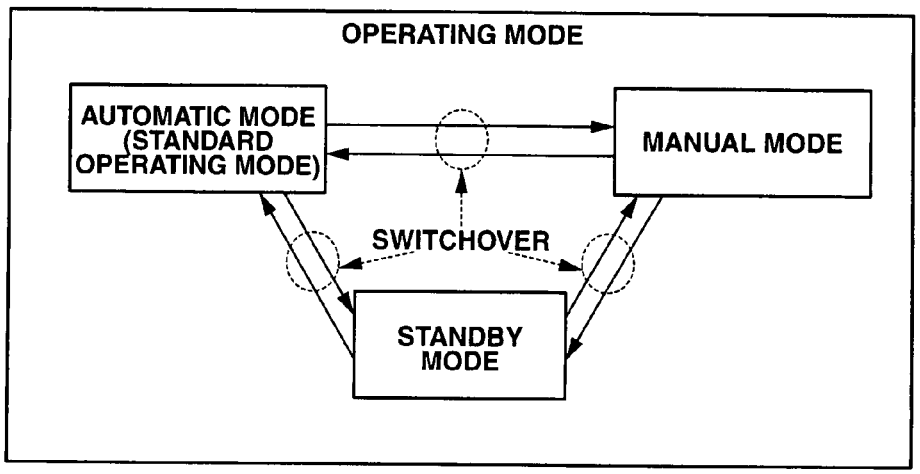
FIG. 24 is an explanatory diagram illustrating that switchover can be performed among the three operating modes shown in FIG. 23.
Figure 25:
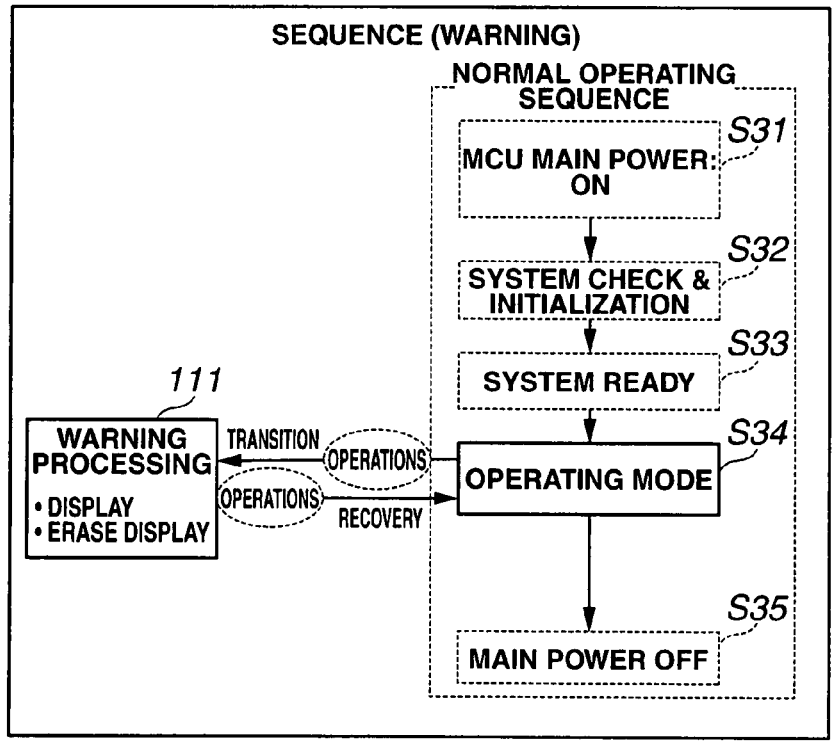
FIG. 25 is an explanatory diagram illustrating processing operations in the event that a warning has occurred in the operating mode.

FIG. 19 illustrates processing operations at the time of an exemption occurring; FIG. 20 illustrates processing operations regarding an error occurring at the main CPU side; FIG. 21 illustrates processing operations regarding an error occurring at the monitoring CPU side; FIG. 22 illustrates processing operations in a case of error detection due to interlocking; FIG. 23 illustrates a normal operating sequence from startup of the control device to shutdown thereof; FIG. 24 illustrates that switchover can be performed among the three operating modes shown in FIG. 23; FIG. 25 illustrates processing operations in the event that a warning has occurred in the operating mode.

Figure 26:
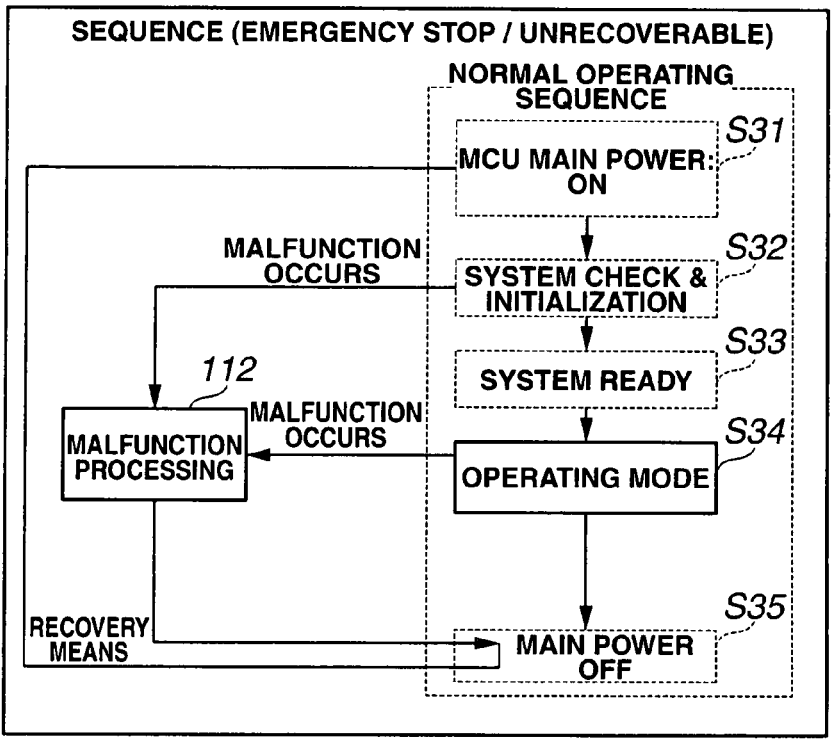
Figure 27:
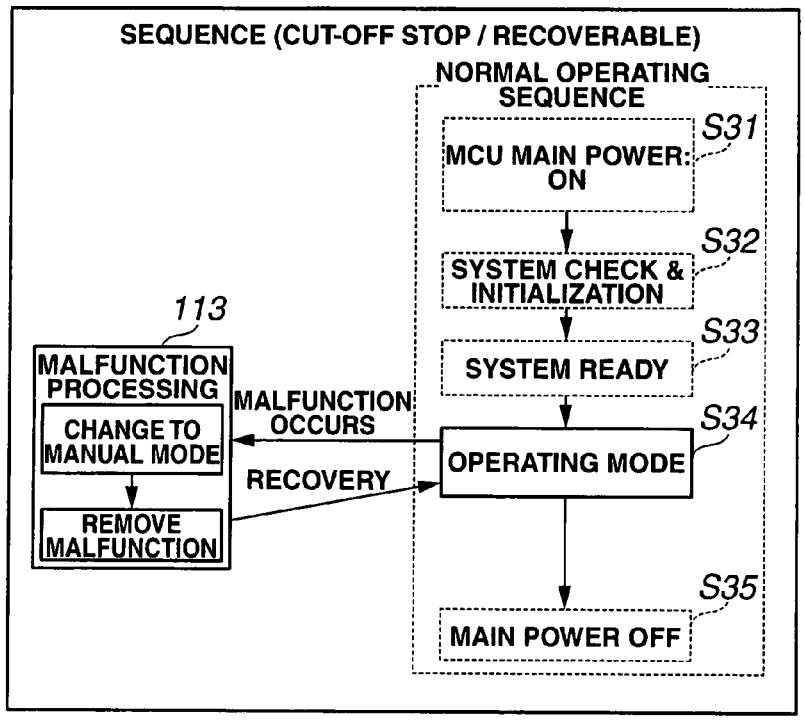
Figure 28:
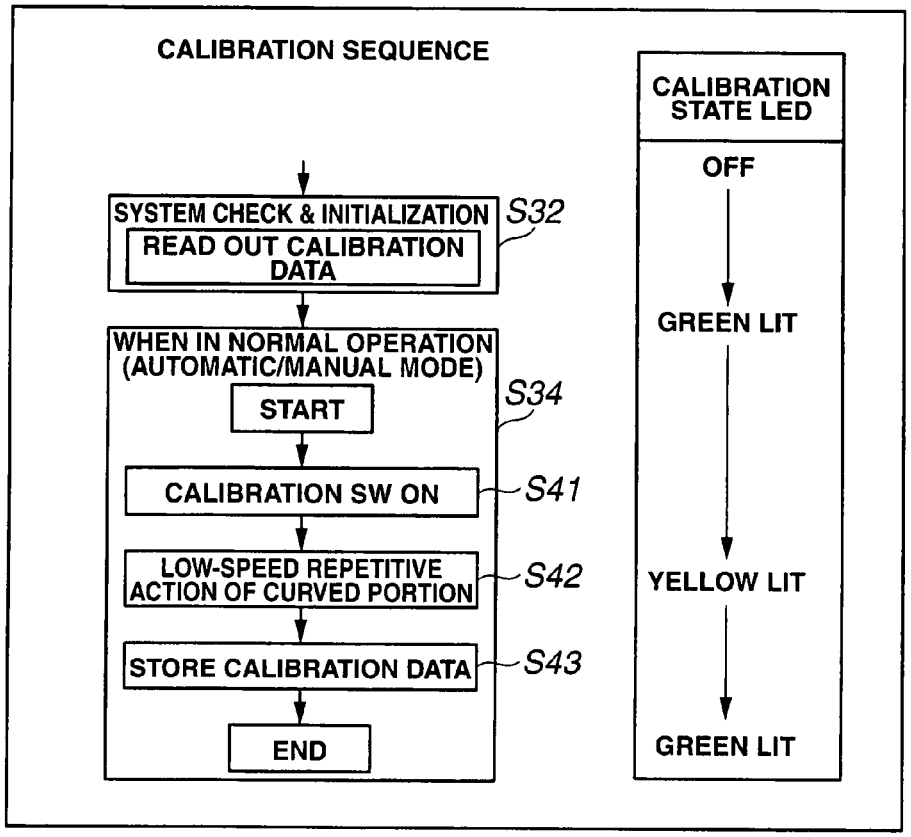
FIG. 28 is a flowchart illustrating processing procedures for calibration.
Figure 29:
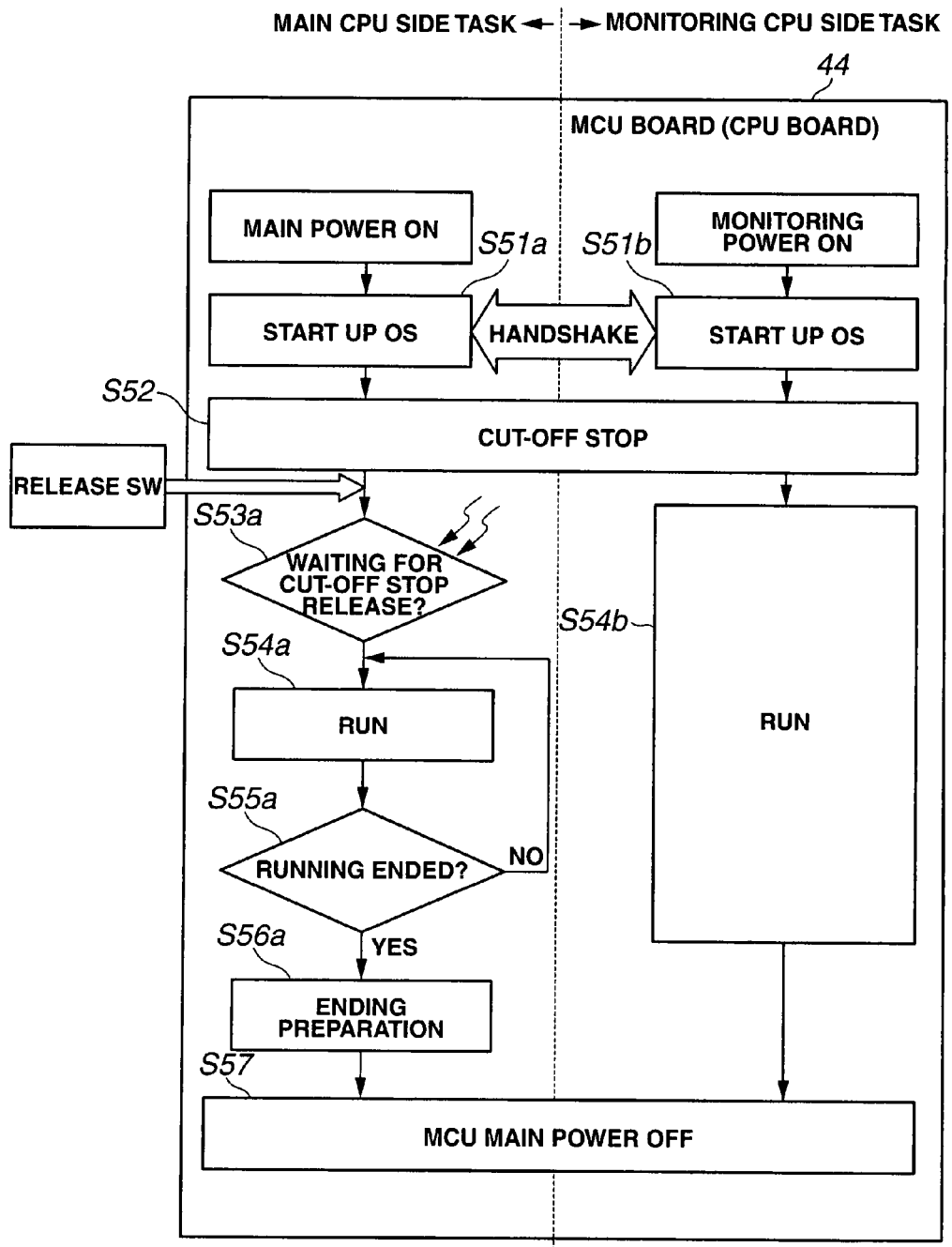
FIG. 29 is a flowchart illustrating the startup and shutdown sequence for the main CPU and monitoring CPU.
Figure 30A:
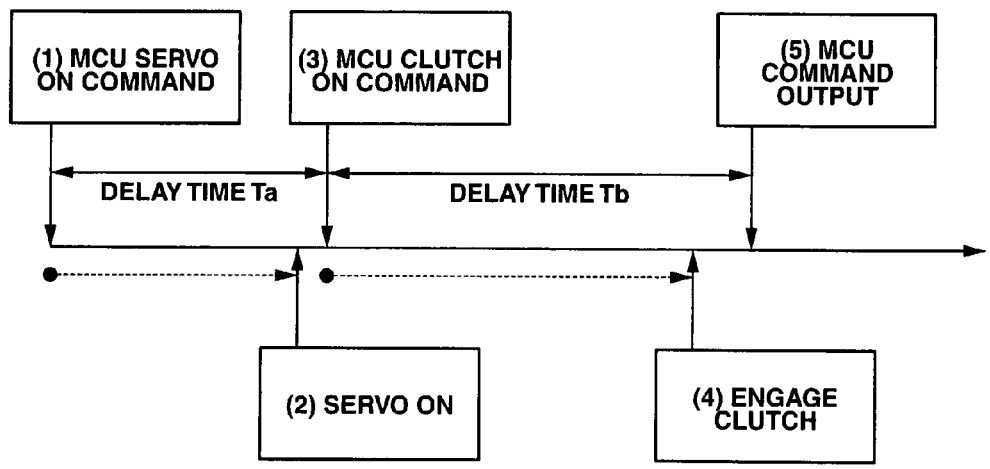
FIGS. 30A and 30B are explanatory diagrams illustrating the actions from the electromagnetic clutch engaging due to a clutch ON command, to disengaging due to a clutch OFF command.
Figure 30B:
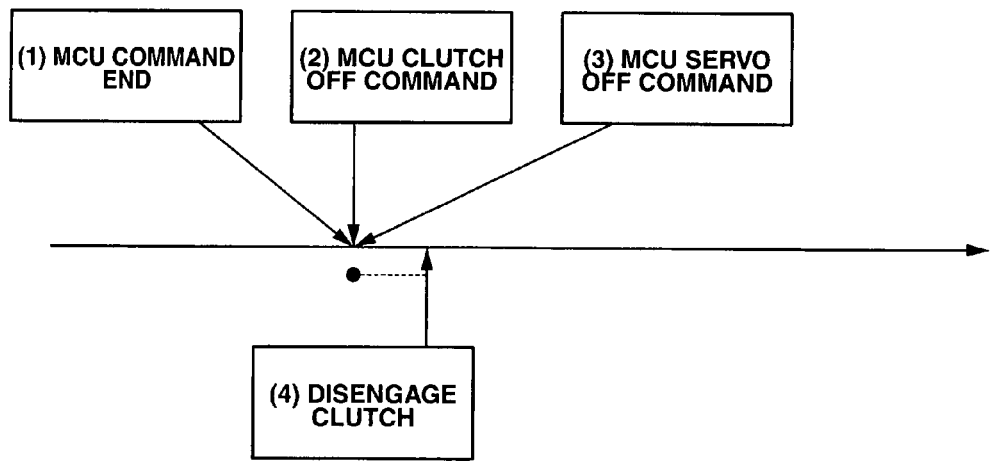

FIG. 26 illustrates processing operations in the event that an emergency stop error has occurred which cannot be recovered from; FIG. 27 illustrates processing operations in the event that a cut-off stop error has occurred which can be recovered from; FIG. 28 illustrates processing procedures for calibration; FIG. 29 illustrates the startup and shutdown sequence for the main CPU and monitoring CPU; FIGS. 30A and 30B illustrate the actions from the clutch engaging due to a clutch ON command, to disengaging due to a clutch OFF command.

Figure 32:
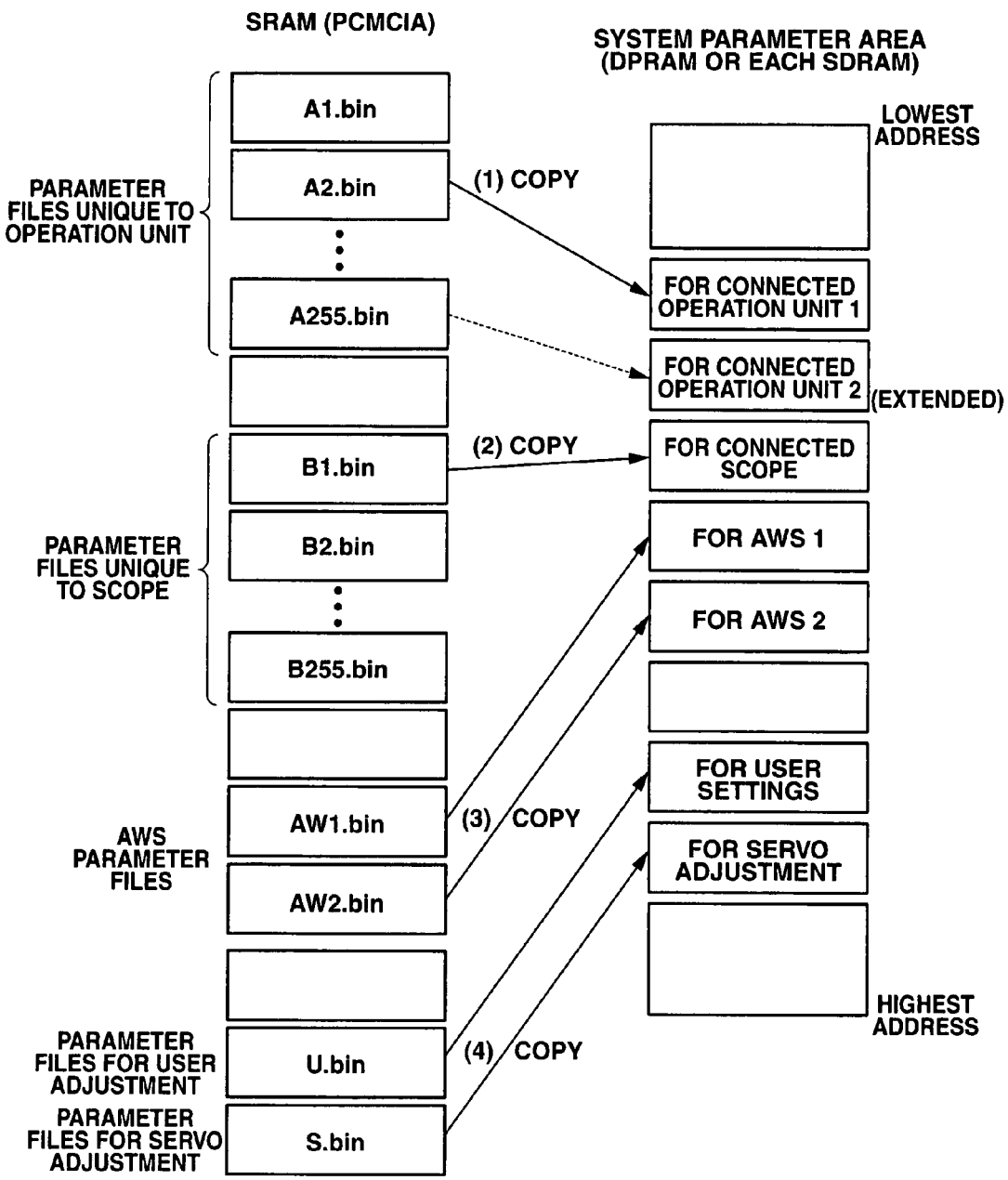
FIG. 32 is a diagram illustrating the various setting parameters stored in a SRAM card, and the way in which copying is performed from the setting parameters to the DPRAM.
Figure 33B:
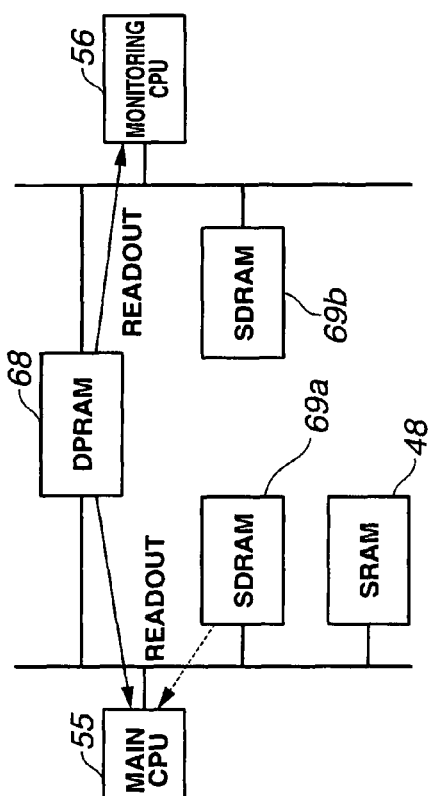
FIGS. 33A to 33D are explanatory diagrams illustrating the actions for each case of rendering dynamic setting parameters stored in a SRAM card, using of the setting parameters following rendering, a change request, and a storage request.
Figure 34:
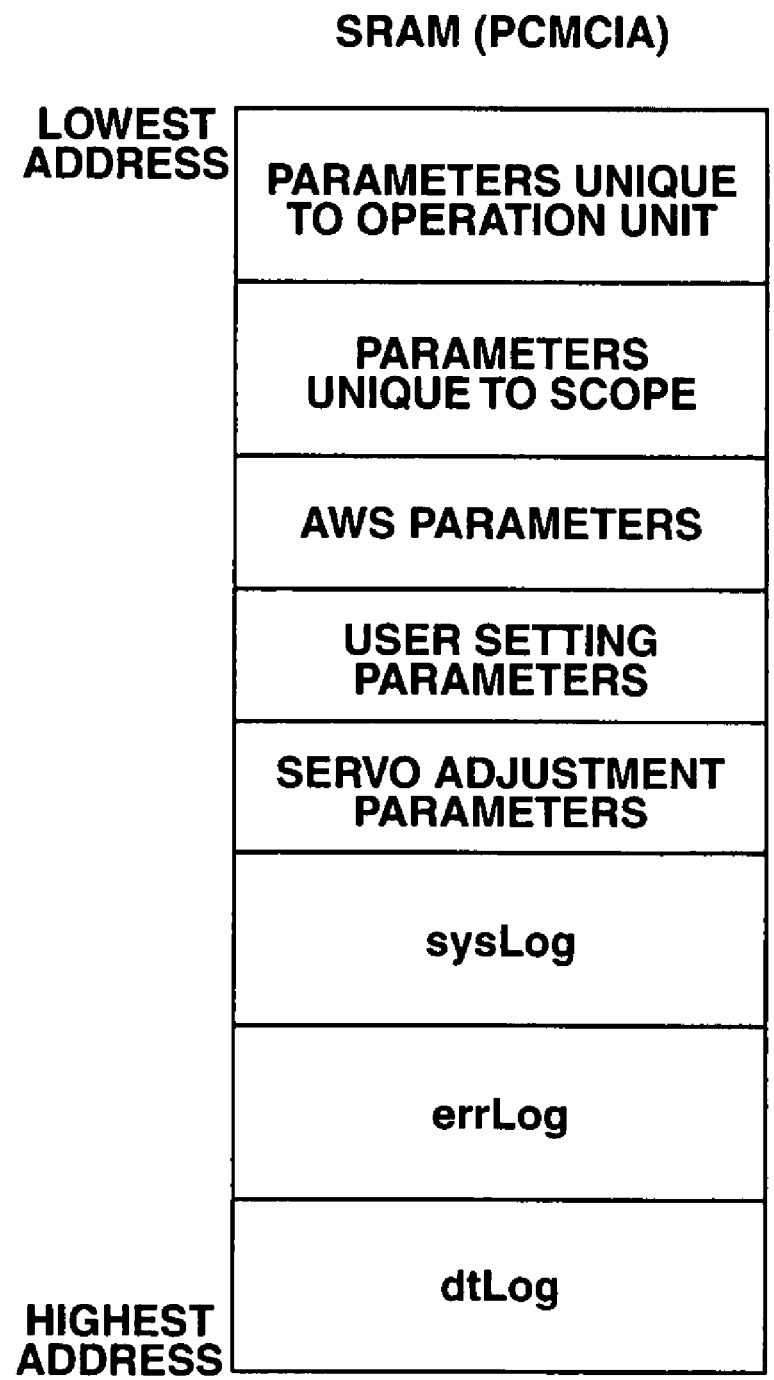
FIG. 34 is a block diagram illustrating setting parameters, such as parameters unique to an operation unit, system logs, and so forth, stored in the SRAM card.
Figure 35:
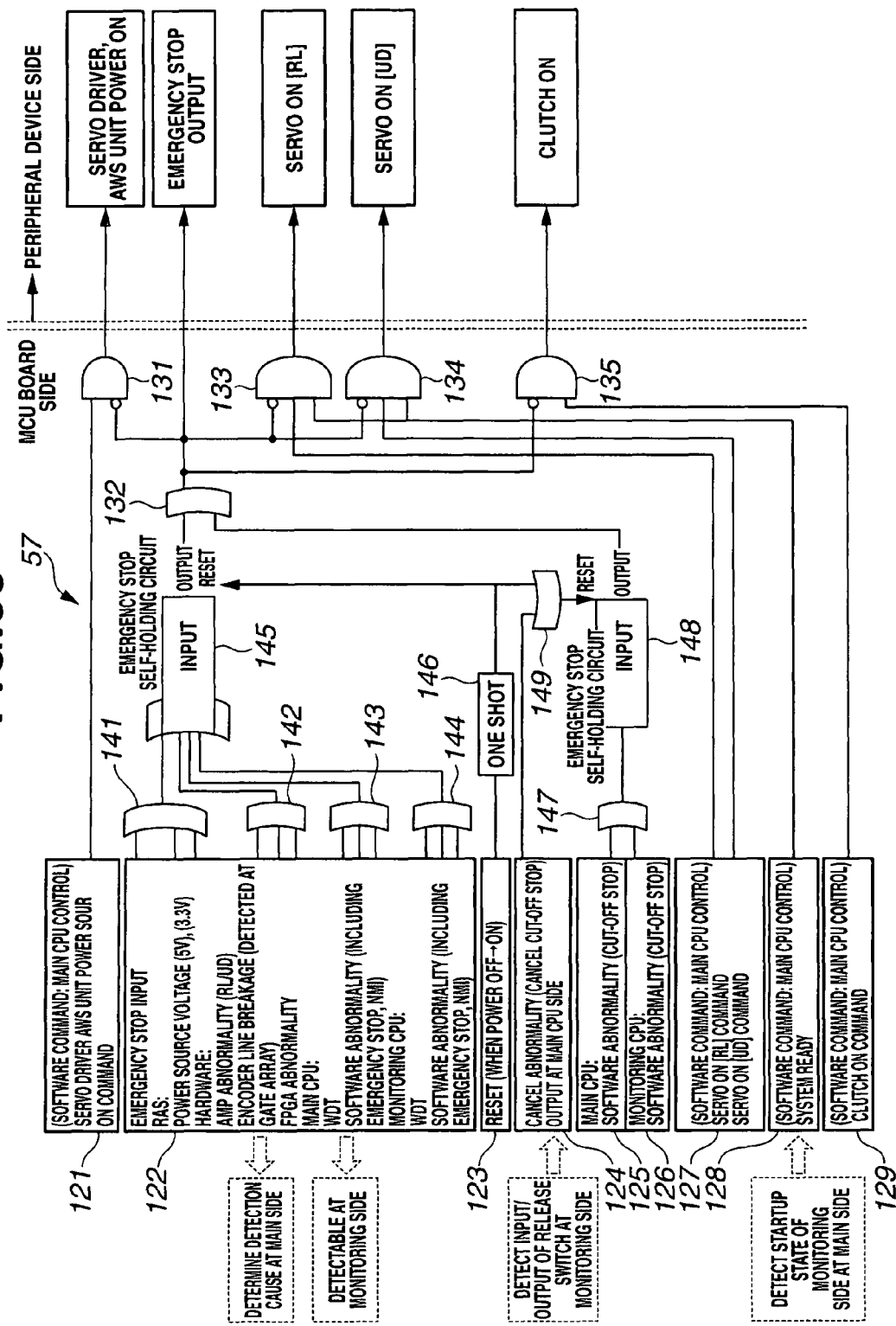
FIG. 35 is a diagram illustrating the detailed configuration of interlocking.

FIGS. 31A to 31D illustrate the actions for each case of rendering static setting parameters stored in a SRAM card, using of the setting parameters following rendering, a change request, and a storage request; FIG. 32 illustrates the various setting parameters stored in a SRAM card, and the way in which copying is performed from the parameters to the DPRAM; FIGS. 33A to 33D illustrate the actions for each case of rendering dynamic setting parameters stored in a SRAM card, using of the setting parameters following rendering, a change request, and a storage request; FIG. 34 illustrates setting parameters, such as parameters unique to an operation unit, system logs, and so forth, stored in the SRAM card; FIG. 35 illustrates the detailed configuration of interlocking.

As shown in FIG. 1, an electrically-controlled curving endoscope system 1 primarily comprises an electrically-controlled curving endoscope (abbreviated as endoscope, or as scope) 2 of which curving driving is performed electrically, a curving control device 3 of the first embodiment which is detachably connected to the endoscope 2 and which performs curving control of the endoscope 2, an image processing device 4 for performing signal processing as to an image-capturing device 20 built in to the endoscope 2, a light source device 5 for supplying illumination light to the endoscope 2, a monitor 6 for displaying an endoscope image corresponding to the inputted video signal which is generated by the image processing device 4, and an air/water feed/suction device 7 for performing control of an air feed tube 7a and so forth of the endoscope 2.

The endoscope 2 has a flexible slender insertion portion 11, an operation unit 12 provided on the rear end of the insertion portion 11, and a universal cord 13 extending from the side portion of the operation unit 12, wherein a connector portion 14 on the end portion of the universal cord 13 is detachably connected to the light source device 5.

The insertion portion 11 has a rigid tip rigid portion 15, a curvable curving portion 16 provided on the rear end of the tip rigid portion 15, and a flexible tube portion 17 extending from the rear end of the curving portion 16 to the front end of the operation unit 12.

A light guide fiber 18 for transmitting illumination light is inserted into the insertion portion 11, and by the rear end side of this light guide fiber 18 being inserted into the universal cord 13 and the connector portion 14 being connected to the light source device 5, illumination light is supplied to the light guide fiber 18 from an unshown lamp within the light source device 5.

The illumination light transmitted by the light guide fiber 18 is emitted externally from the tip face fixed to the illumination window on the tip rigid portion 15, and illuminates the subject such as organs within the body cavity. The illuminated subject is image-formed by the image-capturing device 20 disposed in an image-forming position by an unshown objective lens which is attached to an observation window provided adjacent to the illumination window.

The image-capturing device 20 is connected to the image processing device 4 via a signal cable 21.

Also, an air feed tube 7*a*, water feed tube 7*b*, and suction tube 7*c* are inserted into the insertion portion 11, wherein these tubes 7*a*, 7*b*, and 7*c* are connected to the air/water feed/suction device 7. Also, the curving control device 3 and the image processing device 4 are electrically connected via a unshown signal line.

The curving portion 16 is configured with multiple curving pieces 23 consecutively provided so as to be rotatable in the lengthwise direction of the insertion portion 11, the tip of a curving wire 24 for vertical curving which pairs with the tip-most curving piece is fixed, the rear end side of the curving wire 24 is linked to an unshown chain, and this chain meshes with a sprocket 26 configuring a curving mechanism 25 (serving as a curving driving mechanism for electrical curving driving the curving portion 16) which is disposed in the operation unit 12.

Therefore, by the sprocket 26 being rotated in a predetermined direction, one of the curving wires 24 linked to the aforementioned chain is pulled, and the other is relaxed, such that the curving portion 16 is curved in the direction in which the curving wire 24 is pulled.

Note that curving wires for horizontal curving are also inserted within the insertion portion 11, but for simplicity are not shown in the diagram, since the configuration thereof is the same as that of the vertical curving wires 24. The sprocket 26 can be electrically rotatably driven, as described below.

The driving force of a curving motor (abbreviated as motor) 27 made up of a DC motor, for example, serving as an electrical curving driving means, is transmitted to the sprocket 26 via multiple gears 28 and an electromagnetic clutch 30 serving as a driving force transmitting/disconnecting means. Then, when the electromagnetic clutch 30 is in a disconnected state, the curving wires 24 become in a state of having no tension applied thereto, and the curving portion 16 becomes in a freely curving state, curving freely by external force.

The electromagnetic clutch 30 can be switched between a driving force transmitting disconnecting state which is the disconnected state and a driving force transmitting connecting state which is the connected state, by performing switchover operation of a switchover operation lever 32 serving as the state switchover means, which configures an operation input unit 31 provided on the outer surface of the operation unit 12, to the driving force transmitting disconnecting position (hereafter written as curving free instruction position) or the driving force transmitting recovery position (hereafter written as angle operating instruction position).

Here the description is regarding an electromagnetic clutch, but as long as the driving force of the motor 27 does not mechanistically transmit to the curving portion 16 directly, the clutch means is not limited to an electromagnetic clutch.

Rotation amount of the sprocket 26 is detected with a potentiometer 34 (abbreviated as pot in the diagrams) serving as a curving angle detecting means. In other words, with the detecting information of the potentiometer 34, current position information relating to curving actions with the curving mechanism 25 provided within the endoscope 2 can be obtained. With the present embodiment, this position information is also referred to as scope position or scope portion position location.

Also, the rotation amount of the motor 27 is detected with an encoder 35. Also, the motor 27 can be servo controlled using the detecting output of the encoder 35.

A joystick 36*a* serving as operation input means (input command means) for curving operations for curving the curving portion 16, wherein, for example, a potentiometer for a stick outputting a position signal as a curving operation input signal is disposed on the base side, or an air/water feed/suction switch 37 for instructing the air feed state or water feed state or suction state, are provided as an operation input unit 31 provided on the outer surface of the operation unit 12.

Also, as the operation input unit 31, various types of scope switches 38 for performing control of the image processing device 4, such as freezing the endoscope image displayed on the screen on the monitor 6, the switchover operation lever 32 for performing switchover operations of the electromagnetic clutch 30 to the driving force transmitting disconnecting state or the driving force transmitting recovery state, and a state detecting switch 33 serving as state detecting means for detecting whether the switchover operation lever 32 is positioned at the curving free operating instruction position or the angle operating instruction position.

The joystick 36*a* instructs the curving angle of the curving portion 16 by changing the tilt direction and tilt angle when the user performs tilting operations. In other words, the tilt direction of the joy stick 36*a* corresponds to the curving direction of the curving portion 16, and the tilting angle corresponds to the curving angle of the curving portion 16.

Note that the driving speed of the motor 27 can also be changed according to the operating speed of the joystick 36*a* tilt operation, and curving driving control can be performed to drive the curving of the curving portion 16 reflecting the tilting operation action of the joystick 36*a*. Also, when the joystick 36*a* is in a vertical state, the curving portion 16 can be made into a non-curving state (curving portion straight line state).

Also, a scope ID generating circuit 42 for generating a scope ID corresponding to the features of the curving mechanism within the operation unit 12 and the endoscope 2 is provided on a board 41 within the operation unit 12.

Note that the scope ID generating circuit 42 shown in FIG. 1 actually generates an operation unit ID along with the scope ID. Then, as will be described later, the scope ID is used primarily for specifying specific parameters (details to be described later) relating to the action of the curving mechanism unit 25 which performs curving driving of the curving portion 16, and the operation unit ID is used primarily for specifying specific parameters relating to the actions of an input command device such as the joystick 36a which performs curving instructions.

Thus, each scope 2 has a scope ID generating circuit 42, the curving control device 3 reads out the ID information thereof first, and by reading out (from a SRAM card 48 to be described later) and using the parameters corresponding to such ID information, the curving control device 3 can perform driving control of the curving, using parameters appropriate to the scope 2 actually to be used, even in the case wherein the types or features of the scope 2 differs.

Note that the reference numeral 40 is a mode switching switch for changing the operating mode of the curving, to be described later, wherein with this mode switching switch, switching setting can be performed for automatic mode to be performed with the joystick 36a, manual mode to be performed with an HMI (PC) 53, and a standby mode. According to the present embodiment, the mode switching switch 40 is disposed near the operation unit 12, but may be disposed on the curving control device 3 side.

The curving control device 3 has an MCU board 44 for performing curving control of the operation input unit 31 and the curving mechanism unit 25 and so forth, a servo driver 45 for performing control of the curving motor 27, a power source unit 46 for supplying power, and a UI panel 47 for the user to perform various settings and so forth, a SRAM card (PCMCIA card) 48 for storing various types of setting parameters, and an air/water feed/suction unit (abbreviated as AWS unit) 49 for controlling the air/water feed/suction device 7.

Also, an interface which is connectable to an external periphery device is provided on the curving control device 3.

For example, the MCU board 44 has an external interface connected to a monitor for displaying the curving state of the curving portion 16 and a personal computer (abbreviated as monitor (PC)) 51, a debugging console 52 for use in cases of performing maintenance, and a human interface PC (abbreviated as HMI or HMI (PC)) 53 for performing curving control in manual mode, in addition to the automatic mode for performing curving operations with the operation input unit 31, and for parameter changing settings, calibration, and so forth.

With the present embodiment, as will be described later, the MCU board 44 has a function of monitoring means for monitoring whether the curving action and the air/water feed/suction action are in a state of acting normally or whether they are in an abnormal state (error state) wherein an abnormality (error) is generated, as well as performing air/water feed/suction action control along with performing curving driving control by controlling driving of the curving mechanism unit 25 as to the operations of the operation input unit 31 of the endoscope 2.

Also, with the monitoring means, occurrence of an abnormal state can be detected, and also in the event that an abnormality occurs, the abnormality can be displayed to notify this to the user. Also, in the case of an abnormal state occurring, appropriate processing can be performed quickly as to the abnormal state occurring, such as stopping the electrically-operated curving action via an interlock 57 (see FIG. 2), thus improving the operability of the electrically-operated curving endoscope system 1.

Further, the curving control device 3 according to the present embodiment has a feature wherein a function of parameter setting means is provided to perform settings, changes, and so forth of parameters relating to curving actions and air/water feed/suction actions.

Note that with the present embodiment, parameters which can be set include air/water feed/suction parameters and so forth as well as parameters relating to curving driving control such as operation unit-specific parameters, scope-specific parameters, user setting parameters, servo adjusting parameters, and so forth, as shown in FIGS. 31A to 31D and FIG. 32 which will be described later.

Then, by performing parameter settings, using information such as the scope ID and so forth, as described above, curving driving control appropriate to each scope 2 case can be performed by a common curving control device 3, even with cases of scopes 2 with differing features.

By automatically performing settings for such parameters by using the scope ID information during initialization, settings appropriate to the scope 2 which is connected to the curving control device 3 can be set, enabling appropriate curving driving control.

Also, during operation, parameter changes can be set with the HMI (PC) 53 and so forth so as to perform curving driving control corresponding to user selections and so forth as well, thus maintaining good operability.

FIG. 2 shows a specific configuration of hardware with primarily the MCU board 44 is the main unit in the curving control device 3.

This MCU board 44 has a main CPU 55 serving as curving driving control means for performing overall control processing primarily for curving control, a monitoring CPU 56 for performing monitoring processing to monitory whether the curving control state is in a normal state or an abnormal state, wherein the main CPU 55 and the monitoring CPU 56 are connected to one another via a database so as to be capable of mutually transmitting and receiving data.

Also, the main CPU 55 is connected to a interlock 57 for performing actions such as turning the electromagnetic clutch 30 OFF during an abnormal state, or turning the main power to the servo driver 45 OFF and stopping the rotation action of the motor 27, via a control line.

Then, for example in the case of detecting an abnormal state by the monitoring CPU 56, for example, the information thereof is transmitted to the main CPU 55, and this main CPU 55 outputs an command signal by software as to an interlock 57. Then this interlock 57 performs actions such as rotation stopping and so forth of the motor 27 corresponding to the abnormal state. In other words, actions corresponding to the abnormal state is quickly performed.

Also, in an abnormal state, the interlock 57 transmits the information thereof to the monitoring CPU 56, and the monitoring CPU 56 transmits this information to the UI panel 47, and displays information regarding the abnormal state with the display unit 47b of the UI panel 47, thus enabling notification of the abnormal state to the user.

Also, in the case that an emergency stopping switch provided on the UI panel 47 is operated by the user, the interlock 57 performs the emergency stopping action of turning the power switch OFF, as well as transmitting an emergency stopping signal to the main CPU 55 also.

Also, the MCU board 44 is connected via an insulation circuit 58 to the servo driver 45, operation input unit 31, curving mechanism unit (also called scope mechanism) 25, and so forth, on the patient circuit side which is insulated from a secondary circuit on the main CPU 55 side.

Also, the main CPU 55 is connected to a first FPGA 59 provided with a communication function to which address data or a data bus is connected, and this first FPGA 59 is connected to a second FPGA 60 provided on the patient circuit side via an insulation circuit 58.

Also, with the monitoring CPU 56, the address data or data bus are connected to the first FPGA 59, and the first FPGA 59 generates various types of control signals to perform corresponding control processing.

To describe the configuration thereof in greater detail, the main CPU 55 is connected to the operation input unit 31 via the insulation circuit 58 with an RS 485 communication line. Then a 12-bit signal in the horizontal/vertical (RL/UD) directions are inputted from the joystick 36a configuring the operation input unit 31 to the main CPU 55.

Also, information of the operation input unit validation switch, and ON/OFF data about curving operation validation switch, neutral recovery switch, and switch operations for air feed, water feed, and suction are inputted into the main CPU 55, and the main CPU 55 performs control processing corresponding to the data.

Note that the operation signals of the four scope switches 38 provided on the operation input unit 31 are inputted into the scope switch processing circuit within the image processing device 4, wherein the image processing device 4 performs signal processing corresponding to the freeze operation and so forth assigned to the scope switches 38.

Note that the image processing device 4 is connected to a monitor 6, as well as a keyboard 4a for inputting patient data and so forth.

The motor 27 configuring the curving mechanism unit 25 provided within the operation unit 12 of the endoscope 2 is connected to the servo driver 45.

Then, when a tilting operation is performed with the joystick 36a of the operation input unit 31, the operation amount data of the tilting operation is inputted into the main CPU 55 via the RS 485 communication line, and the main CPU 55 receiving this input and transmits command values to the servo driver 45 via the first FPGA 59, insulation circuit 58, and second FPGA 60, and the servo driver 45 performs driving control of the motor 27 toward the command values.

Also, in this case, the rotation amount of the motor 27 is detected with the encoder 35, and the rotation amount data of the motor 27 detected by the encoder 35 is transmitted to the main CPU 55 via the second FPGA 60, insulation circuit 58, and first FPGA 59. Then the main CPU 55 controls the rotation amount of the motor 27 to be a value corresponding to the command values with the returned data via the servo driver 45.

In other words, a feedback loop based on the servo commands from the main CPU 55 is formed.

Also, the position data detected by the potentiometer 34 is inputted into the second FPGA 60 after the signal values are converted from analog into digital with an unshown AD converter. Then the signal is further transmitted to a main CPU 55 via an insulation circuit 58 and first FPGA 59. Also a signal for detecting slack by a slack sensor 61 for detecting slack of the curving wires 24 is inputted into the second FPGA 60 after the signal values are amplified with a distortion amp 62 and converted from analog to digital with an unshown AD converter. Then, the signal is further transmitted to the main CPU 55 via the insulation circuit 58 and first FPGA 59.

The position data detected with the potentiometer 34 is transmitted from the main CPU 55 to the servo driver 45, and is used for detection control of the curving range of the motor 27.

Also, in the case that the signal detected by the slack sensor 61 (a sensor for detecting the slack state of the wires) is inputted into the second FPGA 60, the second FPGA 60 detects whether the curving wires 24 are relaxed more than a permitted value, or whether the curving wires are disconnected.

In the case that such detection is made, notification is made to the interlock 57 to operate appropriately corresponding to the abnormal state thereof, via an ACTIVEN signal line. At the same time, error data is communicated from the FPGA 59 to the main CPU 55, and the main CPU 55 notifies this to the interlock 57 as software commands, via the software command signal line. Thus, when an abnormality occurs, the interlock 57 is quickly activated by way of hardware, and thereafter, specifying of the location can be performed with software commands, so that determining processing on the monitoring CPU 56 side can be performed.

Also, the scope-specific information by the scope ID generating circuit 42 is read into the main CPU 55 via the RS 485 communication line at the time of system startup, a parameter file corresponding to the specific information thereof is stored in an internal memory, so that in the case of the curving control device 3 performing various types of control, the information can be used with a parameter setting state appropriate to the endoscope 2 actually connected and used.

Also the main CPU 55 takes in the signals of the various switch operations for air feed, water feed, and suction of the operation input unit 31 via the RS 485 communication line, and outputs the control signal corresponding to these operations via an output line to the AWS unit 49.

When the air feed switch is operated, the AWS unit 49 converts the control signals inputted as 4-bit 16-step signals into PWM modulation analog signals with a converter CN1, controls the driving amount of an actuator 2V1 for realizing air feed such as an air feed electromagnetic valve and so forth, and further feeds the air via a pressure gauge P1.

Also, in the case that the water feed switch is operated, the driving amount of the actuator 2V1 for realizing water feed for an electromagnetic valve and so forth is controlled with a 1-bit control signal, and further feeds the water via a pressure gauge P2. Also, the driving amount of an actuator 3V1 for an electromagnetic valve and so forth is controlled with a 1-bit signal, and can perform switching wherein, in the case of air feed, the air is fed to the actuator 2V1 side and in the case of water feed, the water is fed to an actuator 2V2 side.

Also, in the case that the suction switch is operated, the driving amount is controlled with a pressure gauge P3 and 1-bit signal via an actuator PV1 of an electromagnetic valve and so forth, and further, a 4-bit control signal is converted to an analog open/close control signal via a converter CN2 and the driving amount of an actuator 2V3 of an electromagnetic valve and so forth is adjusted to cause suction.

Also, the air feed, water feed, suction pressure which is measured with the pressure gauges P1, P2, and P3 are each inputted into the monitoring CPU 56 via an 8-bit signal.

Also, the information monitored by the monitoring CPU 56 is transmitted to the display LED on the display unit 47a of the UI panel 47, wherein scope position, right and left/up and down curving amounts, and so forth are displayed directly without going via the main CPU.

Also, the monitoring CPU 56 outputs the information from the monitoring results to the LED 1 (G) and LED 2 (R) on the display unit 47b of the UI panel 47, and if the system is operating normally a green (G) LED 1 is lit, and if the system is operating abnormally, a red (R) LED 2 is lit and a warning sound is outputted from a speaker.

Also, a switching unit 47c on the UI panel 47 has provided thereon the above-described emergency switch, a release switch for releasing an abnormal state, and a power switch for turning the power source ON/OFF.

Also, the debugging console 52 is connected to the main CPU 55 with an RS232C serial communication line, whereby maintenance and program changes and so forth can be performed. This debugging console 52 can perform similar processing by being connected to the monitoring CPU 56.

Also, a PCMCIA slot serving as an external connection interface is provided on the main CPU 55, wherein a SRAM card made from a flash memory which is non-volatile and electrically re-writable can be detachably connected to the PCMCIA slot.

Also, by attaching the SRAM card 48, the main CPU 55 performs reading of the setting parameters from the SRAM card 48 at the time of processing startup. Also various types of log data collection, storage, and so forth during use can be performed. Note that a USB can be provided instead of a PCMCIA slot to serve as the external connection interface, and a flash memory equating to the SRAM card 48 can be detachable to the USB.

Also, the HMI (PC) 53 can be connected to the monitoring CPU 56 side, wherein operations for changing parameter settings from the HMI (PC) 53 side and for storing (saving) the changed parameters to the SRAM card 48 can be performed. Settings for log data collection and storage and so forth can also be performed from the HMI (PC) 53.

Also, the monitor (PC) 51 can be connected to the monitoring CPU 56 via an RS 232C serial communication line, and the curving state can be displayed on the monitor (PC) 51.

FIG. 3A shows the configuration of the operation input unit 31. A gripping portion 65 for the user to grip is provided on the operation unit 12 of the endoscope 2, on the portion near the insertion portion 11. When the user performs various types of operations with the operation input unit 31, the user grips this gripping portion 65 to perform the operations. Therefore, an operation input unit validation switch 66*a* for validating the operation is provided on the operation input unit 31, whereby various types of operations are performed while turning the operation input unit validation switch 66*a* ON by gripping the switch.

This is a switch for safety purposes, to confirm at the curving control device 3 side that the operator is intentionally gripping and performing the operation.

Also, an input command device 36 for curving operations is provided on the side face of the upper side of the operation input portion validation switch 66*a*, and a curving operation validation switch 66*b* is provided on the top portion and so forth of the input command device 36.

This is a switch for safety purposes, to confirm at the curving control device 3 side that the operator is intentionally performing the operation.

For the input command device 36 for curving operations with the endoscope 2, a device configured with a trackball or pointing device can be used instead of the joystick 36*a* shown in FIG. 1. In other words, the curving control device 3 according to the present embodiment can appropriately deal with any of a joystick 36*a*, trackball, or pointing device serving as the input command device 36, by reading in the scope ID information.

Also, as described above, four scope switches 38 and the AWS switch 37 are provided on the side face of the operation unit 12 on the endoscope 2.

Also, an engaging switch 66*c* is provided on for example the top portion of the operation unit 12, such that by operating this engaging switch 66*c*, the curving state can be fixed at the state immediately preceding the operation.

Note that besides the case shown in FIG. 3A, a pad switch or a cross-shaped pad 66*c* for performing curving operation command input in four directions (U, D, R, L) can be used as the input command device 36, as shown in FIG. 3B.

FIG. 4 shows the flow of data from the communication by the RS 232C between the curving control device 3 and the HMI (PC) 53, wherein curving control can be performed with the HMI (PC) 53 as shown in FIGS. 5A and 5B.

The monitoring CPU 56 transmits the instruction data from the HMI (PC) 53 and monitors the state thereof, that is to say, the monitoring CPU 56 is a CPU for performing processing dedicated to data monitoring and transmitting information such as a warning to the operator when an state transition occurs.

As shown in FIG. 5A, when the communication connection button on the upper right of the screen display is pressed, a connection request command is transmitted from the HMI (PC) 53 in FIG. 4 to the monitoring CPU 56 of the curving control device 3, and communication is established. Also, as a curving operating mode from the HMI (PC) 53, for example if the automatic mode is selected, the information thereof is transmitted via the monitoring CPU 56 and is stored in a communication area of a dual port RAM (abbreviated as DPRAM) 68 which configured common data, wherein this command data is read by the main CPU 55.

Then the main CPU 55 transmits the corresponding data from the system state of the DPRAM 68 and other data storage areas to the HMI (PC) 53 via the monitoring CPU 56. Then the display screen of the HMI (PC) 53 has a display such as that shown in FIG. 5A in the case of automatic mode, and such as that shown in FIG. 5B in the case of manual mode.

Further, as shown in FIG. 5A and FIG. 5B, curving control state display (status, servo, monitor), and file storage, measurement and so forth, to be described later, can be performed.

Also, various types of parameter change settings can also be performed from this HMI (PC) 53.

FIG. 6 shows the overall curving control function with the MCU board 44 according to the present embodiment. With an operating panel 71 formed from the UI panel 47 and so forth, the user can change parameter settings, clear errors, operate switches and so forth such as for emergency stopping, and can input the operation into a system control unit 73 via an external equipment interface 72.

Note that for the operating panel 71, a monitor with a touch panel on a PC may also be used instead of the UI panel 47.

The external equipment interface 72 comprises a bi-directional interface with the system control unit 73, an interface for the memory card which is non-volatile and electrically re-writable such as the SRAM card 48 or the like, and further has a communication processing function for performing external communication via Ethernet (registered trademark).

The system control unit 73 which is connected with the external equipment interface 72 holds the data read in at startup as common data 75, and referencing this common data 75 performs initialization processing 76, input/output processing 77 from the state of various types of switch operations from the operation input unit 31 and from the curving mechanism unit 25, action command generating processing 78 for detecting instruction operations from the operation input unit 31 and performing action commands of the motor 27, curving control processing 79 for performing processing of curving control of the motor 27 from the action commands, and malfunction processing 80 of an abnormal state by the monitoring CPU 56.

The action command generating process 78 performs reading processing of the command values from the input command device 36 such as the joystick 36*a* of the operation input unit 31. An operation unit input control unit 81 generates data for transferring the data from the operation unit to the action command generating processing unit 78. Additionally, this has a configuration for performing processing for force feedback control of the operation unit 12. This is for the purpose of distinguishing the servo processing for curving control processing and the servo processing for force control.

Then the generated data is transferred to the curving control processing 79, and the motor 27 is servo controlled via the servo driver 45, as the curving control processing 79. In this event, detection information of the encoder 35 and potentiometer 34 are used. Also, dynamic parameter settings described below can also be performed using the detection information from the slack sensor 61.

Also, for abnormal malfunction processing 80, monitoring processing of an emergency stopping 80c by the emergency stopping switch is performed, along with monitoring of a hardware abnormality 80a which is an abnormality of the hardware and a software abnormality 80b which is an abnormality of the software.

The primary functions according to the above-described configuration is shown in FIG. 7.

FIG. 7 shows modes and content for curving functions, air/water feed/suction functions, and operating methods and functions of the serial communication operation unit and so forth.

For example the curving function item includes several modes such as a position command mode, speed command mode, automatic recovery mode to return the curving portion to a neutral position, free curving mode, and so forth.

Also, the air/water feed/suction function includes modes for air feed and water feed operations and for suction operations, by the operation input unit.

Also, the serial communication operation unit function includes modes corresponding to connection, communication speed, communication cycles, and variations.

Also, other operation methods and functions include modes for system startup/shutdown sequences, system status display, scope switches, emergency stopping button, release button, manual mode, and so forth.

FIG. 8 shows the system functions, and shows the various modes and content thereof of the system functions, including system parameter settings/changes, maintenance-free, data logging, system monitoring, interlocking, RAS, calibration, and software downloads.

FIG. 9 lists the various tasks for abnormality processing (error processing), and shows that there are three levels of detection and error processing being performed, which are abnormality (error) level (degree) warnings, cut-off stopping, and emergency stopping.

In this case, emergency stopping processing is performed in the case of hardware abnormality, and in the case of software abnormality, processing is performed according to the degree of the abnormality. Together, the curving control device 3 has a configuration which can perform arbitrary settings for abnormal processing (various tasks) and error levels, rather than unique settings as in FIG. 9.

FIG. 10 shows the processing of the system control unit 73 in FIG. 6 with the relation between the main CPU 55 and the monitoring CPU 56, and assuming the DPRAM 68 to be shared data, the main CPU 55 and the monitoring CPU 56 are shared and processing is performed for each.

Also, the control device 3 has a configuration which can perform arbitrary settings for abnormal processing (various tasks) and error levels, rather than unique settings as in FIG. 9.

Note that the main CPU 55 and the monitoring CPU 56 in FIG. 10 show a processing function block including software besides the main CPU 55 and the monitoring CPU 56 in FIG. 2. In FIG. 10 and thereafter, the same notation is used.

On the main CPU 55 side in FIG. 10, a program code is mounted for performing sequence control relating to curving control such as clutch ON/OFF control or free curving, according to a predetermined program.

In order to perform this sequence control, processing for input/output signals, servo control, time control, and system control is performed together. Also, motion control (MCL control) is a processing unit for generating commands necessary for servo control, such as clutch processing, interpolating methods, speed and so forth, and action command generating processing is performed with MCL control. Also, operation input unit control is also performed, and the processing data is managed together with the shared data from a SDRAM 69a on the main CPU 55 side.

Also, in the event of time control processing, the data in the SDRAM 69a is used, and also the processed data is stored in the DPRAM 68, and is used to monitor and so forth on the monitoring CPU 56 side.

On the other hand, on the monitoring CPU 56 side, the shared data from the DPRAM 68 is loaded to perform the various processing for monitoring control, system control, and external communication control, and error monitoring is performed. For monitoring processing, the data is stored in the monitoring side SDRAM 69b and managed together as shared data, and is referenced as needed.

Also, data is outputted to the HMI (PC) 53 and so forth, or data is loaded from the HMI (PC) 53 by the external communication control. Also, in the case that a parameter change request command is transmitted from the HMI (PC) 53, the main CPU 55 performs parameter changing processing via the DPRAM 68.

FIGS. 11A and 11B show a specific example of the processing function shown in FIG. 10. FIG. 11A shows processing content primarily on the main CPU 55 side, and FIG. 11B shows processing content primarily on the monitoring CPU 56 side.

In FIG. 11A, the monitoring CPU 56 loads the shared data from the DPRAM 68 with a monitoring side application 82b, performs error monitoring processing, and inputs/outputs the monitoring data to the HMI (PC) 53.

On the other hand, on the main CPU 55, various types of setting parameters are held as shared data in the SDRAM 69a (as described later at the time of processing startup, the data stored in the SRAM cards 48 is rendered in this SDRAM 69a, and various types of setting parameters are held).

Also, an internal binary code for turning the clutch OFF and so forth is built into the interlock internal code, and after the internal code is translated to a language which can be processed with the MCL control (motion SCL control) by a SCL interpreter (sequence control), the internal code is transferred to the MCL control.

With this MCL control, processing for calculating command values for the purpose of motor driving which is generated by the confirmation/speed increase/speed decrease processing within the action range is performed, and the calculated motor command values are outputted to the time control (servo control) side.

Also, with this MCL control, action ranges and speed limits and so forth are calculated and transferred to the time control processing, and at the same time, the operation amount of the calculated data and so forth are stored in the SDRAM 69a. With the time control processing, servo control of the motor 27 is performed via the FPGA 59 and 60.

Also, in the event of this time control processing, output signals from the encoder 35 and so forth are inputted, and servo processing is performed with reference to the output of the encoder 35.

The processing portion of the time control inputs/outputs processing information into the patient circuit (operation input unit 31, curving mechanism unit 25) and the UI panel 47 via a digital input/output unit. Data from the pressure gauges P1 through P3 of the AWS unit 49 may be inputted, or a signal controlling the electromagnetic valve 2V1 or the like may be outputted, via the digital input/output unit.

The command values of the operation input unit control tasks are received by a transmitting/receiving driver via the RS 485 communication line from the input command device 36 of the joystick 36a and so forth, and are stored in the DPRAM 68. The operation amount of the command values and so forth stored in the DPRAM 68 is referenced in the event of servo processing.

Also, with the main CPU 55, various processing for operation input unit control tasks, MCL control, and time control are executed as timer-driven multitasking processing by an FPGA interruption 90 generated from the FPGA 60.

Specifically, operation input unit control tasks are executed with interruption processing of an operation input unit control startup message of 3.3 ms for example, or time control processing is executed with interruption processing of an time control startup message of 3.3 ms, or MCL control processing is executed with interruption processing of an MCL control startup message of 33.3 ms.

Also, FIG. 11B shows the processing of the monitoring CPU 56. In this case, the main CPU 55 side performs the curving control processing in FIG. 11A with a main side application 82a.

On the other hand, with a com1mgr 91a on the monitoring CPU 56 side, communication is performed with the HMI (PC) 53 via a transmitting/receiving driver which transmits/receives via the RS232C.

Also, with a com2mgr 91b, communication is performed with the monitor (PC) 51 via a transmitting/receiving driver which transmits/receives via the RS232C, and the curving state is displayed. FIG. 12A shows a display example of the curving state with the monitor (PC) 51. The positions of command values (shown with shaded lines) in the case of a joystick 36a for example, scope positions (shown with small circles), and wire tension states shown with a small circle in the center are displayed on the display screen in the four directions of R (right) L (left)/U (up) D (down).

Note that FIG. 12B shows a calibration display screen at the time of calibration action to be described later with FIG. 28.

A sensor signal is read with a monmgr 92, comparison is made with the data in DPRAM 68 shared with the main CPU 55 and error monitoring is performed.

Processing for warning with a sound at the UI panel 47 or driving processing of a flashing LED and so forth is performed with a subclock 93, by a FPGA interruption 90.

Specifically, with the 3.3 ms subclock startup message interruption, the subclock 93 performs tasks such as warning with a sound on the UI panel 47. Also, the subclock 93 generates a monmgr startup message interruption, and the monmgr 92 performs error monitoring tasks as to the sensor signals.

In this case, the data from the external equipment such as the HMI (PC) 53 or the like is stored in the DPRAM 68 via the com1mgr 91a and so forth, but in this event the monitoring CPU 56 has a feature such that error monitoring tasks with the com1mgr 91a and so forth are performed.

FIG. 13 shows the monitoring process in FIG. 11B in greater detail.

The main CPU 55 is connected with the monitoring CPU 56 via the interlock 57. According to this configuration, interlock commands can be outputted independently from both the main and monitoring CPUs, and therefore the information of whether or not the interlock 57 is in an error-detecting state, that is, Di (1-bit) information outputted from the interlock 57 to the monitoring CPU 56 shown in FIG. 2 is loaded into the subclock 93 of the system control (SYSMGR) within the monitoring CPU 56.

Also, the input/output state of the UI panel 47 set with the DPRAM 68 and the release switch information from the UI panel 47 are also inputted into the subclock 93.

With the subclock 93, these states are monitored, and status data of whether or not there is an error is stored in the monitoring error status area provided within the DPRAM 68.

Also, with the subclock 93, data regarding the input/output state of the UI panel 47 can be loaded, a clock can be outputted to a watchdog timer (abbreviated as WDT) 956 for monitoring the state of the monitoring CPU 56, state display data can be outputted to an LED or the like on the UI panel 47, and signals for interruption startup can be outputted to the monitoring processing (monmgr) 92.

Also, with this subclock 93, in the case that an error is detected, the data thereof is outputted to a sysmgr 96 within the system control.

Also, with the monmgr 92, a pressure gauge for the AWS unit 49, a potentiometer 34, a sensor signal for the slack sensor 61 are loaded, and the signals thereof are compared to a threshold value and monitored whether or not there is an error. The after initialization is completed, the error detection data is outputted to the sysmgr 96.

With the monmgr 92, determination is made as to whether there is any abnormality during startup as to the shared data with the SDRAM 69b.

Data in the case of error occurrence in the event of communication processing such as a parity check sum from the com1mgr 91a and com2mgr 91b of the communication processing (commgr), is also inputted into the sysmgr 96. As shown in FIG. 11B, the com1mgr 91a and com2mgr 91b each perform communication via the HMI (PC) 53, monitor (PC) 51 and serial communication interface (SCI) 97a and 97b.

Also, with the com1mgr 91a and com2mgr 91b, processing is performed such as reading in the data of the SDRAM 69b. Data from the main CPU 55 side may be stored in this SDRAM 69b via DPRAM processing by the monmgr 92, or data may be transmitted to the main CPU 55 side.

With the sysmgr 96, status data as to whether or not there is any error from the subclock 93, monmgr 92, or commgr 91 is stored in the monitoring status of the DPRAM 68, wherein processing corresponding to the data with the main CPU 55 side can be performed.

Note that even in the case that an exceptional error occurs such as zero division wherein the monitoring CPU 56 cannot compute at the time of computation by an exception (mgr) 99 with the system control, this is stored in the monitoring error status of the DPRAM 68.

Then the main CPU 55 reads in the monitoring error status area data of the DPRAM 68, and performs corresponding processing.

FIG. 14A shows checking processing for error monitoring during curving control by the monmgr 92 in FIG. 13.

When this error monitoring is started, seven checks are performed, from check routine A through check routine G. In this case, if the check results of the first check routine A are normal, the process moves to the next check routine B. On the other hand, in the case that an error is detected, this processing is ended, and the error content is stored in the monitoring error status of the DPRAM 68. The main CPU 55 performs processing corresponding to the error thereof.

With the check routine B and thereafter, the same checks are performed, only that the check content differs from that of the check routine A.

FIG. 14B shows the content of the check processing in the check routine in FIG. 14A. FIG. 15 shows the processing in FIG. 14A with a block diagram. Note that FIG. 15 primarily shows a case of a joystick (abbreviated in the diagram as J/S) 36a being connected, but as described later, this applies to case of using a trackball or a pointing device.

The serial data from the operation of the joystick 36a in the operation input unit 31 is assumed to be operation amount m at the position of the joystick 36a and operation amount m of speed. After the difference from the scope current position p is computed, each operation amount m is multiplied, by a sensitivity Kp to the difference Pp in the case of the position operation amount m, and by a sensitivity Kv to a difference Pv in the case of the speed operation amount m.

Note that by performing processing having redundancies by setting differing sensitivities Kp and Kv with the position case and the speed case, each case of position input commands and speed input commands can be appropriately handled. Also, an input command device other than a joystick 36a can also be appropriately handled.

After this, in the position case, the above-described values are added to the value pc (org) of the scope position origin, and this is inputted in the Pcommand together with the previous position command value pc_pre. pc(org) is for setting a unique motor position and endoscope curving position by adding an offset value for each clutch engagement, since the endoscope curving portion and motor driving unit are disengaged by the clutch and so a unique correlation of each position cannot be determined.

On the other hand, in the speed case, after the previous position command value pc_pre is added, this is inputted into the Pcommand.

The output of the Pcommand is inputted into a servo algorithm via a subtractor 98 after the converting coefficient Kth to be converted from the potentiometer voltage to the motor command value is multiplied, a PID control and so forth is performed with this servo algorithm, and the motor 27 is driven via the servo driver 45. Note that the output of the encoder 35 which detects the rotation amount of the motor 27 is subtracted by the subtractor 98 and is inputted into the servo algorithm.

Note that the Pcommand also has mode information inputted therein, such as manual, neutral recovery, and calibration, and can also perform processing corresponding thereto.

Also, the operation input of the operation input unit 31 is inputted into one of the input ends of a comparator C_D via the DPRAM 68, as serial data.

Also, the operation amount m at the joystick 36a position is connected to the other input end of the comparator C_D via the DPRAM 68. Then the comparator C_D performs comparison as to whether or not the serial data of the joystick 36a and the data after converting to the position or speed operation amount m matches.

Also, the other end of the comparator C_D is connected to one end of the comparator C_E via a converting converting processing unit (abbreviated as f()) which converts the comparison data to the same respective scale, and on the other input end of the comparator C_E, a motor command value wherein multiplication processing of the conversion coefficient Kth is performed is inputted. Then with the comparator C-E, the relation between the input source and the motor command value is checked.

Also, the other input end of the comparator C_E is connected to one input end of the comparator C_F via a converting converting processing unit (abbreviated as f( )) which converts the comparison data to the same respective scale/dimension, and on the other input end of the comparator C_F, a motor command value inputted to the subtractor 98 is inputted via the DPRAM 68. Then with the comparator C_F, the relation between the MCLMGR side and TIMCTL side and the motor command value is checked, as shown with the alternate long and short dash line in FIG. 15.

Also, the other input end of the comparator C_F is connected to one input end of the comparator C_G via a converting converting processing unit (abbreviated as f( )) which converts the comparison data to the same respective scale/dimension, and on the other input end of the comparator C_G, the output of the encoder 35 is inputted via the DPRAM 68. Then with the comparator C_G, the relation between the motor command value and encoder value is checked.

Also, the other input end of the comparator C_G is connected to one input end of the comparator C_C via a converting converting processing unit (abbreviated as f( )) which converts the comparison data to the same respective scale/dimension, and on the other input end of the comparator C_C, the output of the potentiometer 34 is inputted via the DPRAM 68. Then with the comparator C_C, the relation between the encoder value and the potentiometer value is checked.

Also, the input other end of the comparator C_C is connected to one input end of the comparator C_B, and on the other input end of the comparator C_B, an output signal of the potentiometer 34 is inputted. Then with the comparator C_B, whether or not the same sensor values on the main side and the monitoring side match is checked.

Thus, the comparators C_D, C_E, C_F, C_G, C_C, and C_B each show the checks for check routines D, E, F, G, C, B in FIG. 14A with respective block diagrams.

Also, the signal wherein the sensitivity Kv is multiplied by the difference Pv, as shown in FIG. 15, is subjected to check & clamp processing of the potentiometer speed. Also, the signal wherein the origin value pc (org) is added is subtracted from the previous origin value pc (org), and potentiometer speed checking & clamp processing are performed.

Also, the potentiometer position (theoretical position) is checked from the Pcommand output. Also, with the output of the potentiometer 34, the potentiometer position (actual position) is checked.

The potentiometer position has a theoretical position and an actual position, but as will be described later, the operation means has a command wherein the command is limited, as with the joystick, and an unlimited command such as with the trackball. Therefore, the potentiometer (theoretical position) is provided as necessary information for calculating the consistency of the operation unit position and the potentiometer position.

Further with an input signal to the servo driver 45, the motor speed can be checked.

FIG. 16A illustrates the contents of processing for the part up to outputting a motor command value from the operation input unit 31 in FIG. 15 via the coefficient Kth, in the case of using the joystick 36a. Also, FIG. 17A and FIG. 18A illustrate the contents of processing for the same part in cases of using a pointing device and a trackball respectively, instead of the joystick 36a. Note that FIG. 16A, FIG. 17A, and FIG. 18A show the contents of processing at the time of periodic command, periodically performed following the startup command.

In the case of performing such processing, the scope ID information is used so as to enable processing corresponding to the scope 2 actually connected to the curving control device 3 as the input command device 36.

As shown in FIG. 16A, in the first step S1, the main CPU 55 performs processing for reading the scope current position from the detection value of the potentiometer 34. That is to say, the current position p of the scope unit is acquired as shown in FIG. 16C. In the following step S2, the main CPU 55 acquires the operation amount m of the position command made by the joystick 36a.

This operation amount m is arranged so as to represent values from −10 V to +10 V in 12 bits, for example, as shown in FIG. 16B.

In the next step S3, the main CPU 55 performs operation amount limit processing. As shown in FIG. 16B, processing is performed for restricting from the lower limit side operation amount limit (min) to the upper limit side operation amount limit (max).

In the next step S4, the main CPU 55 makes a pti calculation, i.e., calculates a value by multiplying the operation amount m by sensitivity, as shown in FIG. 16B.

Now, sensitivity is a parameter set due to operating sensations different according to the command input type, such as position command, speed command, and so forth. Accordingly, this is a parameter whereby there is no need to reset several parameters set for the curving control device 3 each time the command mode is switched over, and can be handled by setting only the sensitivity parameter (providing the parameter before input to Pcommand allows the parameters up to generating a motor command from a Pcommand to be integrated).

This is then converted into an operation amount logical coordinate system (pti) as shown in FIG. 16B.

Next, in the following step S5, the main CPU 55 performs a pc calculation, i.e., performs processing for calculating a scope portion potentiometer command value pc, as shown in FIG. 16B.

That is to say, as shown in FIG. 16B, pc=pre_pc+Kp×(pti−pre_pti) is calculated. Here, pre_pc and pre_pti for example represent the previous command values obtained by multiplying the scope portion position and operation amount by the sensitivity, respectively.

In the next step S6, the main CPU 55 performs limit processing with regard to the processing made in step S5, i.e., pc limit processing. In step S7, the main CPU 55 performs th calculation with regard to the scope unit potentiometer command value pc subjected to such limit processing, i.e., performs processing for calculating the motor command value th.

That is to say, as shown in FIG. 16B, th =pre_th+Kth×(pc−pre_pc) is calculated.

Following calculating this motor command value th, in step S8 the main CPU 55 performs speed restriction processing. Specifically, in the event that the difference value Δth as to the previous value exceeds max speed×sensitivity, a speed limit is applied.

Subsequently, the flow returns to step S4 and re-calculation is performed using the difference value Δm of the operation amount calculated from the max speed×sensitivity.

This is in order to perform a re-calculation to match the command value with the amount which the motor 27 actually operates, and is for corresponding in a unified manner the amount actually moving with the operation unit, even in the event that a command value exceeding the operating range is made.

Following further subjecting the motor command value th thus calculated to the software limit processing in step S9, this is outputted to the subtractor 98 side shown in FIG. 15.

FIG. 17A illustrates a case of processing using a pointing device instead of the joystick 36a. In steps S1 through S3, the scope current position is acquired, operation amount is acquired, and operation amount limit processing is performed, in the same way as with FIG. 14A.

In step S11, the main CPU 55 performs dead band processing. That is to say, a pressure sensor is used with the pointing device, so a dead band has been provided such that appropriate operation output can be obtained with regard to operations made with the pointing device.

This is because with operating systems having a command arrangement using the amount of operating force rather than the position as with a pointing device, the amount of operation of the operator is readily directly reflected, so a dead band is provided to prevent sudden command operations.

To this end, processing for calculating the operation amount m taking this dead band into consideration is performed.

That is to say, the operation amount m is set as m=pre_m+(origin−mi)×sensitivity with regard to the operation input amount mi as shown in FIG. 17B, thereby removing the dead band (origin−mi).

Following this dead band processing, the steps S4 through S7 are preformed in the same way as with FIG. 16A, and further, the software limit processing in step S9 is performed without performing step S8. These are the same processing as with the case in FIGS. 16A, 16B and 16C, so description thereof will be omitted.

FIG. 18A illustrates a case of processing using a trackball instead of the joystick 36a. In steps S1 and S2, the scope current position is acquired, and operation amount is acquired, in the same way as with FIG. 16A.

Next, the processing from step S4 through step S7 and the processing of step S9 are performed. These are the same processing as with the case of the pointing device in FIG. 17A.

Thus, with the present embodiment, in any case of using the joystick 36a, pointing device, or trackball, as the input command device 36, curving driving control suitably corresponding thereto can be performed.

Next, the contents of processing regarding various types of abnormalities occurring will be described in detail with reference to FIG. 19 through FIG. 22. Note that the numbers (1) through (3) in FIG. 19 illustrate the occurrence order of an abnormality (error) and processing. This is the same for the other FIG. 20 through FIG. 22 as well. These illustrate the contents of processing with regard to error occurring within the curving control device 3.

FIG. 19 illustrates the contents of processing in the event of an exception occurring. The commmgr 91, monmgr 92, subclock 93, and sysmgr 96 within the monitoring CPU 56 perform respective computation processing, so in the event that an exception occurs in the computation processing the information thereof is detected in the exception 99.

The error information of the occurring exception that has been detected by the exception 99 is inputted to the interlock 57, and the interlock 57 generates an emergency stop command in response to the occurrence of the error. Note that in addition to detecting various types of abnormalities by hardware and software and outputting output for emergency stopping, as described later with reference to FIG. 35, the interlock 57 also forbids the main power of the servo driver and the like from turning ON, the servo from turning ON, and the clutch from turning ON (i.e., effects ON/OFF control).

Also, the exception information is stored in a monitoring error status area of the DPRAM 68 via the exception 99, and also the information thereof is sent to the UI penal 47, and the abnormality is displayed on the UI panel 47.

FIG. 20 illustrates processing regarding errors occurring at the main CPU 55 side. Upon an error occurring at the main CPU 55 side, the error information is stored in the areas of LED (for display) information, error code, and error severity, in the DPRAM 68.

Here, with error severity, 0 is normal, 1 is a warning, 2 is a cut-off stop, and 3 is an emergency stop. The greater the number is, the more severe the error indicated is.

The error information is read out by the subclock 93 and an error display thereof or the like is made at the UI panel 47.

Also, the error information is transmitted to the HMI (PC) 53 by the commmgr 91a, and the error information is displayed at the display screen of the HMI (PC) 53.

Thus, the present embodiment has status detecting functions for monitoring from a normal state to a state in which an error has occurred, and further has functions wherein, in the event that an error has occurred, the severity of the error is detected and a display is made of the severity of the error. Of course, a display is made in a normal state, as well.

FIG. 21 illustrates processing at the time of a call error in the operations system (abbreviated as OS), occurring as a software error at the monitoring CPU 56 side.

The commmgr 191a, monmgr 92, subclock 93, and sysmgr 96 at the monitoring CPU 56 each execute software, upon an error occurring, each error is notified to the sysmgr 96.

The sysmgr 96 then notifies the interlock 57 of the error information, and the interlock 57 performs emergency stop operations. Also, the sysmgr 96 stores the error information in the monitoring error status area of the DPRAM 68.

Then, the main CPU 55 reads in the error in this monitoring error status error, and stores the LED (for display) information, error code, and error severity in the respective areas in the DPRAM 68.

This error information is read out by the subclock 93 and an error display thereof or the like is made on the UI panel 47.

Subsequently, as with the case shown in FIG. 20, the error information is transmitted to the HMI (PC) 53 by the commmgr 91a, and the error information thereof is displayed on the display screen of the HMI (PC) 53.

FIG. 22 illustrates processing at the time of an error occurring which has been detected by hardware by the interlock 57.

Upon an error such as a line breakage or the like being detected by the interlock 57, the information is stored in the respective areas in the DPRAM 68 for LED (for display) information, error code, and error severity, via the main CPU 55.

This error information is read out by the subclock 93 and an error display thereof or the like is made on the UI panel 47.

Also, the error information is transmitted to the HMI (PC) 53 by the commmgr 91a, and the error information thereof is displayed on the display screen of the HMI (PC) 53.

FIG. 23 illustrates the contents of processing of the curving control device 3, from startup to shutdown. In this case, the left side of FIG. 23 illustrates the lit state of the LED indicating the activation state of the system on the UI panel 47.

The curving control device 3 is connected to an endoscope 2 ore the like, and the main power of the MPU board 44 of the curving control device 3 is turned ON in step S31. Then as shown in step S32, the main CPU 55 starts system check and initialization processing. Also, the monitoring CPU 56 also starts initialization processing. At this time, the LED of the UI panel 47 goes from an unlit state to a yellow lit state. In this case, green and red LEDs may be lit at the same time, to light up yellow.

Upon the system check and initialization processing in step S32 ending, and both the main CPU 55 and monitoring CPU 56 found to be normal, the flow proceeds to the system ready state in step S33, and the LED is in a state of being lit green.

Following the system ready state in step S33, the curving operation mode wherein the curving portion 16 of the endoscope 2 can be curved is realized in step S34, and the automatic mode, manual mode, or standby mode can be selected by the mode switchover switch so as to perform curving control in the selected mode.

Note that with the present embodiment, the mode switchover switch may be the mode switchover switch 40 provided to the operation unit 12 shown in FIG. 1 for example, or may be one provided to the HMI (PC) 53 as shown in FIG. 5A and FIG. 5B. In FIGS. 5A and 5B the standby mode cannot be selected, but an arrangement may be made wherein it can. Also, the mode switchover switch may be provided to the panel or the like of the curving control device 3 besides the above arrangements.

The automatic mode, manual mode, and standby mode can be mutually switched between as shown in FIG. 22.

The automatic mode is a standard operating mode wherein the curving portion 16 is curved by command values from the curving operations made at the joystick 36a or the like provided to the operation input unit 31 of the endoscope 2. The manual mode is a curving control operating mode wherein the curving can be independently operated by manual operations of the operator by pressing buttons corresponding to the curving directions of R (right), L (left), U (up), and D (down), on the HMI (PC) 53, changing and setting the curving speed, setting air/water feed/suction, and so forth, from the HMI (PC) 53.

Also, the standby mode is a mode wherein the movement of the moving parts such as the motor 27 and so forth of the curving mechanism unit 25 is temporarily stopped in the automatic mode or manual mode, whereby speedy recovery to a curved state can be made in the automatic mode or manual mode.

Curving control is then performed in the automatic mode or manual mode, and in the event of ending curving control following performing endoscope inspection, the main power of the MPU board 44 is turned OFF, whereupon the LED is turned off, and the normal running sequence ends, as shown in step S35.

FIG. 25 illustrates the actions in a case of a warning occurring during the normal running sequence shown in FIG. 23 and a case of resolving the occurrence thereof.

As described with FIG. 23, in the operating mode in step S34, there are cases wherein a warning is issued during operations, and upon a warning occurring warning processing 111 is performed and a display is made on the UI panel 47 to the effect that a warning has occurred.

Accordingly, upon performing a releasing operation with the release switch on the UI panel 47, processing for canceling the warning display is performed, and the mode is restored to an operation mode with no warning.

FIG. 26 illustrates a case of an emergency stop occurring which cannot be recovered from, and actions of processing with regard to occurrence thereof. As shown in FIG. 26, in the system check and initialization processing in step S32, or in the operating mode in step S34, there are cases wherein a malfunction which cannot be recovered from occurs, and upon such an abnormal state occurring, malfunctioning processing 112 is performed.

The malfunctioning processing 112 performs lighting of a red LED, and displaying an error code, but this cannot be recovered from with the release switch. Accordingly, the main power is turned OFF as shown in FIG. 26, following which the main power is to be turned ON to recover.

FIG. 27 illustrates occurrence of a cut-off stop, and actions for handling such an occurrence. As shown in FIG. 27, there are cases wherein a malfunction which can be recovered from (cut-off stop) occurs in the operating mode in step S34. This malfunction is an abnormality which can be recovered from, such as abnormal servo deviation, the curving exceeding the operable range, and so forth.

In the case of such a malfunction, the malfunction processing 113 is carried out wherein, following changing to manual mode, the curving is manually changed so as to be within the operable range or the like, whereby the abnormality can be removed, restoring the normal operating mode.

FIG. 28 illustrates the operating sequence for calibration. Also, to the right side is shown the state of lighting of the LEDs corresponding to the calibration state.

At the time of the system check and initialization processing in step S32, calibration data readout processing is performed. That is to say, readout is performed of calibration data such as the curving range for the R, L, U, and D in the case of a connected endoscope 2, curving speed, and so forth. In this case, the LED indicating the calibration state is lit green.

Also, the operations in the normal operation mode in step S34 (normal running) start. In the event of performing calibration, the calibration switch is turned ON, as shown in step S41.

Specifically, selecting the calibration tag positioned around the middle in FIG. 12B on the HMI (PC) 53 brings on the calibration display screen shown in this FIG. 12B, and pressing the start button starts calibration.

In this state, the curving servo is ON and the clutch is set to ON, and as shown in step S42, the curving portion 16 is repeatedly slowly curved in the R/L and U/D directions. In this case, the LED indicating the calibration state is lit yellow.

At this time, the input/output gain of the servo driver 45 is set to a constant level, and actual calibration data, such as the amount of rotation of the motor 27 as to the amount of operation of the joystick 36a at the operation input unit 31 side, and so forth, is acquired.

As shown in step S43, the calibration data that has been acquired is stored, and the calibration data read out at the time of system check and initialization is corrected. Thus, the calibration sequence ends. The LED indicating the calibration state is then lit green.

Even in the event there is offset between the actual amount of curving at the curving portion 16 side as to the operations made at the operation input unit 31 side, performing such calibration by repetitive curving operations enables the offset between the two to be resolved.

More specifically, over long periods of repeated curving operations being performed, there are cases wherein even though the joystick 36a for example is tilted to the operating range limit in the U direction for example at the operation input unit 31 side, but the curving portion 16 does not curve as far as the curving angle corresponding to that limit. Such cases can be restored to the initially set state by performing calibration.

FIG. 29 illustrates the sequence of the startup procedures and shutdown procedures including the main CPU 55 and the monitoring CPU 56. A feature of this sequence is that upon the main CPU 55 and the monitoring CPU 56 normally completing initialization, the cut-off state is temporarily set, as will be described below.

Upon the main power of the MPU board 44 (the CPU board thereof) being turned ON, the main POWER (main side power) of the main CPU 55 turns ON and the monitoring POWER (monitoring side power) of the monitoring CPU 56 turns ON.

As indicated in steps S51a and 51b, the OS then starts up at the main CPU 55 side and the OS also starts up at the monitoring CPU 56 side, with both performing respective initialization processing by way of handshake.

Specifically, following the OS at the main CPU 55 side starting up and further an application task starting up, a predetermined area in the DPRAM 68 is cleared, the shared data area in the SDRAM 69a is cleared, and shared data is read from the SRAM card 48.

Subsequently, the main CPU 55 notifies completion of loading the shared data at the main side to the monitoring CPU 56 side by handshaking via the DPRAM 68 area, and starts initialization processing at the main CPU 55 side.

The monitoring CPU 56 receives notification of completion of loading of the shared data at the main side, notifies the main CPU 55 side of starting initialization processing at the monitoring side, and the monitoring CPU 56 starts initialization processing.

Upon ending the initialization processing, the monitoring CPU notifies the main CPU 55 of ending of initialization processing at the monitoring CPU 56 side.

Thus, upon initialization processing normally ending at both the main CPU 55 side and the monitoring CPU 56 side, the flow enters the cut-off stop state in step S52, with the main CPU 55 side awaiting releasing of the cut-off stop state in step S53a.

This cut-off stop state is implemented to enabling operations upon a release SW command for releasing, in order for the operator intentionally start operations (due to safety considerations, the curving control device 3 is not placed in a state capable of performing curving operations from the operation unit as soon as the power is turned on). While a cut-off stop releasing standby step is illustrated with the present embodiment, an arrangement may be made wherein there is no cut-off stop releasing standby.

In this cut-off stop releasing standby state in step S53a, operating the release switch on the UI panel 47 releases the cut-off stop state, and the flow proceeds from the cut-off stop releasing standby state to the state in the next step S54a for performing operation such as curving control actions and the like. Note that the monitoring CPU 56 side proceeds to the (monitoring) operation processing in step S54b following the cut-off stop state having been released.

Following operation processing, at the main CPU 55 side, the main CPU 55 performs determination regarding whether or not the operations of step S55a have ended, and in the event of not having ended, the flow returns to the operation processing thereof, and in the event that the operations have ended, the ending preparation processing in step S56a is performed.

Following having performed the ending preparation processing such as saving data and so forth, the power of the MCU board 44 is turned OFF in step S57. On the other hand, at the monitoring CPU 56 side, following operations, the main power of the MCU board 44 is turned OFF in step S57.

FIGS. 30A and 30B illustrate the timing for operations of turning the electromagnetic clutch 30 ON and OFF, with FIG. 30A illustrating a case of turning the electromagnetic clutch 30 from OFF to ON, and FIG. 30B illustrating the timing for turning from ON to OFF. Note that in both drawings, above the solid line are command values and below are actual actions. Also note that the numbers (1) through (5) indicate temporal order of operations.

Upon a servo ON command being outputted from the MCU board 44 side to the motor 27 of the curving mechanism unit 25, as shown in FIG. 30A, a servo drive signal is supplied from the servo driver 45 to the motor 27 within a short time delay Ta, and the servo goes to the ON state.

Also, following the above time delay Ta, a clutch ON command is outputted from the MCU board 44 side to the electromagnetic clutch 30. Following a delay time Th from this command, a command is sent from the MCU board 44 side to the servo driver 45. In this case, the electromagnetic clutch 30 is in an engaged state before the delay time Tb elapses.

Accordingly, transition can be made to the operating state without transmitting unnecessary noise to the endoscope, such as vibrations occurring at the time of supplying energy for driving the motor.

On the other hand, in the event of turning the electromagnetic clutch 30 OFF from the ON state, a command end, clutch OFF command, and servo OFF command are outputted from the MCU board 44 side almost simultaneously, as shown in FIG. 30B. Then, following a short period, the electromagnetic clutch 30 goes to a disengaged state.

Thus, performing control wherein the clutch ON command is outputted following turning the servo ON enables the motor 27, which curves the curving portion 16, to be placed in a state wherein servo driving can be performed in a smooth manner.

FIGS. 31A to 31D illustrate operations such as operations and usage of rendering setting parameters stored in the SRAM card 48, changing and storing thereof, and so forth. In the case of this FIGS. 31A to 31D, an operation example is shown for a case of static setting parameters wherein there is little temporal change or wherein there is almost no need for changing, during a single endoscope inspection. Also, in other words, this illustrates the operations of rendering, using, changing, and storing the setting parameters as to the setting parameters stored in the SRAM card 48 in a read-only state. Note however, that writing is performed in the case of storing. The numbers in the drawing illustrate the order of operations.

On the other hand, FIGS. 33A to 33D illustrate a case of dynamic setting parameters wherein temporal change readily occurs or wherein change should occur over time, during a single endoscope inspection. In other words, this illustrates the operations of rendering, using, changing, and storing the setting parameters to be read/written.

Figure 31A:
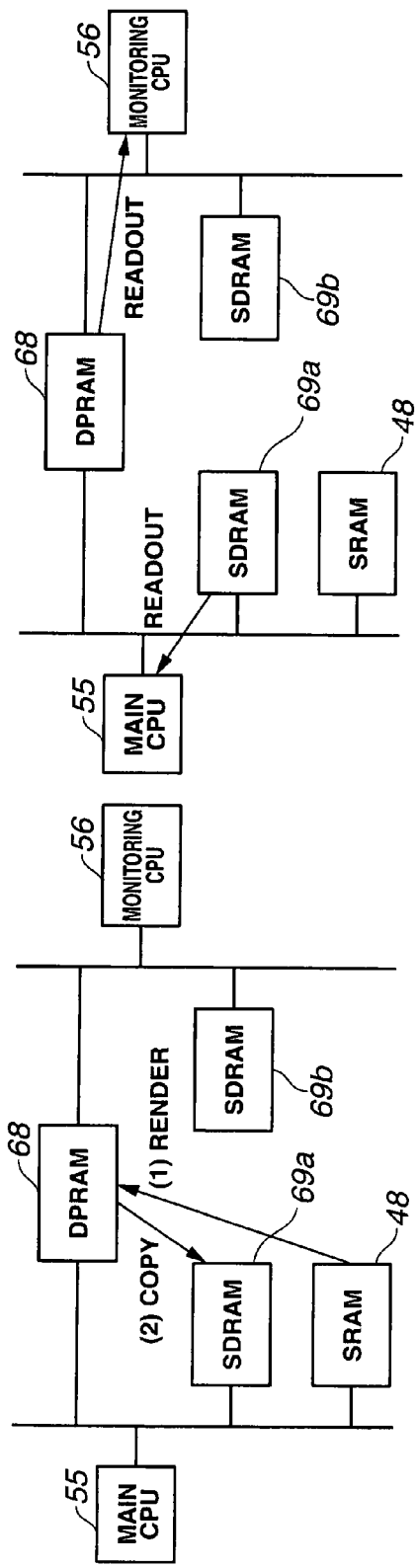
FIGS. 31A to 31D are explanatory diagrams illustrating the actions for each case of rendering static setting parameters stored in a SRAM card, using of the setting parameters following rendering, a change request, and a storage request.

FIG. 31A illustrates an operation example of rending setting parameters, which is performed at the time of initialization processing. As shown in FIG. 31A, at the time of initialization processing, the main CPU 55 renders parameter files unique to the operation unit, parameter files unique to the scope, and AWS parameter files, which are stored in the SRAM card 48, to (the system parameter area of) the DPRAM 68, such as shown in FIG. 32.

In this case, the main CPU 55 first reads in the operation unit ID and scope ID, and reads out parameters unique to the operation unit, parameters unique to the scope, and so forth, which correspond to (are unique to) the operating ID and scope ID that have been read in, from the SRAM card 48.

Thus, even in the event that the types of scope 2 used for the endoscope inspection or the like differ, the main CPU 55 reads out the unique parameters satiable for the scope 2 from the SRAM card 48, and renders to the DPRAM 68.

Also, as shown in FIG. 31A, the various types of setting parameters rendered to the DPRAM 68 are then copied by the main CPU 55 to the SDRAM 69a connected by data bus thereto.

Figure 31B:
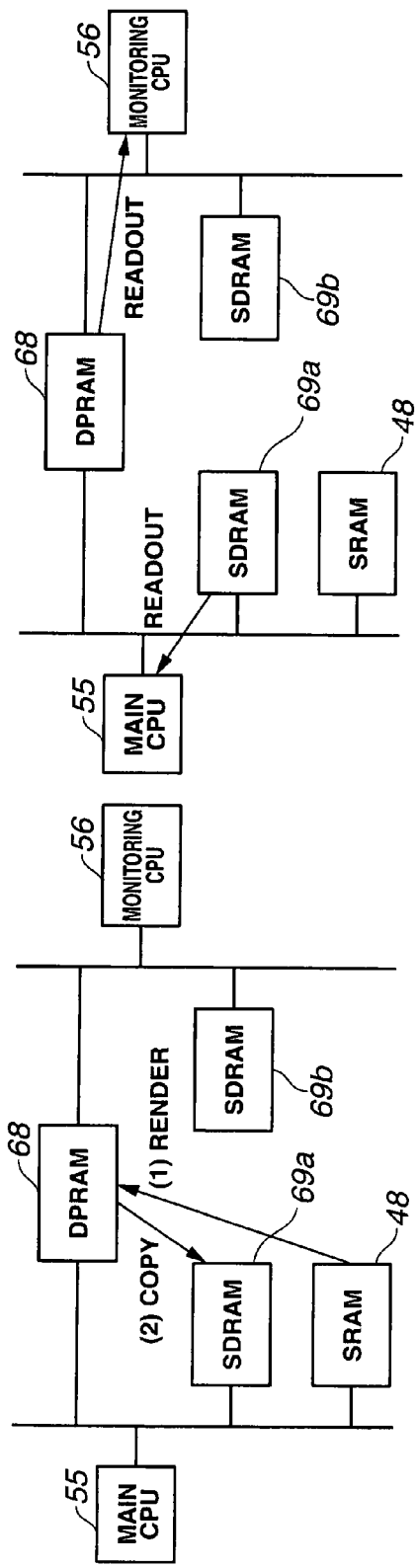

FIG. 31B illustrates the operations of using the setting parameters, i.e., normal operations. In the event of using the setting parameters at the main CPU 55 side, the main CPU 55 accesses the SDRAM 69a, and reads out the setting parameters from the SDRAM 69a.

On the other hand, in the event of using the setting parameters at the monitoring CPU 56 side, the monitoring CPU 56 accesses the DPRAM 68, and reads out the setting parameters from the DPRAM 68.

Figure 31C:
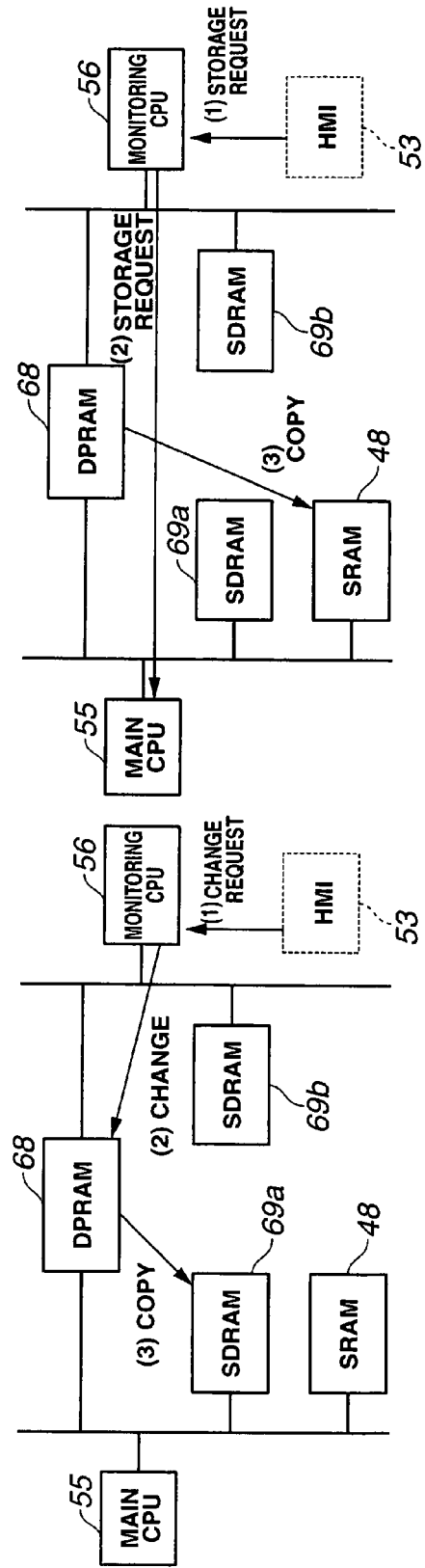

FIG. 31C illustrates a case of changing the setting parameters. In this case, the user operates the HMI (PC) 53 to send setting parameters for a change request for setting parameters to the monitoring CPU 56 via the HMI (PC) 53, such as changing the operating range of curving or the like.

The monitoring CPU 56 then changes the corresponding setting parameters before change that are stored in the DPRAM 68, based on the change request for setting parameters. Subsequently, the main CPU 55 copies (overwrites) the changed setting parameters from the DPRAM 68 to the SDRAM 69a, thereby changing the corresponding setting parameters before change.

The setting parameters in the present embodiment include, as described with FIG. 32 and others, parameters unique to the operation unit, parameters unique to the scope, AWS parameters, user setting parameters, servo adjustment parameters, and so forth.

While FIG. 31C illustrates that the setting parameters can be changed and set by the HMI (PC) 53 connected to the curving control device 3 via an external interface, another arrangement may be made wherein operating means which can change and set the setting parameters may be provided to the UI panel 47 or the like of the curving control device 3, for example.

Figure 31D:
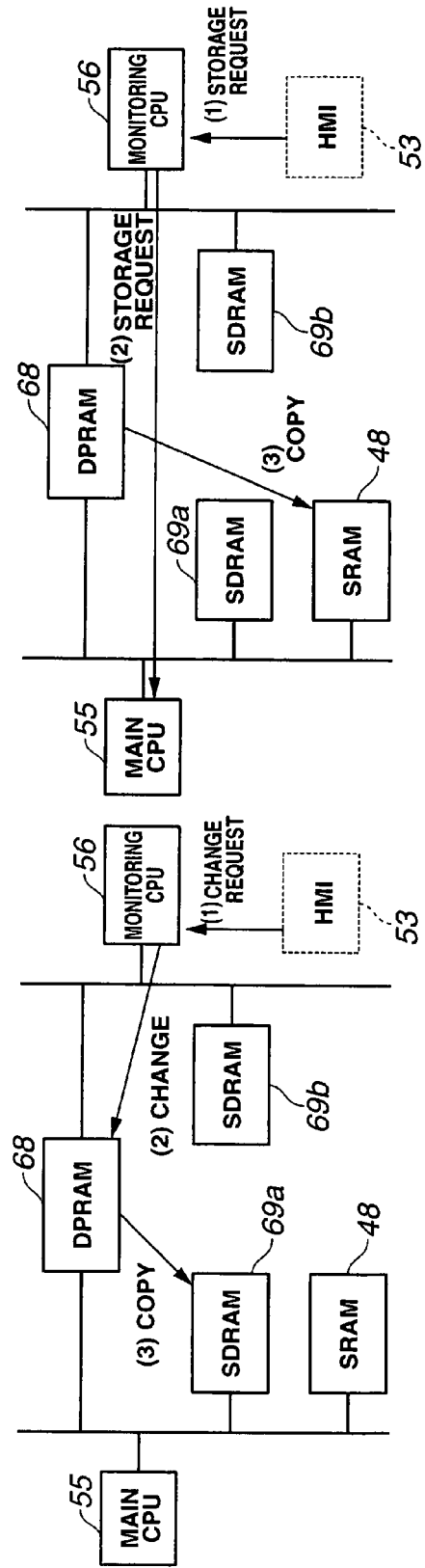

FIG. 31D illustrates operations for storing the setting parameters. In the event that the setting parameters have been changed, simply turning OFF the power does not save these, so in the event that the setting parameters have been changed and using the changed setting parameters next time on is desired, the HMI (PC) 53 is operated so as to send a setting parameter storage request command to the monitoring CPU 56.

The monitoring CPU 56 then sends the setting parameter storage request command to the main CPU 55. The main CPU 55 receives the setting parameter storage request command and copies (overwrites) the requested parameter files from the DPRAM 68 to the SRAM card 48.

This SRAM card 48 is nonvolatile, and accordingly is held even when the power is OFF, and the changed setting parameters can be used the next time.

FIG. 32 illustrates the various types of setting parameters stored in the SRAM card 48 and the actions of copying these setting parameters to the DPRAM 68 or DRAM 69a.

As shown in FIG. 32, stored in the SRAM card 48 are operation unit-unique parameter (files), scope-unique parameter (files), and AWS parameter (files), and also stored are user setting parameter (files) and servo adjusting parameter (files).

The parameters unique to the operation unit are parameters set for each operation unit, with an ID No. assigned for each operation unit. Also, as many as the number of operation units supported by the curving control device 3 are provided.

Specifically, parameters unique to the operation unit include operation unit ID, operation (input) unit name relating to information of the joystick 36a, trackball, or pointing device, maximum value and minimum value of the operating range for curving in the RL/UD directions from the operation unit, dead band, sensitivity, force sense feedback properties, and so forth.

Also, the parameters unique to the scope are parameters set for each scope 2, with an ID No. assigned for each scope 2. Also, as many as the number of scopes 2 supported by the curving control device 3 are provided.

Specifically, parameters unique to the scope include scope ID, operating range of the scope 2 (properties of the motor 27 making up the curving mechanism unit 25 such as operating sign and maximum speed and the like, encoder 35 properties, potentiometer 34 properties, loop gain properties and the like of the servo system of the motor 27, and so forth), etc.

Also, AWS setting parameters are parameters set for each sequence, with an ID No. assigned for each sequence. Also, as many as the number of sequences supported by the curving control device 3 are provided.

The user setting parameters are parameters other than the above to be set. Specifically, these are parameters for setting the wait time for clutch ON and OFF, wait time for servo ON and OFF, manual speed, whether or not to make measurement data saving valid, whether or not to make error data saving valid, and so forth.

Also, the servo adjusting parameters are parameters necessary for using the servo adjusting functions. Specifically, these are parameters such as the sampling cycle, amplitude of motor pulses for driving the motor 27, selection of the servo algorithm, gain, and so forth. Now, complementary description will be made regarding a case of reflecting the setting parameters at the HMI (PC) 53.

As described above, several parameter settings can be made with the present device, which can be generally divided into dynamic setting parameters, which are sampling frequency, gain, amplitude, and so forth necessary for driving actuators such as the motor 27 and other like servo adjusting parameters, and static setting parameters, which are defined as setting parameters other than the above dynamic setting parameters, which are the operational range, sequence, ID, operation unit sensitivity, and so forth.

Now, as indicated above, the setting parameters can be optionally changed using the HMI (PC) 53, but only static parameters are enabled to be set at the HMI (PC) 53.

That is because setting of dynamic parameters such as motor driving and so forth requires knowledge and experience, and casually setting these may result in unstable actions and unintended behavior. Accordingly, only static parameters can be changed at the HMI (PC) 53, taking safety of the device into consideration.

With the example in FIG. 32, one operation unit-unique parameter A2.bin, out of a plurality (255) is first copied to the area for the connected operation unit 1, in the system parameter area of the DPRAM 68. In this case, information of the ID unique to the operation unit is read out as described above, and the operation unit-unique parameter A2.bin for example, is copied corresponding to that information.

Next, a scope-unique parameter B1.bin, is copied to the area for the connected scope, in the system parameter area of the DPRAM 68. Next, two AWS parameters AW1.bin and AW2.bin, are copied to the areas for the AWS1 and AWS 2. Further, a user adjusting parameter U.bin and a servo adjusting parameter are copied to the user setting area and the servo adjusting area, respectively.

These parameters copied to the DPRAM 68 are further copied to the SDRAM 69a as shown in FIG. 31A, and the initialization ends.

FIGS. 33A to 33D illustrate operations such as operations of rendering, using, changing, and saving setting parameters, in a case of dynamic setting parameters. Such dynamic setting parameters are values which are perpetually updated at the time of normal operations, and the final updated values at the time of the previous shutdown are used at the time of the next system startup.

Figure 33A:
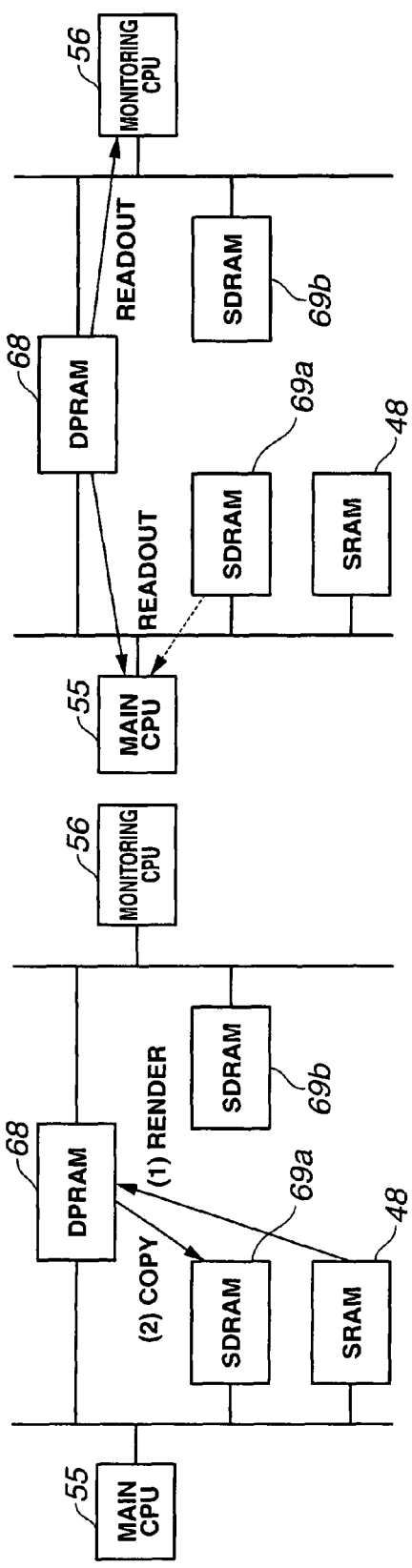

FIG. 33A illustrates an operation example of rending setting parameters, which is performed at the time of initialization processing. The operations here are the same as with the case described with FIG. 31A. Accordingly, description of the operations in this case will be omitted.

Also, the operations of changing the setting parameters in FIG. 33C will be described before using of the setting parameters in this case.

In addition to the static setting parameters, the above described scope-unique parameters include positional loop gain in the RL and UD directions, estimated lower limit value and upper limit value of the wire shape state, change over time, and so forth, and these change over time.

Accordingly, at the time of running, the main CPU 55 calculates the temporal change as to the setting values read out at the time of initialization, based on the measurement results of the slack sensor 61 by a predetermined period of time, and past history data and the like, at predetermined cycles, writes dynamic setting parameters from evaluation results made by an evaluation expression to the DPRAM 68, and updates to a state more suitable than the previous setting values.

Next, usage of the setting parameters shown in FIG. 33B will be described. In the event of using the setting parameters at the main CPU 55 side, static setting parameters are used by reading out from the SDRAM 69a in the same way as with the case of FIG. 31B, and for dynamic setting parameters the newest setting parameters are read out from the DPRAM 68 and used.

In the event of using setting parameters at the monitoring CPU 56 side, the setting parameters are used by reading out from the SDRAM 68 in the same way as with the case of FIG. 31B.

Figure 33D:
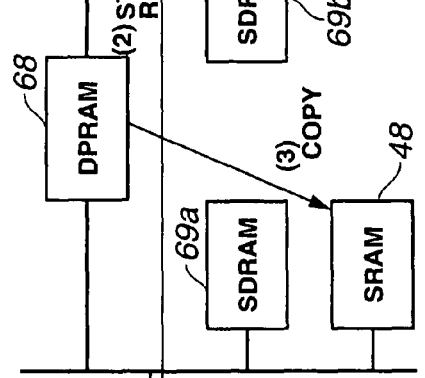
Figure 33C:
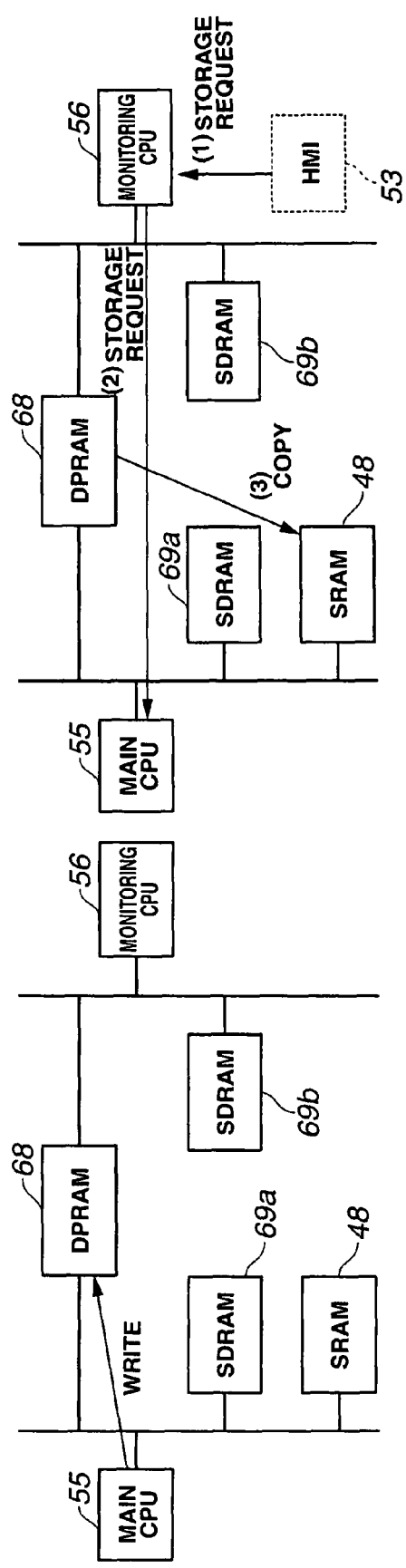

FIG. 33D illustrates the storage operations of the setting parameters. This case is the same operations as the case of FIG. 3 ID. Such dynamic setting parameters are updated to appropriate values a predetermined cycles or the like, and thus curving driving control can be performed in a suitable state with temporal effects being almost completely resolved. Note that dynamic parameters are saved in the SRAM card 48 and the time of ending, even if setting parameter storing operations are not performed.

Note that in the description given above, parameter files unique to the operation units, parameter files unique to the scopes, and so forth, are provided regarding multiple operation unit IDs and scope IDs, but the present invention need not to be restricted to such grouping names, and for example, an example may be made with grouping wherein parameter files for curving operation input means (specifically, input command device such as the joystick 36a) for performing curving instructions of the scope 2, parameter files for the curving mechanism unit 25 for performing curving driving, and so forth, can be uniquely regulated by the scope ID, for example.

FIG. 34 illustrates the details of data stored in the SRAM card 48. As described with reference to FIG. 32, the SRAM card 48 stores parameters unique to the operation unit, parameters unique to the scope, AWS parameters, user setting parameters, servo adjustment parameters, and also separately from these has a region for storing system log data (sysLog data), error log data (errLog data), and data log data (dtLog data).

System log data is data of system execution history, with the date-and -time, task name, and message data being stored for each file.

Also, error log data is data of error occurrence history, with the date-and -time, task name, and error code data being stored for each file.

Also, data log data stores, in a temporal manner, data of operation amount, command value, motor command, operating state of the encoder and the like. Measuring and saving these facilitates maintenance, and so forth.

With the present embodiment configured thus, not only parameters relating to the motor 27 which perform curving driving operations but also a great number of parameters such as settings for parameters relating to the encoder 35 which detects the rotational position thereof, parameters for the curving operation input unit which performs input operations for curving instructions, and so forth, can be set in detail and in a suitable manner regarding each scope 2 for a wide range of items, so electrically-driven curving operations can be performed more appropriately than with conventional examples.

FIG. 35 illustrates a detailed logic configuration of the interlock 57. This interlock 57 monitors various types of input or abnormalities 122 through 129 with regard to software commands 121 from the main CPU 55, and outputs output signals for controlling peripheral devices (curving mechanism unit 25 and AWS unit 49) side via gates 131 through 135.

Upon a power ON software command 121 being outputted from the main CPU 55 to the servo driver 45 and AWS unit 49, this passes through the two-input AND circuit gate 131 of the interlock 57 and becomes an output signal for turning the servo driver 45 and AWS unit 49 ON.

In this case, items to be monitored of abnormalities, equivalent to emergency stop input 122, are inputted to a first emergency stop self-holding circuit 145 for holding an emergency stop state, via OR circuits 141 through 144. The output of this first emergency stop self-holding circuit 145 passes through a two-input OR circuit gate 132 and becomes emergency stop output signals for causing emergency stopping, and also is inputted to the other inverting input terminal of the gate 131.

Note that emergency stop input 122 inputted to the OR circuits 141 through 144 are RAS power voltage, hardware (amp abnormality, encoder line breakage, FPGA abnormality), main CPU (WDT abnormality, software abnormality), and monitoring CPU (WDT abnormality, software abnormality), with the first emergency stop self-holding circuit 145 detecting occurrence of these abnormalities.

Also, the reset input 123 generates reset pulses from a one-shot circuit 146 by triggering the one-shot circuit 146, and resets the first emergency stop self-holding circuit 145 with the reset pulses.

Also, a main CPU software abnormality 125 and monitoring CPU software abnormality 126 are inputted to a second emergency stop self-holding circuit 148 via OR circuit 147, with the output of the second emergency stop self-holding circuit 148 being inputted to the other input terminal of the gate 132.

Note that the input of the abnormality clear 124 (outputted from the main CPU 55 side) resets the second emergency stop self-holding circuit 148 via the two-input OR circuit 149. This second emergency stop self-holding circuit 148 is also reset by the reset input 123 via the OR circuit 149.

Also, the interlock 57 outputs servo ON [RL], [UD] output signals via the gates 133 and 134, from the software commands 127 of servo ON [RL] commands and servo ON [UD] commands. In this case, the AND circuit gates 133 and 134 have inputted thereto system ready input 128 from software of the main CPU 55, and further the inverting input terminals of the AND circuit gates 133 and 134 have inputted thereto the output of the gate 132.

Also, clutch ON output signals are outputted via the gate 135 by a clutch ON software command 127. In this case, the output of the gate 132 is inputted to the inverting input terminal of the two-input AND circuit gate 135.

With such a configuration, in the event that there is even one abnormal input, such as the emergency stop input 122, emergency stop output is realized.

In this state, power ON of the servo driver and AWS unit, servo ON [RL] and [UD], and clutch ON are each forbidden, i.e., kept OFF. In other words, power ON of the servo driver and AWS unit, servo ON [RL] and [UD], and clutch ON are each permitted only in the event that there is no emergency stop output.

Also, as shown to the left side in FIG. 35, encoder light breakage in the emergency stop input 122 for example is detected at the main side, and the cause thereof is identified. Also, WDT and software abnormalities (including emergency stops and NMI (non-maskable interrupts)) are detected at the monitoring side. Also, the abnormality release input 124 can be detected from input/output of the release switch at the monitoring side. Further, system ready input 128 which is a software command can be detected by detecting the startup state of the monitoring side at the main side.

Note that the present invention is not restricted to the above-described embodiment, and it is needless to say that various modifications and applications can be made without departing from the essence of the present invention.

What is claimed is:

1. An electrically-operated curving control device comprising:
curving driving control means for performing electrical curving driving control of a curving portion of an endoscope; and
monitoring means for monitoring the state of electrically performing curving driving control of the curving portion, the monitoring means including state detecting means for detecting any of normal states to abnormal states at the time of electrically performing curving driving control of the curving portion, the state detecting means having an abnormality severity detecting function for detecting the severity of an abnormality in the event that an abnormality occurs.

2. An electrically-operated curving control device according to claim 1, wherein the monitoring means monitor the operating states of an operation input unit for performing operation input of curving instructions for the curving portion, and a curving driving mechanism for electrically performing curving driving of the curving portion.

3. An electrically-operated curving control device according to claim 1, wherein the monitoring means monitor the operating states of an operation input unit for performing operation input of curving instructions for the curving portion, control means for generating control signals for electrically performing curving driving of the curving portion based on the operation input of the operation input unit, and a curving driving mechanism which is controlled by the control means so as to electrically perform curving driving of the curving portion.

4. An electrically-operated curving control device according to claim 1, wherein the monitoring means comprise internal monitoring means for monitoring abnormal states within the electrically-operated curving control device.

5. An electrically-operated curving control device according to claim 4, wherein the internal monitoring means monitor occurrence of hardware and software abnormal states within the electrically-operated curving control device.

6. An electrically-operated curving control device according to claim 1, wherein the monitoring means further comprise display means for displaying a state detected by the state detecting means.

7. An electrically-operated curving control device according to claim 1, wherein the monitoring means further comprise processing means for performing processing corresponding to an abnormal state, in the event that an abnormal state occurs at the time of electrically performing curving driving control of the curving portion.

8. An electrically-operated curving control device according to claim 7, wherein the processing means perform processing for stopping the driving operations of the curving driving mechanism for electrically performing curving driving of the curving portion.

9. An electrically-operated curving control device according to claim 1, wherein the monitoring means further comprise intra-endoscope monitoring means for monitoring occurrence of abnormal states relating to curving driving within the endoscope.

10. An electrically-operated curving control device according to claim 9, wherein the intra-endoscope monitoring means monitor the states of units including a curving command device making up an operation input unit for performing curving instructions of the curving portion, a curving motor making up a curving driving mechanism for electrically performing curving driving of the curving portion, and tension of a curving wire.

11. An electrically-operated curving control device according to claim 10, wherein the intra-endoscope monitoring means monitor the states including command position and command speed of the curving command device, and the current position and speed of the curving motor.

* * * * *